US007749744B2

(12) United States Patent
Borchert et al.

(10) Patent No.: US 7,749,744 B2
(45) **Date of Patent: *Jul. 6, 2010**

(54) HYBRID ENZYMES

(75) Inventors: Torben V. Borchert, Birkerod (DK); Steffen Danielsen, Copenhagen Oe (DK); Eric J. Allain, Boone, NC (US)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/953,933

(22) Filed: Dec. 11, 2007

(65) Prior Publication Data

US 2008/0241901 A1 Oct. 2, 2008

Related U.S. Application Data

(60) Division of application No. 11/490,949, filed on Jul. 21, 2006, now Pat. No. 7,312,055, which is a continuation of application No. 10/974,508, filed on Oct. 27, 2004, now Pat. No. 7,129,069.

(60) Provisional application No. 60/515,017, filed on Oct. 28, 2003.

(51) Int. Cl.
*C12N 9/34* (2006.01)
*C12N 9/24* (2006.01)
*A61K 39/00* (2006.01)

(52) U.S. Cl. ..................... 435/205; 435/200; 424/192.1

(58) Field of Classification Search ................. 435/161, 435/101, 105, 200, 205; 536/23.2, 23.4, 536/23.7; 424/192.1
See application file for complete search history.

(56) References Cited

U.S. PATENT DOCUMENTS

| | | | |
|---|---|---|---|
| 4,238,345 | A | 12/1980 | Guilbert et al. |
| 2005/0042737 | A1 | 2/2005 | Vikso-Nielsen et al. |
| 2005/0054071 | A1 | 3/2005 | Udagawa et al. |

FOREIGN PATENT DOCUMENTS

| | | |
|---|---|---|
| WO | WO 90/00609 | 1/1990 |
| WO | WO 94/24158 | 10/1994 |
| WO | WO 95/16782 | 6/1995 |
| WO | WO 97/28243 | 8/1997 |
| WO | WO 97/28256 | 8/1997 |
| WO | WO 97/40127 | 10/1997 |
| WO | WO 97/40229 | 10/1997 |
| WO | WO 98/16191 | 4/1998 |
| WO | WO 98/16633 | 4/1998 |
| WO | WO 98/16905 | 5/1998 |
| WO | WO 98/22613 | 5/1998 |

OTHER PUBLICATIONS

Shibuya et al., Biosci. Biotech. Biochem., vol. 56, No. 6, pp. 884-889 (1992).

Nunberg et al., Molecular and Cellular Biology, vol. 4, No. 11,pp. 2306-2315 (1984).

Greenwood et al., Biotechnology and Bioengineering, vol. 44, pp. 1295-1305 (1994).

Moraes et al., Applied Microbiology and Biotechnology, vol. 43, No. 6, pp. 1067-1076 (1995).

Cornett et al., Protein Engineering, vol. 16, No. 7, pp. 521-529 (2003).

Ford Clark, Current Opinion in Biotechnology, vol. 10. No. 4, pp. 353-357 (1999).

Saha et al., Starke-Starch, vol. 41, No. 2, pp. 57-64 (1989).

*Primary Examiner*—Tekchand Saidha
(74) *Attorney, Agent, or Firm*—Elias Lambiris

(57) ABSTRACT

The present invention relates to a hybrid enzyme comprising at least one carbohydrate-binding module amino acid sequence and at least the catalytic module of a glucoamylase amino acid sequence. The invention also relates to the use of the hybrid enzyme in starch processing and especially ethanol production.

39 Claims, 1 Drawing Sheet

SEQUENCE LISTING

<160> NUMBER OF SEQ ID NOS: 99

<210> SEQ ID NO 1
<211> LENGTH: 396
<212> TYPE: DNA
<213> ORGANISM: Aspergillus kawachii
<220> FEATURE:
<221> NAME/KEY: CDS
<222> LOCATION: (1)..(396)

<400> SEQUENCE: 1

```
act agt aca tcc aaa gcc acc acc tcc tct tct tct tct tct gct gct       48
Thr Ser Thr Ser Lys Ala Thr Thr Ser Ser Ser Ser Ser Ser Ala Ala
1               5                   10                  15

gct act act tct tca tca tgc acc gca aca agc acc acc ctc ccc atc       96
Ala Thr Thr Ser Ser Ser Cys Thr Ala Thr Ser Thr Thr Leu Pro Ile
            20                  25                  30

acc ttc gaa gaa ctc gtc acc act acc tac ggg gaa gaa gtc tac ctc      144
Thr Phe Glu Glu Leu Val Thr Thr Thr Tyr Gly Glu Glu Val Tyr Leu
        35                  40                  45

agc gga tct atc tcc cag ctc gga gag tgg gat acg agt gac gcg gtg      192
Ser Gly Ser Ile Ser Gln Leu Gly Glu Trp Asp Thr Ser Asp Ala Val
    50                  55                  60

aag ttg tcc gcg gat gat tat acc tcg agt aac ccc gag tgg tct gtt      240
Lys Leu Ser Ala Asp Asp Tyr Thr Ser Ser Asn Pro Glu Trp Ser Val
65                  70                  75                  80

act gtg tcg ttg ccg gtg ggg acg acc ttc gag tat aag ttt att aag      288
Thr Val Ser Leu Pro Val Gly Thr Thr Phe Glu Tyr Lys Phe Ile Lys
                85                  90                  95

gtc gat gag ggt gga agt gtg act tgg gaa agt gat ccg aat agg gag      336
Val Asp Glu Gly Gly Ser Val Thr Trp Glu Ser Asp Pro Asn Arg Glu
            100                 105                 110

tat act gtg cct gaa tgt ggg aat ggg agt ggg gag acg gtg gtt gat      384
Tyr Thr Val Pro Glu Cys Gly Asn Gly Ser Gly Glu Thr Val Val Asp
        115                 120                 125

acg tgg agg tag                                                      396
Thr Trp Arg
    130
```

<210> SEQ ID NO 2
<211> LENGTH: 131
<212> TYPE: PRT
<213> ORGANISM: Aspergillus kawachii

<400> SEQUENCE: 2

```
Thr Ser Thr Ser Lys Ala Thr Thr Ser Ser Ser Ser Ser Ser Ala Ala
1               5                   10                  15

Ala Thr Thr Ser Ser Ser Cys Thr Ala Thr Ser Thr Thr Leu Pro Ile
            20                  25                  30

Thr Phe Glu Glu Leu Val Thr Thr Thr Tyr Gly Glu Glu Val Tyr Leu
        35                  40                  45

Ser Gly Ser Ile Ser Gln Leu Gly Glu Trp Asp Thr Ser Asp Ala Val
    50                  55                  60

Lys Leu Ser Ala Asp Asp Tyr Thr Ser Ser Asn Pro Glu Trp Ser Val
65                  70                  75                  80

Thr Val Ser Leu Pro Val Gly Thr Thr Phe Glu Tyr Lys Phe Ile Lys
                85                  90                  95

Val Asp Glu Gly Gly Ser Val Thr Trp Glu Ser Asp Pro Asn Arg Glu
            100                 105                 110
```

```
Tyr Thr Val Pro Glu Cys Gly Asn Gly Ser Gly Glu Thr Val Val Asp
        115                 120                 125

Thr Trp Arg
    130


<210> SEQ ID NO 3
<211> LENGTH: 102
<212> TYPE: PRT
<213> ORGANISM: Bacillus flavothermus

<400> SEQUENCE: 3

Ile Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val His Ala Val Gln Met Thr Pro Ser Ser Tyr Pro
        35                  40                  45

Thr Trp Thr Val Thr Ile Pro Leu Leu Gln Gly Gln Asn Ile Gln Phe
    50                  55                  60

Lys Phe Ile Lys Lys Asp Ser Ala Gly Asn Val Ile Trp Glu Asp Ile
65                  70                  75                  80

Ser Asn Arg Thr Tyr Thr Val Pro Thr Ala Ala Ser Gly Ala Tyr Thr
                85                  90                  95

Ala Ser Trp Asn Val Pro
            100


<210> SEQ ID NO 4
<211> LENGTH: 99
<212> TYPE: PRT
<213> ORGANISM: Bacillus sp.

<400> SEQUENCE: 4

Thr Ser Asn Val Thr Phe Thr Val Asn Asn Ala Thr Thr Val Tyr Gly
1               5                   10                  15

Gln Asn Val Tyr Val Val Gly Asn Ile Pro Glu Leu Gly Asn Trp Asn
            20                  25                  30

Ile Ala Asn Ala Ile Gln Met Thr Pro Ser Ser Tyr Pro Thr Trp Lys
        35                  40                  45

Thr Thr Val Ser Leu Pro Gln Gly Lys Ala Ile Glu Phe Lys Phe Ile
    50                  55                  60

Lys Lys Asp Ser Ala Gly Asn Val Ile Trp Glu Asn Ile Ala Asn Arg
65                  70                  75                  80

Thr Tyr Thr Val Pro Phe Ser Ser Thr Gly Ser Tyr Thr Ala Asn Trp
                85                  90                  95

Asn Val Pro


<210> SEQ ID NO 5
<211> LENGTH: 102
<212> TYPE: PRT
<213> ORGANISM: Alcaliphilic Bacillus

<400> SEQUENCE: 5

Thr Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val Asn Ala Val Gln Met Thr Pro Ser Ser Tyr Pro
```

-continued

```
        35                  40                  45

Thr Trp Val Val Thr Val Pro Leu Pro Gln Ser Gln Asn Ile Gln Phe
    50                  55                  60

Lys Phe Ile Lys Lys Asp Gly Ser Gly Asn Val Ile Trp Glu Asn Ile
65                  70                  75                  80

Ser Asn Arg Thr Tyr Thr Val Pro Thr Ala Ala Ser Gly Ala Tyr Thr
                85                  90                  95

Ala Asn Trp Asn Val Pro
            100


<210> SEQ ID NO 6
<211> LENGTH: 112
<212> TYPE: PRT
<213> ORGANISM: Hormoconis resinae

<400> SEQUENCE: 6

Cys Gln Val Ser Ile Thr Phe Asn Ile Asn Ala Thr Thr Tyr Tyr Gly
1               5                   10                  15

Glu Asn Leu Tyr Val Ile Gly Asn Ser Ser Asp Leu Gly Ala Trp Asn
            20                  25                  30

Ile Ala Asp Ala Tyr Pro Leu Ser Ala Ser Ala Tyr Thr Gln Asp Arg
        35                  40                  45

Pro Leu Trp Ser Ala Ala Ile Pro Leu Asn Ala Gly Glu Val Ile Ser
    50                  55                  60

Tyr Gln Tyr Val Arg Gln Glu Asp Cys Asp Gln Pro Tyr Ile Tyr Glu
65                  70                  75                  80

Thr Val Asn Arg Thr Leu Thr Val Pro Ala Cys Gly Gly Ala Ala Val
                85                  90                  95

Thr Thr Asp Asp Ala Trp Met Gly Pro Val Gly Ser Ser Gly Asn Cys
            100                 105                 110


<210> SEQ ID NO 7
<211> LENGTH: 95
<212> TYPE: PRT
<213> ORGANISM: Lentinula edodes

<400> SEQUENCE: 7

Val Ser Val Thr Phe Asn Val Asp Ala Ser Thr Leu Glu Gly Gln Asn
1               5                   10                  15

Val Tyr Leu Thr Gly Ala Val Asp Ala Leu Glu Asp Trp Ser Thr Asp
            20                  25                  30

Asn Ala Ile Leu Leu Ser Ser Ala Asn Tyr Pro Thr Trp Ser Val Thr
        35                  40                  45

Val Asp Leu Pro Gly Ser Thr Asp Val Gln Tyr Lys Tyr Ile Lys Lys
    50                  55                  60

Asp Gly Ser Gly Thr Val Thr Trp Glu Ser Asp Pro Asn Met Glu Ile
65                  70                  75                  80

Thr Thr Pro Ala Asn Gly Thr Tyr Ala Thr Asn Asp Thr Trp Arg
                85                  90                  95


<210> SEQ ID NO 8
<211> LENGTH: 107
<212> TYPE: PRT
<213> ORGANISM: Neurospora crassa

<400> SEQUENCE: 8

Cys Ala Ala Asp His Glu Val Leu Val Thr Phe Asn Glu Lys Val Thr
1               5                   10                  15
```

-continued

```
Thr Ser Tyr Gly Gln Thr Val Lys Val Val Gly Ser Ile Ala Ala Leu
            20                  25                  30

Gly Asn Trp Ala Pro Ala Ser Gly Val Thr Leu Ser Ala Lys Gln Tyr
        35                  40                  45

Ser Ser Ser Asn Pro Leu Trp Ser Thr Thr Ile Ala Leu Pro Gln Gly
    50                  55                  60

Thr Ser Phe Lys Tyr Lys Tyr Val Val Val Asn Ser Asp Gly Ser Val
65                  70                  75                  80

Lys Trp Glu Asn Asp Pro Asp Arg Ser Tyr Ala Val Gly Thr Asp Cys
                85                  90                  95

Ala Ser Thr Ala Thr Leu Asp Asp Thr Trp Arg
            100                 105


<210> SEQ ID NO 9
<211> LENGTH: 115
<212> TYPE: PRT
<213> ORGANISM: Talaromyces byssochlamydioides

<400> SEQUENCE: 9

Thr Thr Thr Gly Ala Ala Pro Cys Thr Thr Pro Thr Thr Val Ala Val
1               5                   10                  15

Thr Phe Asp Glu Ile Val Thr Thr Thr Tyr Gly Glu Thr Val Tyr Leu
            20                  25                  30

Ser Gly Ser Ile Pro Ala Leu Gly Asn Trp Asp Thr Ser Ser Ala Ile
        35                  40                  45

Ala Leu Ser Ala Val Asp Tyr Thr Ser Ser Asn Pro Leu Trp Tyr Val
    50                  55                  60

Thr Val Asn Leu Pro Ala Gly Thr Ser Phe Glu Tyr Lys Phe Phe Val
65                  70                  75                  80

Gln Gln Thr Asp Gly Thr Ile Val Trp Glu Asp Asp Pro Asn Arg Ser
                85                  90                  95

Tyr Thr Val Pro Ala Asn Cys Gly Gln Thr Thr Ala Ile Ile Asp Asp
            100                 105                 110

Ser Trp Gln
        115


<210> SEQ ID NO 10
<211> LENGTH: 115
<212> TYPE: PRT
<213> ORGANISM: Geosmithia cylindrospora:

<400> SEQUENCE: 10

Thr Ser Thr Gly Ser Ala Pro Cys Thr Thr Pro Thr Thr Val Ala Val
1               5                   10                  15

Thr Phe Asp Glu Ile Val Thr Thr Ser Tyr Gly Glu Thr Val Tyr Leu
            20                  25                  30

Ala Gly Ser Ile Ala Ala Leu Gly Asn Trp Asp Thr Asn Ser Ala Ile
        35                  40                  45

Ala Leu Ser Ala Ala Asp Tyr Thr Ser Asn Asn Asn Leu Trp Tyr Val
    50                  55                  60

Thr Val Asn Leu Ala Ala Gly Thr Ser Phe Gln Tyr Lys Phe Phe Val
65                  70                  75                  80

Lys Glu Thr Asp Ser Thr Ile Val Trp Glu Asp Asp Pro Asn Arg Ser
                85                  90                  95

Tyr Thr Val Pro Ala Asn Cys Gly Gln Thr Thr Ala Ile Ile Asp Asp
            100                 105                 110
```

-continued

```
Thr Trp Gln
        115


<210> SEQ ID NO 11
<211> LENGTH: 139
<212> TYPE: PRT
<213> ORGANISM: Scorias spongiosa

<400> SEQUENCE: 11

Ala Lys Val Pro Ser Thr Cys Ser Ala Ser Ser Ala Thr Gly Thr Cys
1               5                   10                  15

Thr Thr Ala Thr Ser Thr Phe Gly Gly Ser Thr Pro Thr Thr Ser Cys
            20                  25                  30

Ala Thr Thr Pro Thr Leu Thr Thr Val Leu Phe Asn Glu Arg Ala Thr
        35                  40                  45

Thr Asn Phe Gly Gln Asn Val His Leu Thr Gly Ser Ile Ser Gln Leu
    50                  55                  60

Gly Ser Trp Asp Thr Asp Ser Ala Val Ala Leu Ser Ala Val Asn Tyr
65                  70                  75                  80

Thr Ser Ser Asp Pro Leu Trp Phe Val Arg Val Gln Leu Pro Ala Gly
                85                  90                  95

Thr Ser Phe Gln Tyr Lys Tyr Phe Lys Lys Asp Ser Ser Asn Ala Val
            100                 105                 110

Ala Trp Glu Ser Asp Pro Asn Arg Ser Tyr Thr Val Pro Leu Asn Cys
        115                 120                 125

Ala Gly Thr Ala Thr Glu Asn Asp Thr Trp Arg
    130                 135


<210> SEQ ID NO 12
<211> LENGTH: 126
<212> TYPE: PRT
<213> ORGANISM: Eupenicillium ludwigii

<400> SEQUENCE: 12

Ser Thr Thr Thr Thr Ser Thr Thr Lys Thr Thr Thr Thr Ser Thr Thr
1               5                   10                  15

Thr Ser Cys Thr Thr Pro Thr Ala Val Ala Val Thr Phe Asp Leu Ile
            20                  25                  30

Ala Thr Thr Tyr Tyr Gly Glu Asn Ile Lys Ile Ala Gly Ser Ile Ser
        35                  40                  45

Gln Leu Gly Asp Trp Asp Thr Ser Asn Ala Val Ala Leu Ser Ala Ala
    50                  55                  60

Asp Tyr Thr Ser Ser Asp His Leu Trp Phe Val Asp Ile Asp Leu Pro
65                  70                  75                  80

Ala Gly Thr Val Phe Glu Tyr Lys Tyr Ile Arg Ile Glu Ser Asp Gly
                85                  90                  95

Ser Ile Glu Trp Glu Ser Asp Pro Asn Arg Ser Tyr Thr Val Pro Ala
            100                 105                 110

Ala Cys Ala Thr Thr Ala Val Thr Glu Asn Asp Thr Trp Arg
        115                 120                 125


<210> SEQ ID NO 13
<211> LENGTH: 116
<212> TYPE: PRT
<213> ORGANISM: Aspergillus japonicus

<400> SEQUENCE: 13
```

-continued

```
Lys Thr Ser Thr Thr Thr Ser Ser Cys Ser Thr Pro Thr Ser Val Ala
1               5                   10                  15

Val Thr Phe Asp Val Ile Ala Thr Thr Thr Tyr Gly Glu Asn Val Tyr
            20                  25                  30

Ile Ser Gly Ser Ile Ser Gln Leu Gly Ser Trp Asp Thr Ser Ser Ala
        35                  40                  45

Ile Ala Leu Ser Ala Ser Gln Tyr Thr Ser Ser Asn Asn Leu Trp Tyr
    50                  55                  60

Ala Thr Val His Leu Pro Ala Gly Thr Thr Phe Gln Tyr Lys Tyr Ile
65                  70                  75                  80

Arg Lys Glu Thr Asp Gly Ser Val Thr Trp Glu Ser Asp Pro Asn Arg
                85                  90                  95

Ser Tyr Thr Val Pro Ser Ser Cys Gly Val Ser Ser Ala Thr Glu Ser
            100                 105                 110

Asp Thr Trp Arg
        115


<210> SEQ ID NO 14
<211> LENGTH: 133
<212> TYPE: PRT
<213> ORGANISM: Penicillium cf. miczynskii

<400> SEQUENCE: 14

Thr Thr Thr Gly Gly Thr Thr Thr Ser Gln Gly Ser Thr Thr Thr Thr
1               5                   10                  15

Ser Lys Thr Ser Thr Thr Thr Ser Ser Cys Thr Ala Pro Thr Ser Val
            20                  25                  30

Ala Val Thr Phe Asp Leu Ile Ala Thr Thr Val Tyr Asp Glu Asn Val
        35                  40                  45

Gln Leu Ala Gly Ser Ile Ser Ala Leu Gly Ser Trp Asp Thr Ser Ser
    50                  55                  60

Ala Ile Arg Leu Ser Ala Ser Gln Tyr Thr Ser Ser Asn His Leu Trp
65                  70                  75                  80

Tyr Val Ala Val Ser Leu Pro Ala Gly Gln Val Phe Gln Tyr Lys Tyr
                85                  90                  95

Ile Arg Val Ala Ser Ser Gly Thr Ile Thr Trp Glu Ser Asp Pro Asn
            100                 105                 110

Leu Ser Tyr Thr Val Pro Val Ala Cys Ala Ala Thr Ala Val Thr Ile
        115                 120                 125

Ser Asp Thr Trp Arg
    130


<210> SEQ ID NO 15
<211> LENGTH: 116
<212> TYPE: PRT
<213> ORGANISM: Mz1 Penicillium sp.

<400> SEQUENCE: 15

Thr Lys Thr Ser Thr Ser Thr Ser Cys Thr Thr Pro Thr Ala Val Ala
1               5                   10                  15

Val Thr Phe Asp Leu Ile Ala Thr Thr Thr Tyr Gly Glu Asn Ile Lys
            20                  25                  30

Ile Ala Gly Ser Ile Ala Ala Leu Gly Ala Trp Asp Thr Asp Asp Ala
        35                  40                  45

Val Ala Leu Ser Ala Ala Asp Tyr Thr Asp Ser Asp His Leu Trp Phe
    50                  55                  60
```

-continued

```
Val Thr Gln Ser Ile Pro Ala Gly Thr Val Phe Glu Tyr Lys Tyr Ile
65                  70                  75                  80

Arg Val Glu Ser Asp Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
            100                 105                 110

Asp Thr Trp Arg
        115


<210> SEQ ID NO 16
<211> LENGTH: 114
<212> TYPE: PRT
<213> ORGANISM: Thysanophora sp

<400> SEQUENCE: 16

Phe Thr Ser Thr Thr Lys Thr Ser Cys Thr Thr Pro Thr Ser Val Ala
1               5                   10                  15

Val Thr Phe Asp Leu Ile Ala Thr Thr Thr Tyr Gly Glu Ser Ile Arg
            20                  25                  30

Leu Val Gly Ser Ile Ser Glu Leu Gly Asp Trp Asp Thr Gly Ser Ala
        35                  40                  45

Ile Ala Leu His Ala Thr Asp Tyr Thr Asp Ser Asp His Leu Trp Phe
    50                  55                  60

Val Thr Val Gly Leu Pro Ala Gly Ala Ser Phe Glu Tyr Lys Tyr Ile
65                  70                  75                  80

Arg Val Glu Ser Ser Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
            100                 105                 110

Asp Thr


<210> SEQ ID NO 17
<211> LENGTH: 111
<212> TYPE: PRT
<213> ORGANISM: Humicola grisea var. thermoidea

<400> SEQUENCE: 17

Ala Asp Ala Ser Glu Val Tyr Val Thr Phe Asn Glu Arg Val Ser Thr
1               5                   10                  15

Ala Trp Gly Glu Thr Ile Lys Val Val Gly Asn Val Pro Ala Leu Gly
            20                  25                  30

Asn Trp Asp Thr Ser Lys Ala Val Thr Leu Ser Ala Ser Gly Tyr Lys
        35                  40                  45

Ser Asn Asp Pro Leu Trp Ser Ile Thr Val Pro Ile Lys Ala Thr Gly
    50                  55                  60

Ser Ala Val Gln Tyr Lys Tyr Ile Lys Val Gly Thr Asn Gly Lys Ile
65                  70                  75                  80

Thr Trp Glu Ser Asp Pro Asn Arg Ser Ile Thr Leu Gln Thr Ala Ser
                85                  90                  95

Ser Ala Gly Lys Cys Ala Ala Gln Thr Val Asn Asp Ser Trp Arg
            100                 105                 110


<210> SEQ ID NO 18
<211> LENGTH: 108
<212> TYPE: PRT
<213> ORGANISM: Aspergillus niger

<400> SEQUENCE: 18
```

-continued

```
Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105
```

<210> SEQ ID NO 19
<211> LENGTH: 97
<212> TYPE: PRT
<213> ORGANISM: Aspergillus rolfsii

<400> SEQUENCE: 19

```
Val Glu Val Thr Phe Asp Val Tyr Ala Thr Thr Val Tyr Gly Gln Asn
1               5                   10                  15

Ile Tyr Ile Thr Gly Asp Val Ser Glu Leu Gly Asn Trp Thr Pro Ala
            20                  25                  30

Asn Gly Val Ala Leu Ser Ser Ala Asn Tyr Pro Thr Trp Ser Ala Thr
        35                  40                  45

Ile Ala Leu Pro Ala Asp Thr Thr Ile Gln Tyr Lys Tyr Val Asn Ile
    50                  55                  60

Asp Gly Ser Thr Val Ile Trp Glu Asp Ala Ile Ser Asn Arg Glu Ile
65                  70                  75                  80

Thr Thr Pro Ala Ser Gly Thr Tyr Thr Glu Lys Asp Thr Trp Asp Glu
                85                  90                  95

Ser
```

<210> SEQ ID NO 20
<211> LENGTH: 38
<212> TYPE: PRT
<213> ORGANISM: Aspergillus niger

<400> SEQUENCE: 20

```
Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
            20                  25                  30

Thr Ser Ser Thr Ser Ala
        35
```

<210> SEQ ID NO 21
<211> LENGTH: 31
<212> TYPE: PRT
<213> ORGANISM: Aspergillus kawachii

<400> SEQUENCE: 21

```
Thr Thr Thr Thr Thr Thr Ala Ala Ala Thr Ser Thr Ser Lys Ala Thr
1               5                   10                  15

Thr Ser Ser Ser Ser Ser Ser Ala Ala Ala Thr Thr Ser Ser Ser
```

-continued

```
20                  25                  30


<210> SEQ ID NO 22
<211> LENGTH: 8
<212> TYPE: PRT
<213> ORGANISM: Artificial
<220> FEATURE:
<223> OTHER INFORMATION: Synthetic

<400> SEQUENCE: 22

Pro Glu Pro Thr Pro Glu Pro Thr
1               5


<210> SEQ ID NO 23
<211> LENGTH: 1605
<212> TYPE: DNA
<213> ORGANISM: Aspergillus niger
<220> FEATURE:
<221> NAME/KEY: CDS
<222> LOCATION: (1)..(1602)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1602)

<400> SEQUENCE: 23

atg tcg ttc cga tct cta ctc gcc ctg agc ggc ctc gtc tgc aca ggg       48
Met Ser Phe Arg Ser Leu Leu Ala Leu Ser Gly Leu Val Cys Thr Gly
                -20                 -15                 -10

ttg gca aat gtg att tcc aag cgc gcg acc ttg gat tca tgg ttg agc       96
Leu Ala Asn Val Ile Ser Lys Arg Ala Thr Leu Asp Ser Trp Leu Ser
            -5              -1  1               5

aac gaa gcg acc gtg gct cgt act gcc atc ctg aat aac atc ggg gcg      144
Asn Glu Ala Thr Val Ala Arg Thr Ala Ile Leu Asn Asn Ile Gly Ala
    10                  15                  20

gac ggt gct tgg gtg tcg ggc gcg gac tct ggc att gtc gtt gct agt      192
Asp Gly Ala Trp Val Ser Gly Ala Asp Ser Gly Ile Val Val Ala Ser
25                  30                  35                  40

ccc agc acg gat aac ccg gac tac ttc tac acc tgg act cgc gac tct      240
Pro Ser Thr Asp Asn Pro Asp Tyr Phe Tyr Thr Trp Thr Arg Asp Ser
                45                  50                  55

ggt ctc gtc ctc aag acc ctc gtc gat ctc ttc cga aat gga gat acc      288
Gly Leu Val Leu Lys Thr Leu Val Asp Leu Phe Arg Asn Gly Asp Thr
            60                  65                  70

agt ctc ctc tcc acc att gag aac tac atc tcc gcc cag gca att gtc      336
Ser Leu Leu Ser Thr Ile Glu Asn Tyr Ile Ser Ala Gln Ala Ile Val
        75                  80                  85

cag ggt atc agt aac ccc tct ggt gat ctg tcc agc ggc gct ggt ctc      384
Gln Gly Ile Ser Asn Pro Ser Gly Asp Leu Ser Ser Gly Ala Gly Leu
    90                  95                  100

ggt gaa ccc aag ttc aat gtc gat gag act gcc tac act ggt tct tgg      432
Gly Glu Pro Lys Phe Asn Val Asp Glu Thr Ala Tyr Thr Gly Ser Trp
105                 110                 115                 120

gga cgg ccg cag cga gat ggt ccg gct ctg aga gca act gct atg atc      480
Gly Arg Pro Gln Arg Asp Gly Pro Ala Leu Arg Ala Thr Ala Met Ile
                125                 130                 135

ggc ttc ggg cag tgg ctg ctt gac aat ggc tac acc agc acc gca acg      528
Gly Phe Gly Gln Trp Leu Leu Asp Asn Gly Tyr Thr Ser Thr Ala Thr
            140                 145                 150

gac att gtt tgg ccc ctc gtt agg aac gac ctg tcg tat gtg gct caa      576
Asp Ile Val Trp Pro Leu Val Arg Asn Asp Leu Ser Tyr Val Ala Gln
        155                 160                 165
```

-continued

```
tac tgg aac cag aca gga tat gat ctc tgg gaa gaa gtc aat ggc tcg      624
Tyr Trp Asn Gln Thr Gly Tyr Asp Leu Trp Glu Glu Val Asn Gly Ser
    170                 175                 180

tct ttc ttt acg att gct gtg caa cac cgc gcc ctt gtc gaa ggt agt      672
Ser Phe Phe Thr Ile Ala Val Gln His Arg Ala Leu Val Glu Gly Ser
185                 190                 195                 200

gcc ttc gcg acg gcc gtc ggc tcg tcc tgc tcc tgg tgt gat tct cag      720
Ala Phe Ala Thr Ala Val Gly Ser Ser Cys Ser Trp Cys Asp Ser Gln
                205                 210                 215

gca ccc gaa att ctc tgc tac ctg cag tcc ttc tgg acc ggc agc ttc      768
Ala Pro Glu Ile Leu Cys Tyr Leu Gln Ser Phe Trp Thr Gly Ser Phe
            220                 225                 230

att ctg gcc aac ttc gat agc agc cgt tcc ggc aag gac gca aac acc      816
Ile Leu Ala Asn Phe Asp Ser Ser Arg Ser Gly Lys Asp Ala Asn Thr
        235                 240                 245

ctc ctg gga agc atc cac acc ttt gat cct gag gcc gca tgc gac gac      864
Leu Leu Gly Ser Ile His Thr Phe Asp Pro Glu Ala Ala Cys Asp Asp
    250                 255                 260

tcc acc ttc cag ccc tgc tcc ccg cgc gcg ctc gcc aac cac aag gag      912
Ser Thr Phe Gln Pro Cys Ser Pro Arg Ala Leu Ala Asn His Lys Glu
265                 270                 275                 280

gtt gta gac tct ttc cgc tca atc tat acc ctc aac gat ggt ctc agt      960
Val Val Asp Ser Phe Arg Ser Ile Tyr Thr Leu Asn Asp Gly Leu Ser
            285                 290                 295

gac agc gag gct gtt gcg gtg ggt cgg tac cct gag gac acg tac tac     1008
Asp Ser Glu Ala Val Ala Val Gly Arg Tyr Pro Glu Asp Thr Tyr Tyr
            300                 305                 310

aac ggc aac ccg tgg ttc ctg tgc acc ttg gct gcc gca gag cag ttg     1056
Asn Gly Asn Pro Trp Phe Leu Cys Thr Leu Ala Ala Ala Glu Gln Leu
        315                 320                 325

tac gat gct cta tac cag tgg gac aag cag ggg tcg ttg gag gtc aca     1104
Tyr Asp Ala Leu Tyr Gln Trp Asp Lys Gln Gly Ser Leu Glu Val Thr
    330                 335                 340

gat gtg tcg ctg gac ttc ttc aag gca ctg tac agc gat gct gct act     1152
Asp Val Ser Leu Asp Phe Phe Lys Ala Leu Tyr Ser Asp Ala Ala Thr
345                 350                 355                 360

ggc acc tac tct tcg tcc agt tcg act tat agt agc att gta gat gcc     1200
Gly Thr Tyr Ser Ser Ser Ser Ser Thr Tyr Ser Ser Ile Val Asp Ala
            365                 370                 375

gtg aag act ttc gcc gat ggc ttc gtc tct att gtg gaa act cac gcc     1248
Val Lys Thr Phe Ala Asp Gly Phe Val Ser Ile Val Glu Thr His Ala
            380                 385                 390

gca agc aac ggc tcc atg tcc gag caa tac gac aag tct gat ggc gag     1296
Ala Ser Asn Gly Ser Met Ser Glu Gln Tyr Asp Lys Ser Asp Gly Glu
        395                 400                 405

cag ctt tcc gct cgc gac ctg acc tgg tct tat gct gct ctg ctg acc     1344
Gln Leu Ser Ala Arg Asp Leu Thr Trp Ser Tyr Ala Ala Leu Leu Thr
    410                 415                 420

gcc aac aac cgt cgt aac tcc gtc gtg cct gct tct tgg ggc gag acc     1392
Ala Asn Asn Arg Arg Asn Ser Val Val Pro Ala Ser Trp Gly Glu Thr
425                 430                 435                 440

tct gcc agc agc gtg ccc ggc acc tgt gcg gcc aca tct gcc att ggt     1440
Ser Ala Ser Ser Val Pro Gly Thr Cys Ala Ala Thr Ser Ala Ile Gly
            445                 450                 455

acc tac agc agt gtg act gtc acc tcg tgg ccg agt atc gtg gct act     1488
Thr Tyr Ser Ser Val Thr Val Thr Ser Trp Pro Ser Ile Val Ala Thr
            460                 465                 470

ggc ggc acc act acg acg gct acc ccc act gga tcc ggc agc gtg acc     1536
Gly Gly Thr Thr Thr Thr Ala Thr Pro Thr Gly Ser Gly Ser Val Thr
```

-continued

```
        475                 480                 485

tcg acc agc aag acc acc gcg act gct agc aag acc agc acc acg acc      1584
Ser Thr Ser Lys Thr Thr Ala Thr Ala Ser Lys Thr Ser Thr Thr Thr
    490                 495                 500

cgc tct ggt atg tca ctg tga                                          1605
Arg Ser Gly Met Ser Leu
505                 510


<210> SEQ ID NO 24
<211> LENGTH: 534
<212> TYPE: PRT
<213> ORGANISM: Aspergillus niger

<400> SEQUENCE: 24

Met Ser Phe Arg Ser Leu Leu Ala Leu Ser Gly Leu Val Cys Thr Gly
                -20                 -15                 -10

Leu Ala Asn Val Ile Ser Lys Arg Ala Thr Leu Asp Ser Trp Leu Ser
            -5                  -1  1               5

Asn Glu Ala Thr Val Ala Arg Thr Ala Ile Leu Asn Asn Ile Gly Ala
    10                  15                  20

Asp Gly Ala Trp Val Ser Gly Ala Asp Ser Gly Ile Val Val Ala Ser
25                  30                  35                  40

Pro Ser Thr Asp Asn Pro Asp Tyr Phe Tyr Thr Trp Thr Arg Asp Ser
                45                  50                  55

Gly Leu Val Leu Lys Thr Leu Val Asp Leu Phe Arg Asn Gly Asp Thr
            60                  65                  70

Ser Leu Leu Ser Thr Ile Glu Asn Tyr Ile Ser Ala Gln Ala Ile Val
        75                  80                  85

Gln Gly Ile Ser Asn Pro Ser Gly Asp Leu Ser Ser Gly Ala Gly Leu
    90                  95                  100

Gly Glu Pro Lys Phe Asn Val Asp Glu Thr Ala Tyr Thr Gly Ser Trp
105                 110                 115                 120

Gly Arg Pro Gln Arg Asp Gly Pro Ala Leu Arg Ala Thr Ala Met Ile
                125                 130                 135

Gly Phe Gly Gln Trp Leu Leu Asp Asn Gly Tyr Thr Ser Thr Ala Thr
            140                 145                 150

Asp Ile Val Trp Pro Leu Val Arg Asn Asp Leu Ser Tyr Val Ala Gln
        155                 160                 165

Tyr Trp Asn Gln Thr Gly Tyr Asp Leu Trp Glu Glu Val Asn Gly Ser
    170                 175                 180

Ser Phe Phe Thr Ile Ala Val Gln His Arg Ala Leu Val Glu Gly Ser
185                 190                 195                 200

Ala Phe Ala Thr Ala Val Gly Ser Ser Cys Ser Trp Cys Asp Ser Gln
                205                 210                 215

Ala Pro Glu Ile Leu Cys Tyr Leu Gln Ser Phe Trp Thr Gly Ser Phe
            220                 225                 230

Ile Leu Ala Asn Phe Asp Ser Ser Arg Ser Gly Lys Asp Ala Asn Thr
        235                 240                 245

Leu Leu Gly Ser Ile His Thr Phe Asp Pro Glu Ala Ala Cys Asp Asp
    250                 255                 260

Ser Thr Phe Gln Pro Cys Ser Pro Arg Ala Leu Ala Asn His Lys Glu
265                 270                 275                 280

Val Val Asp Ser Phe Arg Ser Ile Tyr Thr Leu Asn Asp Gly Leu Ser
                285                 290                 295

Asp Ser Glu Ala Val Ala Val Gly Arg Tyr Pro Glu Asp Thr Tyr Tyr
```

-continued

```
            300                 305                 310

Asn Gly Asn Pro Trp Phe Leu Cys Thr Leu Ala Ala Ala Glu Gln Leu
        315                 320                 325

Tyr Asp Ala Leu Tyr Gln Trp Asp Lys Gln Gly Ser Leu Glu Val Thr
    330                 335                 340

Asp Val Ser Leu Asp Phe Phe Lys Ala Leu Tyr Ser Asp Ala Ala Thr
345                 350                 355                 360

Gly Thr Tyr Ser Ser Ser Ser Ser Thr Tyr Ser Ser Ile Val Asp Ala
                365                 370                 375

Val Lys Thr Phe Ala Asp Gly Phe Val Ser Ile Val Glu Thr His Ala
            380                 385                 390

Ala Ser Asn Gly Ser Met Ser Glu Gln Tyr Asp Lys Ser Asp Gly Glu
        395                 400                 405

Gln Leu Ser Ala Arg Asp Leu Thr Trp Ser Tyr Ala Ala Leu Leu Thr
    410                 415                 420

Ala Asn Asn Arg Arg Asn Ser Val Val Pro Ala Ser Trp Gly Glu Thr
425                 430                 435                 440

Ser Ala Ser Ser Val Pro Gly Thr Cys Ala Ala Thr Ser Ala Ile Gly
                445                 450                 455

Thr Tyr Ser Ser Val Thr Val Thr Ser Trp Pro Ser Ile Val Ala Thr
            460                 465                 470

Gly Gly Thr Thr Thr Thr Ala Thr Pro Thr Gly Ser Gly Ser Val Thr
        475                 480                 485

Ser Thr Ser Lys Thr Thr Ala Thr Ala Ser Lys Thr Ser Thr Thr Thr
    490                 495                 500

Arg Ser Gly Met Ser Leu
505                 510


<210> SEQ ID NO 25
<211> LENGTH: 591
<212> TYPE: PRT
<213> ORGANISM: Talaromyces emersonii

<400> SEQUENCE: 25

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Asn Arg Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160
```

-continued

```
Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ser Ala Ser Ser Val Leu
        435                 440                 445

Ala Val Cys Ser Ala Thr Ser Ala Thr Gly Pro Tyr Ser Thr Ala Thr
    450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
                485                 490                 495

Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
        515                 520                 525

Asp Ala Tyr Thr Asn Ser Asn Pro Leu Trp Tyr Val Thr Val Asn Leu
    530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Asp Pro Asn Arg Ser Tyr Thr Val Pro
                565                 570                 575

Ala Tyr Cys Gly Gln Thr Thr Ala Ile Leu Asp Asp Ser Trp Gln
```

-continued

```
            580                 585                 590

<210> SEQ ID NO 26
<211> LENGTH: 451
<212> TYPE: PRT
<213> ORGANISM: Athelium rolfsii

<400> SEQUENCE: 26

Gln Ser Ala Ser Ala Thr Ala Tyr Leu Thr Lys Glu Ser Ala Val Ala
1               5                   10                  15

Lys Asn Gly Val Leu Cys Asn Ile Gly Ser Gln Gly Cys Met Ser Glu
            20                  25                  30

Gly Ala Tyr Ser Gly Ile Val Ile Ala Ser Pro Ser Lys Thr Ser Pro
        35                  40                  45

Asp Tyr Leu Tyr Thr Trp Thr Arg Asp Ser Ser Leu Val Phe Lys Met
    50                  55                  60

Leu Ile Asp Gln Tyr Thr Asn Gly Leu Asp Thr Thr Leu Arg Thr Leu
65                  70                  75                  80

Ile Asp Glu Phe Val Ser Ala Glu Ala Thr Ile Gln Gln Thr Ser Asn
                85                  90                  95

Ser Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ala Ile Met Thr Tyr Ala Thr Tyr Leu
    130                 135                 140

Tyr Asn Asn Gly Asn Thr Ser Tyr Val Thr Asn Thr Leu Trp Pro Ile
145                 150                 155                 160

Ile Lys Leu Asp Leu Asp Tyr Val Asn Ser Asp Trp Asn Gln Thr Thr
                165                 170                 175

Phe Asp Leu Trp Glu Glu Val Asp Ser Ser Ser Phe Phe Thr Thr Ala
            180                 185                 190

Val Gln His Arg Ala Leu Val Gln Gly Ala Ala Phe Ala Thr Leu Ile
        195                 200                 205

Gly Gln Thr Ser Ser Ala Ser Thr Tyr Ser Ala Thr Ala Pro Ser Ile
    210                 215                 220

Leu Cys Phe Leu Gln Ser Tyr Trp Asn Thr Asn Gly Tyr Trp Thr Ala
225                 230                 235                 240

Asn Thr Gly Gly Gly Arg Ser Gly Lys Asp Ala Asn Thr Ile Leu Ala
                245                 250                 255

Ser Ile His Thr Phe Asp Ala Ser Ala Gly Cys Ser Ala Ala Thr Ser
            260                 265                 270

Gln Pro Cys Ser Asp Val Ala Leu Ala Asn Leu Lys Val Tyr Val Asp
        275                 280                 285

Ser Phe Arg Ser Ile Tyr Thr Ile Asn Ser Gly Ile Ser Ser Thr Ser
    290                 295                 300

Gly Val Ala Thr Gly Arg Tyr Pro Glu Asp Ser Tyr Tyr Asn Gly Asn
305                 310                 315                 320

Pro Trp Tyr Leu Cys Thr Leu Ala Val Ala Glu Gln Leu Tyr Asp Ala
                325                 330                 335

Leu Ile Val Trp Lys Ala Ala Gly Glu Leu Asn Val Thr Ser Val Ser
            340                 345                 350

Leu Ala Phe Phe Gln Gln Phe Asp Ser Ser Ile Thr Ala Gly Thr Tyr
        355                 360                 365
```

-continued

```
Ala Ser Ser Ser Ser Val Tyr Thr Ser Leu Ile Ser Asp Ile Gln Ala
    370                 375                 380

Phe Ala Asp Glu Phe Val Asp Ile Val Ala Lys Tyr Thr Pro Ser Ser
385                 390                 395                 400

Gly Phe Leu Ser Glu Gln Tyr Asp Lys Ser Thr Gly Ala Gln Asp Ser
                405                 410                 415

Ala Ala Asn Leu Thr Trp Ser Tyr Ala Ala Ala Ile Thr Ala Tyr Gln
            420                 425                 430

Ala Arg Asn Gly Phe Thr Gly Ala Ser Trp Gly Ala Lys Gly Val Ser
        435                 440                 445

Thr Ser Cys
    450
```

<210> SEQ ID NO 27
<211> LENGTH: 17
<212> TYPE: PRT
<213> ORGANISM: Athelia rolfsii
<220> FEATURE:
<221> NAME/KEY: MISC_FEATURE
<222> LOCATION: (1)..()
<223> OTHER INFORMATION: Linker

<400> SEQUENCE: 27

```
Ser Thr Gly Ala Thr Ser Pro Gly Gly Ser Ser Gly Ser Val Glu Val
1               5                   10                  15

Thr
```

<210> SEQ ID NO 28
<211> LENGTH: 93
<212> TYPE: PRT
<213> ORGANISM: Athelia rolfsii
<220> FEATURE:
<221> NAME/KEY: MISC_FEATURE
<222> LOCATION: (1)..()
<223> OTHER INFORMATION: Athelium rolfsii CBM

<400> SEQUENCE: 28

```
Phe Asp Val Tyr Ala Thr Thr Val Tyr Gly Gln Asn Ile Tyr Ile Thr
1               5                   10                  15

Gly Asp Val Ser Glu Leu Gly Asn Trp Thr Pro Ala Asn Gly Val Ala
            20                  25                  30

Leu Ser Ser Ala Asn Tyr Pro Thr Trp Ser Ala Thr Ile Ala Leu Pro
        35                  40                  45

Ala Asp Thr Thr Ile Gln Tyr Lys Tyr Val Asn Ile Asp Gly Ser Thr
    50                  55                  60

Val Ile Trp Glu Asp Ala Ile Ser Asn Arg Glu Ile Thr Thr Pro Ala
65                  70                  75                  80

Ser Gly Thr Tyr Thr Glu Lys Asp Thr Trp Asp Glu Ser
                85                  90
```

<210> SEQ ID NO 29
<211> LENGTH: 33
<212> TYPE: PRT
<213> ORGANISM: Aspergillus niger-Talaromyces emersonii
<220> FEATURE:
<221> NAME/KEY: MISC_FEATURE
<222> LOCATION: (1)..(33)
<223> OTHER INFORMATION: Fusion junction at position 8

<400> SEQUENCE: 29

```
Ser Ser Val Pro Gly Thr Cys Ser Ala Thr Ser Ala Thr Gly Pro Tyr
1               5                   10                  15
```

Ser Thr Ala Thr Asn Thr Val Trp Pro Ser Ser Gly Ser Gly Ser Ser
20 25 30

Thr

<210> SEQ ID NO 30
<211> LENGTH: 33
<212> TYPE: PRT
<213> ORGANISM: Aspergillus niger-Talaromyces emersonii
<220> FEATURE:
<221> NAME/KEY: MISC_FEATURE
<222> LOCATION: (1)..(33)
<223> OTHER INFORMATION: fusing junction point at position 16

<400> SEQUENCE: 30

Ser Ser Val Pro Gly Thr Cys Ala Ala Thr Ser Ala Ile Gly Thr Tyr
1 5 10 15

Ser Thr Ala Thr Asn Thr Val Trp Pro Ser Ser Gly Ser Gly Ser Ser
20 25 30

Thr

<210> SEQ ID NO 31
<211> LENGTH: 33
<212> TYPE: PRT
<213> ORGANISM: Aspergillus niger-Talaromyces emersonii
<220> FEATURE:
<221> NAME/KEY: MISC_FEATURE
<222> LOCATION: (1)..(33)
<223> OTHER INFORMATION: fusion junction point at position 25

<400> SEQUENCE: 31

Ser Ser Val Pro Gly Thr Cys Ala Ala Thr Ser Ala Ile Gly Thr Tyr
1 5 10 15

Ser Ser Val Thr Val Thr Ser Trp Pro Ser Ser Gly Ser Gly Ser Ser
20 25 30

Thr

<210> SEQ ID NO 32
<211> LENGTH: 33
<212> TYPE: PRT
<213> ORGANISM: Aspergillus niger-Athelia rolfsii
<220> FEATURE:
<221> NAME/KEY: MISC_FEATURE
<222> LOCATION: (1)..(33)
<223> OTHER INFORMATION: fusion junction at position 8

<400> SEQUENCE: 32

Ser Ser Val Pro Gly Thr Cys Ser Thr Gly Ala Thr Ser Pro Gly Gly
1 5 10 15

Ser Ser Gly Ser Val Glu Val Thr Phe Asp Val Tyr Ala Thr Thr Val
20 25 30

Tyr

<210> SEQ ID NO 33
<211> LENGTH: 33
<212> TYPE: PRT
<213> ORGANISM: Aspergillus niger-Athelia rolfsii
<220> FEATURE:
<221> NAME/KEY: MISC_FEATURE
<222> LOCATION: (1)..(33)
<223> OTHER INFORMATION: fusion junction point at position 16

<400> SEQUENCE: 33

Ser Ser Val Pro Gly Thr Cys Ala Ala Thr Ser Ala Ile Gly Thr Gly

-continued

```
1               5                   10                  15

Ser Ser Gly Ser Val Glu Val Thr Phe Asp Val Tyr Ala Thr Thr Val
            20                  25                  30

Tyr


<210> SEQ ID NO 34
<211> LENGTH: 33
<212> TYPE: PRT
<213> ORGANISM: Aspergillus niger-Athelia rolfsii
<220> FEATURE:
<221> NAME/KEY: MISC_FEATURE
<222> LOCATION: (1)..(33)
<223> OTHER INFORMATION: fusion junction at position 25

<400> SEQUENCE: 34

Ser Ser Val Pro Gly Thr Cys Ala Ala Thr Ser Ala Ile Gly Thr Tyr
1               5                   10                  15

Ser Ser Val Thr Val Thr Ser Trp Phe Asp Val Tyr Ala Thr Thr Val
            20                  25                  30

Tyr


<210> SEQ ID NO 35
<211> LENGTH: 33
<212> TYPE: PRT
<213> ORGANISM: Athelia rolfsii-Talaromyces emersonii
<220> FEATURE:
<221> NAME/KEY: MISC_FEATURE
<222> LOCATION: (1)..(33)
<223> OTHER INFORMATION: fusion junction at position 8

<400> SEQUENCE: 35

Gly Val Ser Thr Ser Cys Ser Ala Thr Ser Ala Thr Gly Pro Tyr Ser
1               5                   10                  15

Thr Ala Thr Asn Thr Val Trp Pro Ser Ser Gly Ser Gly Ser Ser Thr
            20                  25                  30

Thr


<210> SEQ ID NO 36
<211> LENGTH: 33
<212> TYPE: PRT
<213> ORGANISM: Athelia rolfsii-Talaromyces emersonii
<220> FEATURE:
<221> NAME/KEY: MISC_FEATURE
<222> LOCATION: (1)..(33)
<223> OTHER INFORMATION: fusion junction at position 15

<400> SEQUENCE: 36

Gly Val Ser Thr Ser Cys Ser Thr Gly Ala Thr Ser Pro Gly Tyr Ser
1               5                   10                  15

Thr Ala Thr Asn Thr Val Trp Pro Ser Ser Gly Ser Gly Ser Ser Thr
            20                  25                  30

Thr


<210> SEQ ID NO 37
<211> LENGTH: 33
<212> TYPE: PRT
<213> ORGANISM: Athelia rolfsii-Talaromyces emersonii
<220> FEATURE:
<221> NAME/KEY: MISC_FEATURE
<222> LOCATION: (1)..(33)
<223> OTHER INFORMATION: fusion junction at position 24

<400> SEQUENCE: 37
```

-continued

```
Gly Val Ser Thr Ser Cys Ser Thr Gly Ala Thr Ser Pro Gly Gly Ser
1               5                   10                  15

Ser Gly Ser Val Glu Val Thr Pro Ser Ser Gly Ser Gly Ser Ser Thr
            20                  25                  30

Thr


<210> SEQ ID NO 38
<211> LENGTH: 33
<212> TYPE: PRT
<213> ORGANISM: Athelia rolfsii-Aspergillus niger
<220> FEATURE:
<221> NAME/KEY: MISC_FEATURE
<222> LOCATION: (1)..(33)
<223> OTHER INFORMATION: fusion junction at position 7

<400> SEQUENCE: 38

Gly Val Ser Thr Ser Cys Ala Ala Thr Ser Ala Ile Gly Thr Tyr Ser
1               5                   10                  15

Ser Val Thr Val Thr Ser Trp Pro Ser Ile Val Ala Thr Gly Gly Thr
            20                  25                  30

Thr


<210> SEQ ID NO 39
<211> LENGTH: 33
<212> TYPE: PRT
<213> ORGANISM: Athelia rolfsii-Aspergillus niger
<220> FEATURE:
<221> NAME/KEY: MISC_FEATURE
<222> LOCATION: (1)..(33)
<223> OTHER INFORMATION: fusion junction at position 15

<400> SEQUENCE: 39

Gly Val Ser Thr Ser Cys Ser Thr Gly Ala Thr Ser Pro Gly Tyr Ser
1               5                   10                  15

Ser Val Thr Val Thr Ser Trp Pro Ser Ile Val Ala Thr Gly Gly Thr
            20                  25                  30

Thr


<210> SEQ ID NO 40
<211> LENGTH: 33
<212> TYPE: PRT
<213> ORGANISM: Athelia rolfsii-Aspergillus niger
<220> FEATURE:
<221> NAME/KEY: MISC_FEATURE
<222> LOCATION: (1)..(33)
<223> OTHER INFORMATION: fusion junction at position 24

<400> SEQUENCE: 40

Gly Val Ser Thr Ser Cys Ser Thr Gly Ala Thr Ser Pro Gly Gly Ser
1               5                   10                  15

Ser Gly Ser Val Glu Val Thr Pro Ser Ile Val Ala Thr Gly Gly Thr
            20                  25                  30

Thr


<210> SEQ ID NO 41
<211> LENGTH: 33
<212> TYPE: PRT
<213> ORGANISM: Talaromyces emersonii-Aspergillus niger
<220> FEATURE:
<221> NAME/KEY: MISC_FEATURE
<222> LOCATION: (1)..(33)
<223> OTHER INFORMATION: fusion junction point at position 7

<400> SEQUENCE: 41
```

-continued

```
Ser Val Pro Ala Val Cys Ala Ala Thr Ser Ala Ile Gly Thr Tyr Ser
1               5                   10                  15

Ser Val Thr Val Thr Ser Trp Pro Ser Ile Val Ala Thr Gly Gly Thr
            20                  25                  30

Thr


<210> SEQ ID NO 42
<211> LENGTH: 33
<212> TYPE: PRT
<213> ORGANISM: Talaromyces emersonii-Aspergillus niger
<220> FEATURE:
<221> NAME/KEY: MISC_FEATURE
<222> LOCATION: (1)..(33)
<223> OTHER INFORMATION: fusion junction at position 16

<400> SEQUENCE: 42

Ser Val Pro Ala Val Cys Ser Ala Thr Ser Ala Thr Gly Pro Tyr Ser
1               5                   10                  15

Ser Val Thr Val Thr Ser Trp Pro Ser Ile Val Ala Thr Gly Gly Thr
            20                  25                  30

Thr


<210> SEQ ID NO 43
<211> LENGTH: 33
<212> TYPE: PRT
<213> ORGANISM: Talaromyces emersonii-Aspergillus niger
<220> FEATURE:
<221> NAME/KEY: MISC_FEATURE
<222> LOCATION: (1)..(33)
<223> OTHER INFORMATION: fusion junction at 24

<400> SEQUENCE: 43

Ser Val Pro Ala Val Cys Ser Ala Thr Ser Ala Thr Gly Pro Tyr Ser
1               5                   10                  15

Thr Ala Thr Asn Thr Val Trp Pro Ser Ile Val Ala Thr Gly Gly Thr
            20                  25                  30

Thr


<210> SEQ ID NO 44
<211> LENGTH: 33
<212> TYPE: PRT
<213> ORGANISM: Talaromyces emersonii-Athelia rolfsii
<220> FEATURE:
<221> NAME/KEY: MISC_FEATURE
<222> LOCATION: (1)..(33)
<223> OTHER INFORMATION: fusion junction at position 9

<400> SEQUENCE: 44

Ser Ser Val Pro Ala Val Cys Ser Thr Gly Ala Thr Ser Pro Gly Gly
1               5                   10                  15

Ser Ser Gly Ser Val Glu Val Thr Phe Asp Val Tyr Ala Thr Thr Val
            20                  25                  30

Tyr


<210> SEQ ID NO 45
<211> LENGTH: 33
<212> TYPE: PRT
<213> ORGANISM: Talaromyces emersonii-Athelia rolfsii
<220> FEATURE:
<221> NAME/KEY: MISC_FEATURE
<222> LOCATION: (1)..(33)
<223> OTHER INFORMATION: fusion junction at position 18
```

-continued

<400> SEQUENCE: 45

Ser Ser Val Pro Ala Val Cys Ser Ala Thr Ser Ala Thr Gly Pro Tyr
1               5                   10                  15

Ser Ser Gly Ser Val Glu Val Thr Phe Asp Val Tyr Ala Thr Thr Val
            20                  25                  30

Tyr

<210> SEQ ID NO 46
<211> LENGTH: 33
<212> TYPE: PRT
<213> ORGANISM: Talaromyces emersonii-Athelia rolfsii
<220> FEATURE:
<221> NAME/KEY: MISC_FEATURE
<222> LOCATION: (1)..(33)
<223> OTHER INFORMATION: fusion junction at position 25

<400> SEQUENCE: 46

Ser Ser Val Pro Ala Val Cys Ser Ala Thr Ser Ala Thr Gly Pro Tyr
1               5                   10                  15

Ser Thr Ala Thr Asn Thr Val Trp Phe Asp Val Tyr Ala Thr Thr Val
            20                  25                  30

Tyr

<210> SEQ ID NO 47
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(38)
<223> OTHER INFORMATION: Primer plac102fwd

<400> SEQUENCE: 47
tcgtaagctt caccatgtcg ttccgatctc tactcgcc                             38

<210> SEQ ID NO 48
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: plac102 rev primer

<400> SEQUENCE: 48
acaggtgccg ggcacgctgc tggc                                            24

<210> SEQ ID NO 49
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: pLac102 rev2 primer

<400> SEQUENCE: 49
ggtaccaatg gcagatgtgg ccgc                                            24

-continued

<210> SEQ ID NO 50
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: pLac102 rev3 primer

<400> SEQUENCE: 50
ccacgaggtg acagtcacac tgctg 25

<210> SEQ ID NO 51
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(34)
<223> OTHER INFORMATION: pSteD226 fwd1 primer

<400> SEQUENCE: 51
tgcaaagctt caccatggcg tccctcgttg ctgg 34

<210> SEQ ID NO 52
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: pSteD226 rev1 primer

<400> SEQUENCE: 52
gcagacggca gggacgctgc ttgc 24

<210> SEQ ID NO 53
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: pSteD rev2 primer

<400> SEQUENCE: 53
tgggcccgtg gcagaggtgg cagag 25

<210> SEQ ID NO 54
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: pSteD226 rev3 primer

<400> SEQUENCE: 54
ccagacggtg ttggtagccg tgct 24

```
<210> SEQ ID NO 55
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(40)
<223> OTHER INFORMATION: AR cDNA fwd1 primer

<400> SEQUENCE: 55

aagaaagctt caccatgttt cgttcactcc tggccttggc                         40


<210> SEQ ID NO 56
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: AR cDNA rev1 primer

<400> SEQUENCE: 56

gcaggaggta gagactccct tagca                                         25


<210> SEQ ID NO 57
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: AR cDNA rev2 primer

<400> SEQUENCE: 57

acccgggctt gtagcaccag tcgag                                         25


<210> SEQ ID NO 58
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: AR cDNA rev3 primer

<400> SEQUENCE: 58

agtgacctcg acactacccg aggag                                         25


<210> SEQ ID NO 59
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: pLac fwd2 primer

<400> SEQUENCE: 59

gcaagcagcg tccctgccgt ctgcgcggcc acatctgcca ttggtacc                48
```

-continued

<210> SEQ ID NO 60
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(34)
<223> OTHER INFORMATION: pLac102 rev4 primer

<400> SEQUENCE: 60
tagtatctag atcaccgcca ggtgtcagtc accg 34

<210> SEQ ID NO 61
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pLac102 fwd3 primer

<400> SEQUENCE: 61
ctctgccacc tctgccacgg gcccatacag cagtgtgact gtcacctcg 49

<210> SEQ ID NO 62
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: PLac102 fwd4 primer

<400> SEQUENCE: 62
agcacggcta ccaacaccgt ctggccgagt atcgtggcta ctggcggc 48

<210> SEQ ID NO 63
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pLac102 fwd5 primer

<400> SEQUENCE: 63
tgctaaggga gtctctacct cctgcgcggc cacatctgcc attggtacc 49

<210> SEQ ID NO 64
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pLac102 fwd6 primer

<400> SEQUENCE: 64

```
ctcgactggt gctacaagcc cgggttacag cagtgtgact gtcacctcg                49


<210> SEQ ID NO 65
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pLac102 fwd7 primer

<400> SEQUENCE: 65

ctcgactggt gctacaagcc cgggttacag cagtgtgact gtcacctcg                49


<210> SEQ ID NO 66
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(50)
<223> OTHER INFORMATION: pSteD fwd2 primer

<400> SEQUENCE: 66

tgctaaggga gtctctacct cctgctctgc cacctctgcc acgggcccat               50


<210> SEQ ID NO 67
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(40)
<223> OTHER INFORMATION: pSteD rev4 primer

<400> SEQUENCE: 67

tacctctaga atcgtcactg ccaactatcg tcaagaatgg                          40


<210> SEQ ID NO 68
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pSteD226 fwd3 primer

<400> SEQUENCE: 68

ctcgactggt gctacaagcc cgggttacag cacggctacc aacaccgtc                49


<210> SEQ ID NO 69
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: pSteD226 fwd4 primer

<400> SEQUENCE: 69
```

-continued

```
ctcctcgggt agtgtcgagg tcactccaag ctctggctct ggcagctca                49


<210> SEQ ID NO 70
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(45)
<223> OTHER INFORMATION: pSteD226 fwd5 primer

<400> SEQUENCE: 70

gccagcagcg tgcccggcac ctgttctgcc acctctgcca cgggc                    45


<210> SEQ ID NO 71
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: pSted226 fwd6 primer

<400> SEQUENCE: 71

gcggccacat ctgccattgg tacctacagc acggctacca acaccgtc                 48


<210> SEQ ID NO 72
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: pSteD226 fwd7 primer

<400> SEQUENCE: 72

cagcagtgtg actgtcacct cgtggccaag ctctggctct ggcagctc                 48


<210> SEQ ID NO 73
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: AR cDNA fwd2 primer

<400> SEQUENCE: 73

gcaagcagcg tccctgccgt ctgctcgact ggtgctacaa gcccgggtg                49


<210> SEQ ID NO 74
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: AR cDNA rev4 primer
```

-continued

<400> SEQUENCE: 74
cggccctcta gaatcgtcat taagattcat cccaagtgtc tttttcgg 48

<210> SEQ ID NO 75
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: AR cDNA fwd3 primer

<400> SEQUENCE: 75
ctctgccacc tctgccacgg gcccaggctc ctcgggtagt gtcgaggtc 49

<210> SEQ ID NO 76
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: AR cDNA fwd4 primer

<400> SEQUENCE: 76
agcacggcta ccaacaccgt ctggttcgac gtttacgcta ccacagtat 49

<210> SEQ ID NO 77
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: AR cDNA fwd5 primer

<400> SEQUENCE: 77
gccagcagcg tgcccggcac ctgttcgact ggtgctacaa gcccgggtg 49

<210> SEQ ID NO 78
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: AR cDNA fwd6 primer

<400> SEQUENCE: 78
gcggccacat ctgccattgg taccggctcc tcgggtagtg tcgaggtc 48

<210> SEQ ID NO 79
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: AR cDNA fwd7 primer -continued

<400> SEQUENCE: 79
cagcagtgtg actgtcacct cgtggttcga cgtttacgct accacagtat a 51

<210> SEQ ID NO 80
<211> LENGTH: 1877
<212> TYPE: DNA
<213> ORGANISM: Talaromyces emersonii

<400> SEQUENCE: 80
aagcttcacc atggcgtccc tcgttgctgg cgctctctgc atcctgggcc tgacgcctgc 60
tgcatttgca cgagcgcccg ttgcagcgcg agccaccggt tccctggact cctttctcgc 120
aaccgaaact ccaattgccc tccaaggcgt gctgaacaac atcgggccca atggtgctga 180
tgtggcagga gcaagcgccg gcattgtggt tgccagtccg agcaggagcg acccaaatta 240
tttctactcc tggacacgtg acgcagcgct cacggccaaa tacctcgtcg acgccttcat 300
cgcgggcaac aaggacctag agcagaccat ccagcagtac atcagcgcgc aggcgaaggt 360
gcaaactatc tccaatccgt ccggagattt atccaccggt ggcttaggtg agcccaagtt 420
caatgtgaat gagacggctt ttaccgggcc ctggggtcgt ccacagaggg acggaccagc 480
gttgagagcg acggccctca ttgcgtatgc gaactatctc atcgacaacg gcgaggcttc 540
gactgccgat gagatcatct ggccgattgt ccagaatgat ctgtcctaca tcacccaata 600
ctggaactca tccaccttcg acctctggga agaagtagaa ggatcctcat tcttcacaac 660
cgccgtgcaa caccgcgccc tggtcgaagg caatgcactg gcaacaaggc tgaaccacac 720
gtgctccaac tgcgtctctc aggcccctca ggtcctgtgt ttcctgcagt catactggac 780
cggatcgtat gttctggcca actttggtgg cagcggtcgt tccggcaagg acgtgaattc 840
gattttgggc agcatccaca cctttgatcc cgccggaggc tgtgacgact cgaccttcca 900
gccgtgttcg gcccgtgcct tggcaaatca caaggtggtc accgactcgt tccggagtat 960
ctatgcgatc aactcaggca tcgcagaggg atctgccgtg gcagtcggcc gctaccctga 1020
ggatgtctac cagggcggga acccctggta cctggccaca gcagcggctg cagagcagct 1080
ttacgacgcc atctaccagt ggaagaagat cggctcgata agtatcacgg acgttagtct 1140
gccatttttc caggatatct acccttctgc cgcggtgggc acctataact ctggctccac 1200
gactttcaac gacatcatct cggccgtcca gacgtatggt gatggatatc tgagtattgt 1260
cgagaaatat actccctcag acggctctct taccgaacaa ttctcccgta cagacggcac 1320
tccgctttct gcctctgccc tgacttggtc gtacgcttct ctcctaaccg cttcggcccg 1380
cagacagtcc gtcgtccctg cttcctgggg cgaaagctcc gcaagcagcg tccctgccgt 1440
ctgctctgcc acctctgcca cgggcccata cagcacggct accaacaccg tctggccaag 1500
ctctggctct ggcagctcaa caaccaccag tagcgcccca tgcaccactc ctacctctgt 1560
ggctgtgacc ttcgacgaaa tcgtcagcac cagttacggg gagacaatct acctggccgg 1620
ctcgatcccc gagctgggca actggtccac ggccagcgcg atccccctcc gcgcggatgc 1680
ttacaccaac agcaacccgc tctggtacgt gaccgtcaat ctgcccccctg gcaccagctt 1740 cgagtacaag ttcttcaaga accagacgga cgggaccatc gtctgggagg acgacccgaa 1800
ccggtcgtac acggtcccag cgtactgtgg gcagactacc gccattcttg acgatagttg 1860
gcagtgacga ttctaga 1877

<210> SEQ ID NO 81

-continued

<211> LENGTH: 1920
<212> TYPE: DNA
<213> ORGANISM: Aspergillus niger

<400> SEQUENCE: 81
atgtcgttcc gatctctact cgccctgagc ggcctcgtct gcacagggtt ggcaaatgtg 60
atttccaagc gcgcgacctt ggattcatgg ttgagcaacg aagcgaccgt ggctcgtact 120
gccatcctga ataacatcgg ggcggacggt gcttgggtgt cgggcgcgga ctctggcatt 180
gtcgttgcta gtcccagcac ggataacccg gactacttct acacctggac tcgcgactct 240
ggtctcgtcc tcaagaccct cgtcgatctc ttccgaaatg gagataccag tctcctctcc 300
accattgaga actacatctc cgcccaggca attgtccagg gtatcagtaa cccctctggt 360
gatctgtcca gcggcgctgg tctcggtgaa cccaagttca atgtcgatga gactgcctac 420
actggttctt ggggacggcc gcagcgagat ggtccggctc tgagagcaac tgctatgatc 480
ggcttcgggc agtggctgct tgacaatggc tacaccagca ccgcaacgga cattgtttgg 540
cccctcgtta ggaacgacct gtcgtatgtg gctcaatact ggaaccagac aggatatgat 600
ctctgggaag aagtcaatgg ctcgtctttc tttacgattg ctgtgcaaca ccgcgccctt 660
gtcgaaggta gtgccttcgc gacggccgtc ggctcgtcct gctcctggtg tgattctcag 720
gcacccgaaa ttctctgcta cctgcagtcc ttctggaccg gcagcttcat tctggccaac 780
ttcgatagca gccgttccgg caaggacgca aacaccctcc tgggaagcat ccacaccttt 840
gatcctgagg ccgcatgcga cgactccacc ttccagccct gctccccgcg cgcgctcgcc 900
aaccacaagg aggttgtaga ctctttccgc tcaatctata ccctcaacga tggtctcagt 960
gacagcgagg ctgttgcggt gggtcggtac cctgaggaca cgtactacaa cggcaacccg 1020
tggttcctgt gcaccttggc tgccgcagag cagttgtacg atgctctata ccagtgggac 1080
aagcaggggt cgttggaggt cacagatgtg tcgctggact tcttcaaggc actgtacagc 1140
gatgctgcta ctggcaccta ctcttcgtcc agttcgactt atagtagcat tgtagatgcc 1200
gtgaagactt tcgccgatgg cttcgtctct attgtggaaa ctcacgccgc aagcaacggc 1260
tccatgtccg agcaatacga caagtctgat ggcgagcagc tttccgctcg cgacctgacc 1320
tggtcttatg ctgctctgct gaccgccaac aaccgtcgta actccgtcgt gcctgcttct 1380
tggggcgaga cctctgccag cagcgtgccc ggcacctgtg cggccacatc tgccattggt 1440
acctacagca gtgtgactgt cacctcgtgg ccgagtatcg tggctactgg cggcaccact 1500
acgacggcta cccccactgg atccggcagc gtgacctcga ccagcaagac caccgcgact 1560
gctagcaaga ccagcaccag tacgtcatca acctcctgta ccactcccac cgccgtggct 1620
gtgactttcg atctgacagc taccaccacc tacggcgaga acatctacct ggtcggatcg 1680
atctctcagc tgggtgactg ggaaaccagc gacggcatag ctctgagtgc tgacaagtac 1740
acttccagcg acccgctctg gtatgtcact gtgactctgc cggctggtga gtcgtttgag 1800
tacaagttta tccgcattga gagcgatgac tccgtggagt gggagagtga tcccaaccga 1860
gaatacaccg ttcctcaggc gtgcggaacg tcgaccgcga cggtgactga cacctggcgg 1920

<210> SEQ ID NO 82
<211> LENGTH: 1954
<212> TYPE: DNA
<213> ORGANISM: Aspergillus niger-Talaromyces hybrid DNA

<400> SEQUENCE: 82
aagcttcacc atggcgtccc tcgttgctgg cgctctctgc atcctgggcc tgacgcctgc 60

-continued

```
tgcatttgca cgagcgcccg ttgcagcgcg agccaccggt tccctggact cctttctcgc    120
aaccgaaact ccaattgccc tccaaggcgt gctgaacaac atcgggccca atggtgctga    180
tgtggcagga gcaagcgccg gcattgtggt tgccagtccg agcaggagcg acccaaatta    240
tttctactcc tggacacgtg acgcagcgct cacggccaaa tacctcgtcg acgccttcat    300
cgcgggcaac aaggacctag agcagaccat ccagcagtac atcagcgcgc aggcgaaggt    360
gcaaactatc tccaatccgt ccggagattt atccaccggt ggcttaggtg agcccaagtt    420
caatgtgaat gagacggctt ttaccgggcc ctggggtcgt ccacagaggg acggaccagc    480
gttgagagcg acggccctca ttgcgtatgc gaactatctc atcgacaacg gcgaggcttc    540
gactgccgat gagatcatct ggccgattgt ccagaatgat ctgtcctaca tcacccaata    600
ctggaactca tccaccttcg acctctggga agaagtagaa ggatcctcat tcttcacaac    660
cgccgtgcaa caccgcgccc tggtcgaagg caatgcactg gcaacaaggc tgaaccacac    720
gtgctccaac tgcgtctctc aggcccctca ggtcctgtgt ttcctgcagt catactggac    780
cggatcgtat gttctggcca actttggtgg cagcggtcgt tccggcaagg acgtgaattc    840
gattttgggc agcatccaca cctttgatcc cgccggaggc tgtgacgact cgaccttcca    900
gccgtgttcg gcccgtgcct tggcaaatca caaggtggtc accgactcgt tccggagtat    960
ctatgcgatc aactcaggca tcgcagaggg atctgccgtg gcagtcggcc gctaccctga   1020
ggatgtctac cagggcggga acccctggta cctggccaca gcagcggctg cagagcagct   1080
ttacgacgcc atctaccagt ggaagaagat cggctcgata agtatcacgg acgttagtct   1140
gccatttttc caggatatct acccttctgc cgcggtgggc acctataact ctggctccac   1200
gactttcaac gacatcatct cggccgtcca gacgtatggt gatggatatc tgagtattgt   1260
cgagaaatat actccctcag acggctctct taccgaacaa ttctcccgta cagacggcac   1320
tccgctttct gcctctgccc tgacttggtc gtacgcttct ctcctaaccg cttcggcccg   1380
cagacagtcc gtcgtccctg cttcctgggg cgaaagctcc gcaagcagcg tccctgccgt   1440
ctgcgcggcc acatctgcca ttggtaccta cagcagtgtg actgtcacct cgtggccgag   1500
tatcgtggct actggcggca ccactacgac ggctaccccc actggatccg gcagcgtgac   1560
ctcgaccagc aagaccaccg cgactgctag caagaccagc accagtacgt catcaacctc   1620
ctgtaccact cccaccgccg tggctgtgac tttcgatctg acagctacca ccacctacgg   1680
cgagaacatc tacctggtcg gatcgatctc tcagctgggt gactgggaaa ccagcgacgg   1740
catagctctg agtgctgaca agtacacttc cagcgacccg ctctggtatg tcactgtgac   1800
tctgccggct ggtgagtcgt ttgagtacaa gtttatccgc attgagagcg atgactccgt   1860
ggagtgggag agtgatccca accgagaata caccgttcct caggcgtgcg gaacgtcgac   1920
cgcgacggtg actgacacct ggcggtgatc taga                               1954
```

<210> SEQ ID NO 83
<211> LENGTH: 1954
<212> TYPE: DNA
<213> ORGANISM: Aspergillus niger-Talaromyces emersonii

<400> SEQUENCE: 83

```
aagcttcacc atggcgtccc tcgttgctgg cgctctctgc atcctgggcc tgacgcctgc     60
tgcatttgca cgagcgcccg ttgcagcgcg agccaccggt tccctggact cctttctcgc    120
aaccgaaact ccaattgccc tccaaggcgt gctgaacaac atcgggccca atggtgctga    180
```

-continued tgtggcagga gcaagcgccg gcattgtggt tgccagtccg agcaggagcg acccaaatta 240
tttctactcc tggacacgtg acgcagcgct cacggccaaa tacctcgtcg acgccttcat 300
cgcgggcaac aaggacctag agcagaccat ccagcagtac atcagcgcgc aggcgaaggt 360
gcaaactatc tccaatccgt ccggagattt atccaccggt ggcttaggtg agcccaagtt 420
caatgtgaat gagacggctt ttaccgggcc ctggggtcgt ccacagaggg acggaccagc 480
gttgagagcg acggccctca ttgcgtatgc gaactatctc atcgacaacg gcgaggcttc 540
gactgccgat gagatcatct ggccgattgt ccagaatgat ctgtcctaca tcacccaata 600
ctggaactca tccaccttcg acctctggga agaagtagaa ggatcctcat tcttcacaac 660
cgccgtgcaa caccgcgccc tggtcgaagg caatgcactg gcaacaaggc tgaaccacac 720
gtgctccaac tgcgtctctc aggcccctca ggtcctgtgt ttcctgcagt catactggac 780
cggatcgtat gttctggcca actttggtgg cagcggtcgt tccggcaagg acgtgaattc 840
gattttgggc agcatccaca cctttgatcc cgccggaggc tgtgacgact cgaccttcca 900
gccgtgttcg gcccgtgcct tggcaaatca caaggtggtc accgactcgt tccggagtat 960
ctatgcgatc aactcaggca tcgcagaggg atctgccgtg gcagtcggcc gctaccctga 1020
ggatgtctac cagggcggga acccctggta cctggccaca gcagcggctg cagagcagct 1080
ttacgacgcc atctaccagt ggaagaagat cggctcgata agtatcacgg acgttagtct 1140
gccatttttc caggatatct acccttctgc cgcggtgggc acctataact ctggctccac 1200
gactttcaac gacatcatct cggccgtcca gacgtatggt gatggatatc tgagtattgt 1260
cgagaaatat actccctcag acggctctct taccgaacaa ttctcccgta cagacggcac 1320
tccgctttct gcctctgccc tgacttggtc gtacgcttct ctcctaaccg cttcggcccg 1380
cagacagtcc gtcgtccctg cttcctgggg cgaaagctcc gcaagcagcg tccctgccgt 1440
ctgctctgcc acctctgcca cgggcccata cagcagtgtg actgtcacct cgtggccgag 1500
tatcgtggct actggcggca ccactacgac ggctaccccc actggatccg gcagcgtgac 1560
ctcgaccagc aagaccaccg cgactgctag caagaccagc accagtacgt catcaacctc 1620
ctgtaccact cccaccgccg tggctgtgac tttcgatctg acagctacca ccacctacgg 1680
cgagaacatc tacctggtcg gatcgatctc tcagctgggt gactgggaaa ccagcgacgg 1740
catagctctg agtgctgaca agtacacttc cagcgacccg ctctggtatg tcactgtgac 1800
tctgccggct ggtgagtcgt ttgagtacaa gtttatccgc attgagagcg atgactccgt 1860
ggagtgggag agtgatccca accgagaata caccgttcct caggcgtgcg gaacgtcgac 1920
cgcgacggtg actgacacct ggcggtgatc taga 1954

<210> SEQ ID NO 84
<211> LENGTH: 1954
<212> TYPE: DNA
<213> ORGANISM: Aspergillus niger-Talaromyces emersonii

<400> SEQUENCE: 84
aagcttcacc atggcgtccc tcgttgctgg cgctctctgc atcctgggcc tgacgcctgc 60
tgcatttgca cgagcgcccg ttgcagcgcg agccaccggt tccctggact cctttctcgc 120
aaccgaaact ccaattgccc tccaaggcgt gctgaacaac atcgggccca atggtgctga 180
tgtggcagga gcaagcgccg gcattgtggt tgccagtccg agcaggagcg acccaaatta 240
tttctactcc tggacacgtg acgcagcgct cacggccaaa tacctcgtcg acgccttcat 300
cgcgggcaac aaggacctag agcagaccat ccagcagtac atcagcgcgc aggcgaaggt 360

-continued gcaaactatc tccaatccgt ccggagattt atccaccggt ggcttaggtg agcccaagtt 420
caatgtgaat gagacggctt ttaccgggcc ctggggtcgt ccacagaggg acggaccagc 480
gttgagagcg acggccctca ttgcgtatgc gaactatctc atcgacaacg gcgaggcttc 540
gactgccgat gagatcatct ggccgattgt ccagaatgat ctgtcctaca tcacccaata 600
ctggaactca tccaccttcg acctctggga agaagtagaa ggatcctcat tcttcacaac 660
cgccgtgcaa caccgcgccc tggtcgaagg caatgcactg gcaacaaggc tgaaccacac 720
gtgctccaac tgcgtctctc aggcccctca ggtcctgtgt ttcctgcagt catactggac 780
cggatcgtat gttctggcca actttggtgg cagcggtcgt tccggcaagg acgtgaattc 840
gattttgggc agcatccaca cctttgatcc cgccggaggc tgtgacgact cgaccttcca 900
gccgtgttcg gcccgtgcct tggcaaatca caaggtggtc accgactcgt tccggagtat 960
ctatgcgatc aactcaggca tcgcagaggg atctgccgtg gcagtcggcc gctaccctga 1020
ggatgtctac cagggcggga acccctggta cctggccaca gcagcggctg cagagcagct 1080
ttacgacgcc atctaccagt ggaagaagat cggctcgata agtatcacgg acgttagtct 1140
gccatttttc caggatatct acccttctgc cgcggtgggc acctataact ctggctccac 1200
gactttcaac gacatcatct cggccgtcca gacgtatggt gatggatatc tgagtattgt 1260
cgagaaatat actccctcag acggctctct taccgaacaa ttctcccgta cagacggcac 1320
tccgctttct gcctctgccc tgacttggtc gtacgcttct ctcctaaccg cttcggcccg 1380
cagacagtcc gtcgtccctg cttcctgggg cgaaagctcc gcaagcagcg tccctgccgt 1440
ctgctctgcc acctctgcca cgggcccata cagcacggct accaacaccg tctggccgag 1500
tatcgtggct actggcggca ccactacgac ggctaccccc actggatccg gcagcgtgac 1560
ctcgaccagc aagaccaccg cgactgctag caagaccagc accagtacgt catcaacctc 1620
ctgtaccact cccaccgccg tggctgtgac tttcgatctg acagctacca ccacctacgg 1680
cgagaacatc tacctggtcg gatcgatctc tcagctgggt gactgggaaa ccagcgacgg 1740
catagctctg agtgctgaca agtacacttc cagcgacccg ctctggtatg tcactgtgac 1800
tctgccggct ggtgagtcgt ttgagtacaa gtttatccgc attgagagcg atgactccgt 1860
ggagtgggag agtgatccca accgagaata caccgttcct caggcgtgcg gaacgtcgac 1920
cgcgacggtg actgacacct ggcggtgatc taga 1954

<210> SEQ ID NO 85
<211> LENGTH: 1927
<212> TYPE: DNA
<213> ORGANISM: Aspergillus niger-Athelia rolfsii

<400> SEQUENCE: 85
aagcttcacc atgtttcgtt cactcctggc cttggctgcg tgtgcagtcg cctctgtatc 60
tgcacagtct gcgtctgcga cagcatatct taccaaggaa tctgcagttg ccaagaatgg 120
cgtactttgc aacattggta gccagggatg catgtctgag ggtgcctata gcggtattgt 180
gatcgcatct ccctctaaaa ctagccctga ctatctctat acctggactc gcgactcgtc 240
gctcgtcttc aagatgttaa ttgaccaata cacaaatggc ctggatacga cactgcgcac 300
tctcattgac gagtttgtct ctgcggaagc caccattcaa caaaccagta actcatctgg 360
taccgtctct accggtggtc tcggcgaacc caaattcaat atcgacgaga cggcatttac 420
gggcgcatgg ggtcgtcccc aacgtgatgg tcccgccctc cgtgcaaccg caatcatgac 480

-continued

```
ctatgcgacg tatctgtaca acaatggcaa cacttcctac gtgaccaaca ccctttggcc    540

tatcatcaag ctcgaccttg actatgtcaa ctcggactgg aaccagacca cgtttgacct    600

ctgggaagaa gttgactcgt cttctttctt tacgactgcc gttcagcacc gtgctcttgt    660

tcagggcgca gcctttgcta ccctcatcgg ccaaacttcg tctgcttcga cttactccgc    720

cacggcccct agcattctct gcttcttgca gtcttactgg aacaccaacg gatactggac    780

ggccaacact ggtggcggac gttccggcaa ggacgccaac accatactcg cttctatcca    840

cacatttgac gccagcgccg gctgctctgc tgccacgtct caaccatgct ctgacgtagc    900

attggccaac ctgaaggtat acgttgactc tttccgtagt atttatacga tcaacagcgg    960

tatttcctct acctcgggtg ttgctactgg tcgctacccc gaagattcgt attacaatgg   1020

caacccctgg tacctctgca cactcgccgt cgccgagcag ctctatgatg ctctcatcgt   1080

atggaaggct gccggggagc tcaacgtcac ctccgtctcg ctcgcgttct tccagcaatt   1140

cgactcgagc atcaccgccg gcacttacgc ctcctcgtcg agcgtataca cttcgctcat   1200

ctctgacatc caggcgttcg cagacgagtt tgttgacatt gttgccaagt acacgccttc   1260

gtctggcttc ttgtctgagc agtatgataa gtccacgggt gctcaggatt cggctgctaa   1320

cttgacttgg tcctatgctg ctgctatcac cgcttaccaa gcccgcaatg gcttcacagg   1380

tgcttcgtgg ggtgctaagg gagtctctac ctcctgcgcg gccacatctg ccattggtac   1440

ctacagcagt gtgactgtca cctcgtggcc gagtatcgtg gctactggcg gcaccactac   1500

gacggctacc cccactggat ccggcagcgt gacctcgacc agcaagacca ccgcgactgc   1560

tagcaagacc agcaccagta cgtcatcaac ctcctgtacc actcccaccg ccgtggctgt   1620

gactttcgat ctgacagcta ccaccaccta cggcgagaac atctacctgg tcggatcgat   1680

ctctcagctg ggtgactggg aaaccagcga cggcatagct ctgagtgctg acaagtacac   1740

ttccagcgac ccgctctggt atgtcactgt gactctgccg gctggtgagt cgtttgagta   1800

caagtttatc cgcattgaga gcgatgactc cgtggagtgg gagagtgatc ccaaccgaga   1860

atacaccgtt cctcaggcgt gcggaacgtc gaccgcgacg gtgactgaca cctggcggtg   1920

atctaga                                                              1927
```

<210> SEQ ID NO 86
<211> LENGTH: 1927
<212> TYPE: DNA
<213> ORGANISM: Aspergillus niger-Athelia rolfsii

<400> SEQUENCE: 86

```
aagcttcacc atgtttcgtt cactcctggc cttggctgcg tgtgcagtcg cctctgtatc     60

tgcacagtct gcgtctgcga cagcatatct taccaaggaa tctgcagttg ccaagaatgg    120

cgtactttgc aacattggta gccagggatg catgtctgag ggtgcctata gcggtattgt    180

gatcgcatct ccctctaaaa ctagccctga ctatctctat acctggactc gcgactcgtc    240

gctcgtcttc aagatgttaa ttgaccaata cacaaatggc ctggatacga cactgcgcac    300

tctcattgac gagtttgtct ctgcggaagc caccattcaa caaaccagta actcatctgg    360

taccgtctct accggtggtc tcggcgaacc caaattcaat atcgacgaga cggcatttac    420

gggcgcatgg ggtcgtcccc aacgtgatgg tcccgccctc cgtgcaaccg caatcatgac    480

ctatgcgacg tatctgtaca acaatggcaa cacttcctac gtgaccaaca ccctttggcc    540

tatcatcaag ctcgaccttg actatgtcaa ctcggactgg aaccagacca cgtttgacct    600

ctgggaagaa gttgactcgt cttctttctt tacgactgcc gttcagcacc gtgctcttgt    660
```

-continued

```
tcagggcgca gcctttgcta ccctcatcgg ccaaacttcg tctgcttcga cttactccgc    720
cacggcccct agcattctct gcttcttgca gtcttactgg aacaccaacg gatactggac    780
ggccaacact ggtggcggac gttccggcaa ggacgccaac accatactcg cttctatcca    840
cacatttgac gccagcgccg gctgctctgc tgccacgtct caaccatgct ctgacgtagc    900
attggccaac ctgaaggtat acgttgactc tttccgtagt atttatacga tcaacagcgg    960
tatttcctct acctcgggtg ttgctactgg tcgctacccc gaagattcgt attacaatgg   1020
caacccctgg tacctctgca cactcgccgt cgccgagcag ctctatgatg ctctcatcgt   1080
atggaaggct gccggggagc tcaacgtcac ctccgtctcg ctcgcgttct tccagcaatt   1140
cgactcgagc atcaccgccg gcacttacgc ctcctcgtcg agcgtataca cttcgctcat   1200
ctctgacatc caggcgttcg cagacgagtt tgttgacatt gttgccaagt acacgccttc   1260
gtctggcttc ttgtctgagc agtatgataa gtccacgggt gctcaggatt cggctgctaa   1320
cttgacttgg tcctatgctg ctgctatcac cgcttaccaa gcccgcaatg gcttcacagg   1380
tgcttcgtgg ggtgctaagg gagtttctac ctcctgctcg actggtgcta caagcccggg   1440
ttacagcagt gtgactgtca cctcgtggcc gagtatcgtg gctactggcg gcaccactac   1500
gacggctacc cccactggat ccggcagcgt gacctcgacc agcaagacca ccgcgactgc   1560
tagcaagacc agcaccagta cgtcatcaac ctcctgtacc actcccaccg ccgtggctgt   1620
gactttcgat ctgacagcta ccaccaccta cggcgagaac atctacctgg tcggatcgat   1680
ctctcagctg ggtgactggg aaaccagcga cggcatagct ctgagtgctg acaagtacac   1740
ttccagcgac ccgctctggt atgtcactgt gactctgccg gctggtgagt cgtttgagta   1800
caagtttatc cgcattgaga gcgatgactc cgtggagtgg gagagtgatc ccaaccgaga   1860
atacaccgtt cctcaggcgt gcggaacgtc gaccgcgacg gtgactgaca cctggcggtg   1920
atctaga                                                             1927
```

<210> SEQ ID NO 87
<211> LENGTH: 1927
<212> TYPE: DNA
<213> ORGANISM: Aspergillus niger-Athelia rolfsii

<400> SEQUENCE: 87

```
aagcttcacc atgtttcgtt cactcctggc cttggctgcg tgtgcagtcg cctctgtatc     60
tgcacagtct gcgtctgcga cagcatatct taccaaggaa tctgcagttg ccaagaatgg    120
cgtactttgc aacattggta gccagggatg catgtctgag ggtgcctata gcggtattgt    180
gatcgcatct ccctctaaaa ctagccctga ctatctctat acctggactc gcgactcgtc    240
gctcgtcttc aagatgttaa ttgaccaata cacaaatggc ctggatacga cactgcgcac    300
tctcattgac gagtttgtct ctgcggaagc caccattcaa caaaccagta actcatctgg    360
taccgtctct accggtggtc tcggcgaacc caaattcaat atcgacgaga cggcatttac    420
gggcgcatgg ggtcgtcccc aacgtgatgg tcccgccctc cgtgcaaccg caatcatgac    480
ctatgcgacg tatctgtaca acaatggcaa cacttcctac gtgaccaaca ccctttggcc    540
tatcatcaag ctcgaccttg actatgtcaa ctcggactgg aaccagacca cgtttgacct    600
ctgggaagaa gttgactcgt cttctttctt tacgactgcc gttcagcacc gtgctcttgt    660
tcagggcgca gcctttgcta ccctcatcgg ccaaacttcg tctgcttcga cttactccgc    720
cacggcccct agcattctct gcttcttgca gtcttactgg aacaccaacg gatactggac    780
```

-continued

```
ggccaacact ggtggcggac gttccggcaa ggacgccaac accatactcg cttctatcca    840

cacatttgac gccagcgccg gctgctctgc tgccacgtct caaccatgct ctgacgtagc    900

attggccaac ctgaaggtat acgttgactc tttccgtagt atttatacga tcaacagcgg    960

tatttcctct acctcgggtg ttgctactgg tcgctacccc gaagattcgt attacaatgg   1020

caacccctgg tacctctgca cactcgccgt cgccgagcag ctctatgatg ctctcatcgt   1080

atggaaggct gccggggagc tcaacgtcac ctccgtctcg ctcgcgttct tccagcaatt   1140

cgactcgagc atcaccgccg gcacttacgc ctcctcgtcg agcgtataca cttcgctcat   1200

ctctgacatc caggcgttcg cagacgagtt tgttgacatt gttgccaagt acacgccttc   1260

gtctggcttc ttgtctgagc agtatgataa gtccacgggt gctcaggatt cggctgctaa   1320

cttgacttgg tcctatgctg ctgctatcac cgcttaccaa gcccgcaatg gcttcacagg   1380

tgcttcgtgg ggtgctaagg gagtttctac ctcctgctcg actggtgcta caagcccggg   1440

tggctcctcg ggtagtgtcg aggtcactcc gagtatcgtg gctactggcg gcaccactac   1500

gacggctacc cccactggat ccggcagcgt gacctcgacc agcaagacca ccgcgactgc   1560

tagcaagacc agcaccagta cgtcatcaac ctcctgtacc actcccaccg ccgtggctgt   1620

gactttcgat ctgacagcta ccaccaccta cggcgagaac atctacctgg tcggatcgat   1680

ctctcagctg ggtgactggg aaaccagcga cggcatagct ctgagtgctg acaagtacac   1740

ttccagcgac ccgctctggt atgtcactgt gactctgccg gctggtgagt cgtttgagta   1800

caagtttatc cgcattgaga gcgatgactc cgtggagtgg gagagtgatc ccaaccgaga   1860

atacaccgtt cctcaggcgt gcggaacgtc gaccgcgacg gtgactgaca cctggcggtg   1920

atctaga                                                             1927
```

```
<210> SEQ ID NO 88
<211> LENGTH: 1850
<212> TYPE: DNA
<213> ORGANISM: Athelia rolfsii-Talaromyces emersonii

<400> SEQUENCE: 88

aagcttcacc atgtttcgtt cactcctggc cttggctgcg tgtgcagtcg cctctgtatc     60

tgcacagtct gcgtctgcga cagcatatct taccaaggaa tctgcagttg ccaagaatgg    120

cgtactttgc aacattggta gccagggatg catgtctgag ggtgcctata gcggtattgt    180

gatcgcatct ccctctaaaa ctagccctga ctatctctat acctggactc gcgactcgtc    240

gctcgtcttc aagatgttaa ttgaccaata cacaaatggc ctggatacga cactgcgcac    300

tctcattgac gagtttgtct ctgcggaagc caccattcaa caaaccagta actcatctgg    360

taccgtctct accggtggtc tcggcgaacc caaattcaat atcgacgaga cggcatttac    420

gggcgcatgg ggtcgtcccc aacgtgatgg tcccgccctc cgtgcaaccg caatcatgac    480

ctatgcgacg tatctgtaca acaatggcaa cacttcctac gtgaccaaca ccctttggcc    540

tatcatcaag ctcgaccttg actatgtcaa ctcggactgg aaccagacca cgtttgacct    600

ctgggaagaa gttgactcgt cttctttctt tacgactgcc gttcagcacc gtgctcttgt    660

tcagggcgca gcctttgcta ccctcatcgg ccaaacttcg tctgcttcga cttactccgc    720

cacggcccct agcattctct gcttcttgca gtcttactgg aacaccaacg gatactggac    780

ggccaacact ggtggcggac gttccggcaa ggacgccaac accatactcg cttctatcca    840

cacatttgac gccagcgccg gctgctctgc tgccacgtct caaccatgct ctgacgtagc    900

attggccaac ctgaaggtat acgttgactc tttccgtagt atttatacga tcaacagcgg    960
```

-continued tatttcctct acctcgggtg ttgctactgg tcgctacccc gaagattcgt attacaatgg 1020
caacccctgg tacctctgca cactcgccgt cgccgagcag ctctatgatg ctctcatcgt 1080
atggaaggct gccggggagc tcaacgtcac ctccgtctcg ctcgcgttct tccagcaatt 1140
cgactcgagc atcaccgccg gcacttacgc ctcctcgtcg agcgtataca cttcgctcat 1200
ctctgacatc caggcgttcg cagacgagtt tgttgacatt gttgccaagt acacgccttc 1260
gtctggcttc ttgtctgagc agtatgataa gtccacgggt gctcaggatt cggctgctaa 1320
cttgacttgg tcctatgctg ctgctatcac cgcttaccaa gcccgcaatg gcttcacagg 1380
tgcttcgtgg ggtgctaagg gagtctctac ctcctgctct gccacctctg ccacgggccc 1440
atacagcacg gctaccaaca ccgtctggcc aagctctggc tctggcagct caacaaccac 1500
cagtagcgcc ccatgcacca ctcctacctc tgtggctgtg accttcgacg aaatcgtcag 1560
caccagttac ggggagacaa tctacctggc cggctcgatc cccgagctgg gcaactggtc 1620
cacggccagc gcgatccccc tccgcgcgga tgcttacacc aacagcaacc cgctctggta 1680
cgtgaccgtc aatctgcccc ctggcaccag cttcgagtac aagttcttca agaaccagac 1740
ggacgggacc atcgtctggg aggacgaccc gaaccggtcg tacacggtcc cagcgtactg 1800
tgggcagact accgccattc ttgacgatag ttggcagtga cgattctaga 1850

<210> SEQ ID NO 89
<211> LENGTH: 3110
<212> TYPE: DNA
<213> ORGANISM: Athelia rolfsii-Talaromyces emersonii

<400> SEQUENCE: 89
aagcttcacc atgtttcgtt cactcctggc cttggctgcg tgtgcagtcg cctctgtatc 60
tgcacagtct gcgtctgcga cagcatatct taccaaggaa tctgcagttg ccaagaatgg 120
cgtactttgc aacattggta gccagggatg catgtctgag ggtgcctata gcggtattgt 180
gatcgcatct ccctctaaaa ctagccctga ctatctctat acctggactc gcgactcgtc 240
gctcgtcttc aagatgttaa ttgaccaata cacaaatggc ctggatacga cactgcgcac 300
tctcattgac gagtttgtct ctgcggaagc caccattcaa caaaccagta actcatctgg 360
taccgtctct accggtggtc tcggcgaacc caaattcaat atcgacgaga cggcatttac 420
gggcgcatgg ggtcgtcccc aacgtgatgg tcccgccctc cgtgcaaccg caatcatgac 480
ctatgcgacg tatctgtaca acaatggcaa cacttcctac gtgaccaaca cccctttggcc 540 tatcatcaag ctcgaccttg actatgtcaa ctcggactgg aaccagacca cgtttgacct 600
ctgggaagaa gttgactcgt cttctttctt tacgactgcc gttcagcacc gtgctcttgt 660
tcagggcgca gcctttgcta ccctcatcgg ccaaacttcg tctgcttcga cttactccgc 720
cacggcccct agcattctct gcttcttgca gtcttactgg aacaccaacg gatactggac 780
ggccaacact ggtggcggac gttccggcaa ggacgccaac accatactcg cttctatcca 840
cacatttgac gccagcgccg gctgctctgc tgccacgtct caaccatgct ctgacgtagc 900
attggccaac ctgaaggtat acgttgactc tttccgtagt atttatacga tcaacagcgg 960
tatttcctct acctcgggtg ttgctactgg tcgctacccc gaagattcgt attacaatgg 1020
caacccctgg tacctctgca cactcgccgt cgccgagcag ctctatgatg ctctcatcgt 1080
atggaaggct gccggggagc tcaacgtcac ctccgtctcg ctcgcgttct tccagcaatt 1140
cgactcgagc atcaccgccg gcacttacgc ctcctcgtcg agcgtataca cttcgctcat 1200

-continued

```
ctctgacatc caggcgttcg cagacgagtt tgttgacatt gttgccaagt acacgccttc   1260

aagcttcacc atgtttcgtt cactcctggc cttggctgcg tgtgcagtcg cctctgtatc   1320

tgcacagtct gcgtctgcga cagcatatct taccaaggaa tctgcagttg ccaagaatgg   1380

cgtactttgc aacattggta gccagggatg catgtctgag ggtgcctata gcggtattgt   1440

gatcgcatct ccctctaaaa ctagccctga ctatctctat acctggactc gcgactcgtc   1500

gctcgtcttc aagatgttaa ttgaccaata cacaaatggc ctggatacga cactgcgcac   1560

tctcattgac gagtttgtct ctgcggaagc caccattcaa caaaccagta actcatctgg   1620

taccgtctct accggtggtc tcggcgaacc caaattcaat atcgacgaga cggcatttac   1680

gggcgcatgg ggtcgtcccc aacgtgatgg tcccgccctc cgtgcaaccg caatcatgac   1740

ctatgcgacg tatctgtaca acaatggcaa cacttcctac gtgaccaaca ccctttggcc   1800

tatcatcaag ctcgaccttg actatgtcaa ctcggactgg aaccagacca cgtttgacct   1860

ctgggaagaa gttgactcgt cttctttctt tacgactgcc gttcagcacc gtgctcttgt   1920

tcagggcgca gcctttgcta ccctcatcgg ccaaacttcg tctgcttcga cttactccgc   1980

cacggcccct agcattctct gcttcttgca gtcttactgg aacaccaacg gatactggac   2040

ggccaacact ggtggcggac gttccggcaa ggacgccaac accatactcg cttctatcca   2100

cacatttgac gccagcgccg gctgctctgc tgccacgtct caaccatgct ctgacgtagc   2160

attggccaac ctgaaggtat acgttgactc tttccgtagt atttatacga tcaacagcgg   2220

tatttcctct acctcgggtg ttgctactgg tcgctacccc gaagattcgt attacaatgg   2280

caacccctgg tacctctgca cactcgccgt cgccgagcag ctctatgatg ctctcatcgt   2340

atggaaggct gccggggagc tcaacgtcac ctccgtctcg ctcgcgttct tccagcaatt   2400

cgactcgagc atcaccgccg gcacttacgc ctcctcgtcg agcgtataca cttcgctcat   2460

ctctgacatc caggcgttcg cagacgagtt tgttgacatt gttgccaagt acacgccttc   2520

gtctggcttc ttgtctgagc agtatgataa gtccacgggt gctcaggatt cggctgctaa   2580

cttgacttgg tcctatgctg ctgctatcac cgcttaccaa gcccgcaatg gcttcacagg   2640

tgcttcgtgg ggtgctaagg gagtttctac ctcctgctcg actggtgcta caagcccggg   2700

ttacagcacg gctaccaaca ccgtctggcc aagctctggc tctggcagct caacaaccac   2760

cagtagcgcc ccatgcacca ctcctacctc tgtggctgtg accttcgacg aaatcgtcag   2820

caccagttac ggggagacaa tctacctggc cggctcgatc cccgagctgg gcaactggtc   2880

cacggccagc gcgatccccc tccgcgcgga tgcttacacc aacagcaacc cgctctggta   2940

cgtgaccgtc aatctgcccc ctggcaccag cttcgagtac aagttcttca agaaccagac   3000

ggacgggacc atcgtctggg aggacgaccc gaaccggtcg tacacggtcc cagcgtactg   3060

tgggcagact accgccattc ttgacgatag ttggcagtga cgattctaga              3110
```

<210> SEQ ID NO 90
<211> LENGTH: 1850
<212> TYPE: DNA
<213> ORGANISM: Athelia rolfsii-Talaromyces emersonii

<400> SEQUENCE: 90

```
aagcttcacc atgtttcgtt cactcctggc cttggctgcg tgtgcagtcg cctctgtatc     60

tgcacagtct gcgtctgcga cagcatatct taccaaggaa tctgcagttg ccaagaatgg    120

cgtactttgc aacattggta gccagggatg catgtctgag ggtgcctata gcggtattgt    180

gatcgcatct ccctctaaaa ctagccctga ctatctctat acctggactc gcgactcgtc    240
```

-continued

```
gctcgtcttc aagatgttaa ttgaccaata cacaaatggc ctggatacga cactgcgcac    300
tctcattgac gagtttgtct ctgcggaagc caccattcaa caaaccagta actcatctgg    360
taccgtctct accggtggtc tcggcgaacc caaattcaat atcgacgaga cggcatttac    420
gggcgcatgg ggtcgtcccc aacgtgatgg tcccgccctc cgtgcaaccg caatcatgac    480
ctatgcgacg tatctgtaca acaatggcaa cacttcctac gtgaccaaca ccctttggcc    540
tatcatcaag ctcgaccttg actatgtcaa ctcggactgg aaccagacca cgtttgacct    600
ctgggaagaa gttgactcgt cttctttctt tacgactgcc gttcagcacc gtgctcttgt    660
tcagggcgca gcctttgcta ccctcatcgg ccaaacttcg tctgcttcga cttactccgc    720
cacggcccct agcattctct gcttcttgca gtcttactgg aacaccaacg gatactggac    780
ggccaacact ggtggcggac gttccggcaa ggacgccaac accatactcg cttctatcca    840
cacatttgac gccagcgccg gctgctctgc tgccacgtct caaccatgct ctgacgtagc    900
attggccaac ctgaaggtat acgttgactc tttccgtagt atttatacga tcaacagcgg    960
tatttcctct acctcgggtg ttgctactgg tcgctacccc gaagattcgt attacaatgg   1020
caacccctgg tacctctgca cactcgccgt cgccgagcag ctctatgatg ctctcatcgt   1080
atggaaggct gccggggagc tcaacgtcac ctccgtctcg ctcgcgttct tccagcaatt   1140
cgactcgagc atcaccgccg gcacttacgc ctcctcgtcg agcgtataca cttcgctcat   1200
ctctgacatc caggcgttcg cagacgagtt tgttgacatt gttgccaagt acacgccttc   1260
gtctggcttc ttgtctgagc agtatgataa gtccacgggt gctcaggatt cggctgctaa   1320
cttgacttgg tcctatgctg ctgctatcac cgcttaccaa gcccgcaatg gcttcacagg   1380
tgcttcgtgg ggtgctaagg gagtttctac ctcctgctcg actggtgcta caagcccggg   1440
tggctcctcg ggtagtgtcg aggtcactcc aagctctggc tctggcagct caacaaccac   1500
cagtagcgcc ccatgcacca ctcctacctc tgtggctgtg accttcgacg aaatcgtcag   1560
caccagttac ggggagacaa tctacctggc cggctcgatc cccgagctgg gcaactggtc   1620
cacggccagc gcgatccccc tccgcgcgga tgcttacacc aacagcaacc cgctctggta   1680
cgtgaccgtc aatctgcccc ctggcaccag cttcgagtac aagttcttca agaaccagac   1740
ggacgggacc atcgtctggg aggacgaccc gaaccggtcg tacacggtcc cagcgtactg   1800
tgggcagact accgccattc ttgacgatag ttggcagtga cgattctaga               1850
```

<210> SEQ ID NO 91
<211> LENGTH: 1862
<212> TYPE: DNA
<213> ORGANISM: Athelia rolfsii-Aspergillus niger

<400> SEQUENCE: 91

```
aagcttcacc atgtcgttcc gatctctact cgccctgagc ggcctcgtct gcacagggtt     60
ggcaaatgtg atttccaagc gcgcgacctt ggattcatgg ttgagcaacg aagcgaccgt    120
ggctcgtact gccatcctga ataacatcgg ggcggacggt gcttgggtgt cgggcgcgga    180
ctctggcatt gtcgttgcta gtcccagcac ggataacccg gactacttct acacctggac    240
tcgcgactct ggtctcgtcc tcaagaccct cgtcgatctc ttccgaaatg gagataccag    300
tctcctctcc accattgaga actacatctc cgcccaggca attgtccagg gtatcagtaa    360
cccctctggt gatctgtcca gcggcgctgg tctcggtgaa cccaagttca atgtcgatga    420
gactgcctac actggttctt ggggacggcc gcagcgagat ggtccggctc tgagagcaac    480
```

-continued

```
tgctatgatc ggcttcgggc agtggctgct tgacaatggc tacaccagca ccgcaacgga    540

cattgtttgg cccctcgtta ggaacgacct gtcgtatgtg gctcaatact ggaaccagac    600

aggatatgat ctctgggaag aagtcaatgg ctcgtctttc tttacgattg ctgtgcaaca    660

ccgcgccctt gtcgaaggta gtgccttcgc gacggccgtc ggctcgtcct gctcctggtg    720

tgattctcag gcacccgaaa ttctctgcta cctgcagtcc ttctggaccg gcagcttcat    780

tctggccaac ttcgatagca gccgttccgg caaggacgca aacaccctcc tgggaagcat    840

ccacaccttt gatcctgagg ccgcatgcga cgactccacc ttccagccct gctccccgcg    900

cgcgctcgcc aaccacaagg aggttgtaga ctctttccgc tcaatctata ccctcaacga    960

tggtctcagt gacagcgagg ctgttgcggt gggtcggtac cctgaggaca cgtactacaa   1020

cggcaacccg tggttcctgt gcaccttggc tgccgcagag cagttgtacg atgctctata   1080

ccagtgggac aagcaggggt cgttggaggt cacagatgtg tcgctggact tcttcaaggc   1140

actgtacagc gatgctgcta ctggcaccta ctcttcgtcc agttcgactt atagtagcat   1200

tgtagatgcc gtgaagactt tcgccgatgg cttcgtctct attgtggaaa ctcacgccgc   1260

aagcaacggc tccatgtccg agcaatacga caagtctgat ggcgagcagc tttccgctcg   1320

cgacctgacc tggtcttatg ctgctctgct gaccgccaac aaccgtcgta actccgtcgt   1380

gcctgcttct tggggcgaga cctctgccag cagcgtgccc ggcacctgtt ctgccacctc   1440

tgccacgggc ccatacagca cggctaccaa caccgtctgg ccaagctctg gctctggcag   1500

ctcaacaacc accagtagcg ccccatgcac cactcctacc tctgtggctg tgaccttcga   1560

cgaaatcgtc agcaccagtt acggggagac aatctacctg gccggctcga tccccgagct   1620

gggcaactgg tccacggcca gcgcgatccc cctccgcgcg gatgcttaca ccaacagcaa   1680

cccgctctgg tacgtgaccg tcaatctgcc ccctggcacc agcttcgagt acaagttctt   1740

caagaaccag acggacggga ccatcgtctg ggaggacgac ccgaaccggt cgtacacggt   1800

cccagcgtac tgtgggcaga ctaccgccat tcttgacgat agttggcagt gacgattcta   1860

ga                                                                  1862
```

```
<210> SEQ ID NO 92
<211> LENGTH: 1862
<212> TYPE: DNA
<213> ORGANISM: Athelia rolfsii-Aspergillus niger

<400> SEQUENCE: 92

aagcttcacc atgtcgttcc gatctctact cgccctgagc ggcctcgtct gcacagggtt     60

ggcaaatgtg atttccaagc gcgcgacctt ggattcatgg ttgagcaacg aagcgaccgt    120

ggctcgtact gccatcctga ataacatcgg ggcggacggt gcttgggtgt cgggcgcgga    180

ctctggcatt gtcgttgcta gtcccagcac ggataacccg gactacttct acacctggac    240

tcgcgactct ggtctcgtcc tcaagaccct cgtcgatctc ttccgaaatg gagataccag    300

tctcctctcc accattgaga actacatctc cgcccaggca attgtccagg gtatcagtaa    360

cccctctggt gatctgtcca gcggcgctgg tctcggtgaa cccaagttca atgtcgatga    420

gactgcctac actggttctt ggggacggcc gcagcgagat ggtccggctc tgagagcaac    480

tgctatgatc ggcttcgggc agtggctgct tgacaatggc tacaccagca ccgcaacgga    540

cattgtttgg cccctcgtta ggaacgacct gtcgtatgtg gctcaatact ggaaccagac    600

aggatatgat ctctgggaag aagtcaatgg ctcgtctttc tttacgattg ctgtgcaaca    660

ccgcgccctt gtcgaaggta gtgccttcgc gacggccgtc ggctcgtcct gctcctggtg    720
```

-continued

```
tgattctcag gcacccgaaa ttctctgcta cctgcagtcc ttctggaccg gcagcttcat    780
tctggccaac ttcgatagca gccgttccgg caaggacgca aacaccctcc tgggaagcat    840
ccacaccttt gatcctgagg ccgcatgcga cgactccacc ttccagccct gctccccgcg    900
cgcgctcgcc aaccacaagg aggttgtaga ctctttccgc tcaatctata ccctcaacga    960
tggtctcagt gacagcgagg ctgttgcggt gggtcggtac cctgaggaca cgtactacaa   1020
cggcaacccg tggttcctgt gcaccttggc tgccgcagag cagttgtacg atgctctata   1080
ccagtgggac aagcaggggt cgttggaggt cacagatgtg tcgctggact tcttcaaggc   1140
actgtacagc gatgctgcta ctggcaccta ctcttcgtcc agttcgactt atagtagcat   1200
tgtagatgcc gtgaagactt tcgccgatgg cttcgtctct attgtggaaa ctcacgccgc   1260
aagcaacggc tccatgtccg agcaatacga caagtctgat ggcgagcagc tttccgctcg   1320
cgacctgacc tggtcttatg ctgctctgct gaccgccaac aaccgtcgta actccgtcgt   1380
gcctgcttct tggggcgaga cctctgccag cagcgtgccc ggcacctgtg cggccacatc   1440
tgccattggt acctacagca cggctaccaa caccgtctgg ccaagctctg gctctggcag   1500
ctcaacaacc accagtagcg ccccatgcac cactcctacc tctgtggctg tgaccttcga   1560
cgaaatcgtc agcaccagtt acggggagac aatctacctg gccggctcga tccccgagct   1620
gggcaactgg tccacggcca gcgcgatccc cctccgcgcg gatgcttaca ccaacagcaa   1680
cccgctctgg tacgtgaccg tcaatctgcc ccctggcacc agcttcgagt acaagttctt   1740
caagaaccag acggacggga ccatcgtctg ggaggacgac ccgaaccggt cgtacacggt   1800
cccagcgtac tgtgggcaga ctaccgccat tcttgacgat agttggcagt gacgattcta   1860
ga                                                                  1862
```

```
<210> SEQ ID NO 93
<211> LENGTH: 1862
<212> TYPE: DNA
<213> ORGANISM: Athelia rolfsii-Aspergillus niger

<400> SEQUENCE: 93

aagcttcacc atgtcgttcc gatctctact cgccctgagc ggcctcgtct gcacagggtt     60
ggcaaatgtg atttccaagc gcgcgacctt ggattcatgg ttgagcaacg aagcgaccgt    120
ggctcgtact gccatcctga ataacatcgg ggcggacggt gcttgggtgt cgggcgcgga    180
ctctggcatt gtcgttgcta gtcccagcac ggataacccg gactacttct acacctggac    240
tcgcgactct ggtctcgtcc tcaagaccct cgtcgatctc ttccgaaatg gagataccag    300
tctcctctcc accattgaga actacatctc cgcccaggca attgtccagg gtatcagtaa    360
cccctctggt gatctgtcca gcggcgctgg tctcggtgaa cccaagttca atgtcgatga    420
gactgcctac actggttctt ggggacggcc gcagcgagat ggtccggctc tgagagcaac    480
tgctatgatc ggcttcgggc agtggctgct tgacaatggc tacaccagca ccgcaacgga    540
cattgtttgg cccctcgtta ggaacgacct gtcgtatgtg gctcaatact ggaaccagac    600
aggatatgat ctctgggaag aagtcaatgg ctcgtctttc tttacgattg ctgtgcaaca    660
ccgcgccctt gtcgaaggta gtgccttcgc gacggccgtc ggctcgtcct gctcctggtg    720
tgattctcag gcacccgaaa ttctctgcta cctgcagtcc ttctggaccg gcagcttcat    780
tctggccaac ttcgatagca gccgttccgg caaggacgca aacaccctcc tgggaagcat    840
ccacaccttt gatcctgagg ccgcatgcga cgactccacc ttccagccct gctccccgcg    900
```

-continued

```
cgcgctcgcc aaccacaagg aggttgtaga ctctttccgc tcaatctata ccctcaacga    960

tggtctcagt gacagcgagg ctgttgcggt gggtcggtac cctgaggaca cgtactacaa   1020

cggcaacccg tggttcctgt gcaccttggc tgccgcagag cagttgtacg atgctctata   1080

ccagtgggac aagcaggggt cgttggaggt cacagatgtg tcgctggact tcttcaaggc   1140

actgtacagc gatgctgcta ctggcaccta ctcttcgtcc agttcgactt atagtagcat   1200

tgtagatgcc gtgaagactt tcgccgatgg cttcgtctct attgtggaaa ctcacgccgc   1260

aagcaacggc tccatgtccg agcaatacga caagtctgat ggcgagcagc tttccgctcg   1320

cgacctgacc tggtcttatg ctgctctgct gaccgccaac aaccgtcgta actccgtcgt   1380

gcctgcttct tggggcgaga cctctgccag cagcgtgccc ggcacctgtg cggccacatc   1440

tgccattggt acctacagca gtgtgactgt cacctcgtgg ccaagctctg gctctggcag   1500

ctcaacaacc accagtagcg ccccatgcac cactcctacc tctgtggctg tgaccttcga   1560

cgaaatcgtc agcaccagtt acggggagac aatctacctg gccggctcga tccccgagct   1620

gggcaactgg tccacggcca gcgcgatccc cctccgcgcg gatgcttaca ccaacagcaa   1680

cccgctctgg tacgtgaccg tcaatctgcc ccctggcacc agcttcgagt acaagttctt   1740

caagaaccag acggacggga ccatcgtctg ggaggacgac ccgaaccggt cgtacacggt   1800

cccagcgtac tgtgggcaga ctaccgccat tcttgacgat agttggcagt gacgattcta   1860

ga                                                                  1862
```

<210> SEQ ID NO 94
<211> LENGTH: 1790
<212> TYPE: DNA
<213> ORGANISM: Talaromyce emersonii-Aspergillus niger

<400> SEQUENCE: 94

```
aagcttcacc atggcgtccc tcgttgctgg cgctctctgc atcctgggcc tgacgcctgc     60

tgcatttgca cgagcgcccg ttgcagcgcg agccaccggt tccctggact cctttctcgc    120

aaccgaaact ccaattgccc tccaaggcgt gctgaacaac atcgggccca atggtgctga    180

tgtggcagga gcaagcgccg gcattgtggt tgccagtccg agcaggagcg acccaaatta    240

tttctactcc tggacacgtg acgcagcgct cacggccaaa tacctcgtcg acgccttcat    300

cgcgggcaac aaggacctag agcagaccat ccagcagtac atcagcgcgc aggcgaaggt    360

gcaaactatc tccaatccgt ccggagattt atccaccggt ggcttaggtg agcccaagtt    420

caatgtgaat gagacggctt ttaccgggcc ctggggtcgt ccacagaggg acggaccagc    480

gttgagagcg acggccctca ttgcgtatgc gaactatctc atcgacaacg gcgaggcttc    540

gactgccgat gagatcatct ggccgattgt ccagaatgat ctgtcctaca tcacccaata    600

ctggaactca tccaccttcg acctctggga agaagtagaa ggatcctcat tcttcacaac    660

cgccgtgcaa caccgcgccc tggtcgaagg caatgcactg gcaacaaggc tgaaccacac    720

gtgctccaac tgcgtctctc aggcccctca ggtcctgtgt ttcctgcagt catactggac    780

cggatcgtat gttctggcca actttggtgg cagcggtcgt tccggcaagg acgtgaattc    840

gattttgggc agcatccaca cctttgatcc cgccggaggc tgtgacgact cgaccttcca    900

gccgtgttcg gcccgtgcct tggcaaatca caaggtggtc accgactcgt tccggagtat    960

ctatgcgatc aactcaggca tcgcagaggg atctgccgtg gcagtcggcc gctaccctga   1020

ggatgtctac cagggcggga acccctggta cctggccaca gcagcggctg cagagcagct   1080

ttacgacgcc atctaccagt ggaagaagat cggctcgata agtatcacgg acgttagtct   1140
```

-continued

```
gccatttttc caggatatct acccttctgc cgcggtgggc acctataact ctggctccac   1200
gactttcaac gacatcatct cggccgtcca gacgtatggt gatggatatc tgagtattgt   1260
cgagaaatat actccctcag acggctctct taccgaacaa ttctcccgta cagacggcac   1320
tccgctttct gcctctgccc tgacttggtc gtacgcttct ctcctaaccg cttcggcccg   1380
cagacagtcc gtcgtccctg cttcctgggg cgaaagctcc gcaagcagcg tccctgccgt   1440
ctgctcgact ggtgctacaa gcccgggtgg ctcctcgggt agtgtcgagg tcactttcga   1500
cgtttacgct accacagtat atggccagaa catctatatc accggtgatg tgagtgagct   1560
cggcaactgg acacccgcca atggtgttgc actctcttct gctaactacc ccacctggag   1620
tgccacgatc gctctccccg ctgacacgac aatccagtac aagtatgtca acattgacgg   1680
cagcaccgtc atctgggagg atgctatcag caatcgcgag atcacgacgc ccgccagcgg   1740
cacatacacc gaaaaagaca cttgggatga atcttaatga cgattctaga              1790
```

<210> SEQ ID NO 95
<211> LENGTH: 1790
<212> TYPE: DNA
<213> ORGANISM: Talaromyce emersonii-Aspergillus niger

<400> SEQUENCE: 95

```
aagcttcacc atggcgtccc tcgttgctgg cgctctctgc atcctgggcc tgacgcctgc     60
tgcatttgca cgagcgcccg ttgcagcgcg agccaccggt tccctggact cctttctcgc    120
aaccgaaact ccaattgccc tccaaggcgt gctgaacaac atcgggccca atggtgctga    180
tgtggcagga gcaagcgccg gcattgtggt tgccagtccg agcaggagcg acccaaatta    240
tttctactcc tggacacgtg acgcagcgct cacggccaaa tacctcgtcg acgccttcat    300
cgcgggcaac aaggacctag agcagaccat ccagcagtac atcagcgcgc aggcgaaggt    360
gcaaactatc tccaatccgt ccggagattt atccaccggt ggcttaggtg agcccaagtt    420
caatgtgaat gagacggctt ttaccgggcc ctggggtcgt ccacagaggg acggaccagc    480
gttgagagcg acggccctca ttgcgtatgc gaactatctc atcgacaacg gcgaggcttc    540
gactgccgat gagatcatct ggccgattgt ccagaatgat ctgtcctaca tcacccaata    600
ctggaactca tccaccttcg acctctggga agaagtagaa ggatcctcat tcttcacaac    660
cgccgtgcaa caccgcgccc tggtcgaagg caatgcactg gcaacaaggc tgaaccacac    720
gtgctccaac tgcgtctctc aggcccctca ggtcctgtgt ttcctgcagt catactggac    780
cggatcgtat gttctggcca actttggtgg cagcggtcgt tccggcaagg acgtgaattc    840
gattttgggc agcatccaca cctttgatcc cgccggaggc tgtgacgact cgaccttcca    900
gccgtgttcg gcccgtgcct tggcaaatca caaggtggtc accgactcgt tccggagtat    960
ctatgcgatc aactcaggca tcgcagaggg atctgccgtg gcagtcggcc gctaccctga   1020
ggatgtctac cagggcggga acccctggta cctggccaca gcagcggctg cagagcagct   1080
ttacgacgcc atctaccagt ggaagaagat cggctcgata agtatcacgg acgttagtct   1140
gccatttttc caggatatct acccttctgc cgcggtgggc acctataact ctggctccac   1200
gactttcaac gacatcatct cggccgtcca gacgtatggt gatggatatc tgagtattgt   1260
cgagaaatat actccctcag acggctctct taccgaacaa ttctcccgta cagacggcac   1320
tccgctttct gcctctgccc tgacttggtc gtacgcttct ctcctaaccg cttcggcccg   1380
cagacagtcc gtcgtccctg cttcctgggg cgaaagctcc gcaagcagcg tccctgccgt   1440
```

-continued

```
ctgctctgcc acctctgcca cgggcccagg ctcctcgggt agtgtcgagg tcactttcga   1500

cgtttacgct accacagtat atggccagaa catctatatc accggtgatg tgagtgagct   1560

cggcaactgg acacccgcca atggtgttgc actctcttct gctaactacc ccacctggag   1620

tgccacgatc gctctccccg ctgacacgac aatccagtac aagtatgtca acattgacgg   1680

cagcaccgtc atctgggagg atgctatcag caatcgcgag atcacgacgc ccgccagcgg   1740

cacatacacc gaaaaagaca cttgggatga atcttaatga cgattctaga              1790
```

<210> SEQ ID NO 96
<211> LENGTH: 1790
<212> TYPE: DNA
<213> ORGANISM: Talaromyce emersonii-Aspergillus niger

<400> SEQUENCE: 96

```
aagcttcacc atggcgtccc tcgttgctgg cgctctctgc atcctgggcc tgacgcctgc     60

tgcatttgca cgagcgcccg ttgcagcgcg agccaccggt tccctggact cctttctcgc    120

aaccgaaact ccaattgccc tccaaggcgt gctgaacaac atcgggccca atggtgctga    180

tgtggcagga gcaagcgccg gcattgtggt tgccagtccg agcaggagcg acccaaatta    240

tttctactcc tggacacgtg acgcagcgct cacggccaaa tacctcgtcg acgccttcat    300

cgcgggcaac aaggacctag agcagaccat ccagcagtac atcagcgcgc aggcgaaggt    360

gcaaactatc tccaatccgt ccggagattt atccaccggt ggcttaggtg agcccaagtt    420

caatgtgaat gagacggctt ttaccgggcc ctggggtcgt ccacagaggg acggaccagc    480

gttgagagcg acggccctca ttgcgtatgc gaactatctc atcgacaacg gcgaggcttc    540

gactgccgat gagatcatct ggccgattgt ccagaatgat ctgtcctaca tcacccaata    600

ctggaactca tccaccttcg acctctggga agaagtagaa ggatcctcat tcttcacaac    660

cgccgtgcaa caccgcgccc tggtcgaagg caatgcactg gcaacaaggc tgaaccacac    720

gtgctccaac tgcgtctctc aggcccctca ggtcctgtgt ttcctgcagt catactggac    780

cggatcgtat gttctggcca actttggtgg cagcggtcgt tccggcaagg acgtgaattc    840

gattttgggc agcatccaca cctttgatcc cgccggaggc tgtgacgact cgaccttcca    900

gccgtgttcg gcccgtgcct tggcaaatca caaggtggtc accgactcgt tccggagtat    960

ctatgcgatc aactcaggca tcgcagaggg atctgccgtg gcagtcggcc gctaccctga   1020

ggatgtctac cagggcggga acccctggta cctggccaca gcagcggctg cagagcagct   1080

ttacgacgcc atctaccagt ggaagaagat cggctcgata agtatcacgg acgttagtct   1140

gccatttttc caggatatct acccttctgc cgcggtgggc acctataact ctggctccac   1200

gactttcaac gacatcatct cggccgtcca gacgtatggt gatggatatc tgagtattgt   1260

cgagaaatat actccctcag acggctctct taccgaacaa ttctcccgta cagacggcac   1320

tccgctttct gcctctgccc tgacttggtc gtacgcttct ctcctaaccg cttcggcccg   1380

cagacagtcc gtcgtccctg cttcctgggg cgaaagctcc gcaagcagcg tccctgccgt   1440

ctgctctgcc acctctgcca cgggcccata cagcacggct accaacaccg tctggttcga   1500

cgtttacgct accacagtat atggccagaa catctatatc accggtgatg tgagtgagct   1560

cggcaactgg acacccgcca atggtgttgc actctcttct gctaactacc ccacctggag   1620

tgccacgatc gctctccccg ctgacacgac aatccagtac aagtatgtca acattgacgg   1680

cagcaccgtc atctgggagg atgctatcag caatcgcgag atcacgacgc ccgccagcgg   1740

cacatacacc gaaaaagaca cttgggatga atcttaatga cgattctaga              1790
```

-continued

<210> SEQ ID NO 97
<211> LENGTH: 1775
<212> TYPE: DNA
<213> ORGANISM: Talaromyce emersonii-Athelia rolfsii

<400> SEQUENCE: 97

```
aagcttcacc atgtcgttcc gatctctact cgccctgagc ggcctcgtct gcacagggtt     60
ggcaaatgtg atttccaagc gcgcgacctt ggattcatgg ttgagcaacg aagcgaccgt    120
ggctcgtact gccatcctga ataacatcgg ggcggacggt gcttgggtgt cgggcgcgga    180
ctctggcatt gtcgttgcta gtcccagcac ggataacccg gactacttct acacctggac    240
tcgcgactct ggtctcgtcc tcaagaccct cgtcgatctc ttccgaaatg gagataccag    300
tctcctctcc accattgaga actacatctc cgcccaggca attgtccagg gtatcagtaa    360
cccctctggt gatctgtcca gcggcgctgg tctcggtgaa cccaagttca atgtcgatga    420
gactgcctac actggttctt ggggacggcc gcagcgagat ggtccggctc tgagagcaac    480
tgctatgatc ggcttcgggc agtggctgct tgacaatggc tacaccagca ccgcaacgga    540
cattgtttgg cccctcgtta ggaacgacct gtcgtatgtg gctcaatact ggaaccagac    600
aggatatgat ctctgggaag aagtcaatgg ctcgtctttc tttacgattg ctgtgcaaca    660
ccgcgccctt gtcgaaggta gtgccttcgc gacggccgtc ggctcgtcct gctcctggtg    720
tgattctcag gcacccgaaa ttctctgcta cctgcagtcc ttctggaccg gcagcttcat    780
tctggccaac ttcgatagca gccgttccgg caaggacgca aacaccctcc tgggaagcat    840
ccacaccttt gatcctgagg ccgcatgcga cgactccacc ttccagccct gctccccgcg    900
cgcgctcgcc aaccacaagg aggttgtaga ctctttccgc tcaatctata ccctcaacga    960
tggtctcagt gacagcgagg ctgttgcggt gggtcggtac cctgaggaca cgtactacaa   1020
cggcaacccg tggttcctgt gcaccttggc tgccgcagag cagttgtacg atgctctata   1080
ccagtgggac aagcaggggt cgttggaggt cacagatgtg tcgctggact tcttcaaggc   1140
actgtacagc gatgctgcta ctggcaccta ctcttcgtcc agttcgactt atagtagcat   1200
tgtagatgcc gtgaagactt tcgccgatgg cttcgtctct attgtggaaa ctcacgccgc   1260
aagcaacggc tccatgtccg agcaatacga caagtctgat ggcgagcagc tttccgctcg   1320
cgacctgacc tggtcttatg ctgctctgct gaccgccaac aaccgtcgta actccgtcgt   1380
gcctgcttct tggggcgaga cctctgccag cagcgtgccc ggcacctgtt cgactggtgc   1440
tacaagcccg ggtggctcct cgggtagtgt cgaggtcact ttcgacgttt acgctaccac   1500
agtatatggc cagaacatct atatcaccgg tgatgtgagt gagctcggca actggacacc   1560
cgccaatggt gttgcactct cttctgctaa ctaccccacc tggagtgcca cgatcgctct   1620
ccccgctgac acgacaatcc agtacaagta tgtcaacatt gacggcagca ccgtcatctg   1680
ggaggatgct atcagcaatc gcgagatcac gacgcccgcc agcggcacat acaccgaaaa   1740
agacacttgg gatgaatctt aatgacgatt ctaga                              1775
```

<210> SEQ ID NO 98
<211> LENGTH: 1775
<212> TYPE: DNA
<213> ORGANISM: Talaromyce emersonii-Athelia rolfsii

<400> SEQUENCE: 98

```
aagcttcacc atgtcgttcc gatctctact cgccctgagc ggcctcgtct gcacagggtt     60
```

-continued

```
ggcaaatgtg atttccaagc gcgcgacctt ggattcatgg ttgagcaacg aagcgaccgt    120

ggctcgtact gccatcctga ataacatcgg ggcggacggt gcttgggtgt cgggcgcgga    180

ctctggcatt gtcgttgcta gtcccagcac ggataacccg gactacttct acacctggac    240

tcgcgactct ggtctcgtcc tcaagaccct cgtcgatctc ttccgaaatg gagataccag    300

tctcctctcc accattgaga actacatctc cgcccaggca attgtccagg gtatcagtaa    360

cccctctggt gatctgtcca gcggcgctgg tctcggtgaa cccaagttca atgtcgatga    420

gactgcctac actggttctt ggggacggcc gcagcgagat ggtccggctc tgagagcaac    480

tgctatgatc ggcttcgggc agtggctgct tgacaatggc tacaccagca ccgcaacgga    540

cattgtttgg cccctcgtta ggaacgacct gtcgtatgtg gctcaatact ggaaccagac    600

aggatatgat ctctgggaag aagtcaatgg ctcgtctttc tttacgattg ctgtgcaaca    660

ccgcgccctt gtcgaaggta gtgccttcgc gacggccgtc ggctcgtcct gctcctggtg    720

tgattctcag gcacccgaaa ttctctgcta cctgcagtcc ttctggaccg gcagcttcat    780

tctggccaac ttcgatagca gccgttccgg caaggacgca aacaccctcc tgggaagcat    840

ccacaccttt gatcctgagg ccgcatgcga cgactccacc ttccagccct gctccccgcg    900

cgcgctcgcc aaccacaagg aggttgtaga ctctttccgc tcaatctata ccctcaacga    960

tggtctcagt gacagcgagg ctgttgcggt gggtcggtac cctgaggaca cgtactacaa   1020

cggcaacccg tggttcctgt gcaccttggc tgccgcagag cagttgtacg atgctctata   1080

ccagtgggac aagcaggggt cgttggaggt cacagatgtg tcgctggact tcttcaaggc   1140

actgtacagc gatgctgcta ctggcaccta ctcttcgtcc agttcgactt atagtagcat   1200

tgtagatgcc gtgaagactt tcgccgatgg cttcgtctct attgtggaaa ctcacgccgc   1260

aagcaacggc tccatgtccg agcaatacga caagtctgat ggcgagcagc tttccgctcg   1320

cgacctgacc tggtcttatg ctgctctgct gaccgccaac aaccgtcgta actccgtcgt   1380

gcctgcttct tggggcgaga cctctgccag cagcgtgccc ggcacctgtg cggccacatc   1440

tgccattggt accggctcct cgggtagtgt cgaggtcact ttcgacgttt acgctaccac   1500

agtatatggc cagaacatct atatcaccgg tgatgtgagt gagctcggca actggacacc   1560

cgccaatggt gttgcactct cttctgctaa ctaccccacc tggagtgcca cgatcgctct   1620

ccccgctgac acgacaatcc agtacaagta tgtcaacatt gacggcagca ccgtcatctg   1680

ggaggatgct atcagcaatc gcgagatcac gacgcccgcc agcggcacat acaccgaaaa   1740

agacacttgg gatgaatctt aatgacgatt ctaga                              1775
```

<210> SEQ ID NO 99
<211> LENGTH: 1775
<212> TYPE: DNA
<213> ORGANISM: Talaromyce emersonii-Athelia rolfsii

<400> SEQUENCE: 99

```
aagcttcacc atgtcgttcc gatctctact cgccctgagc ggcctcgtct gcacagggtt     60

ggcaaatgtg atttccaagc gcgcgacctt ggattcatgg ttgagcaacg aagcgaccgt    120

ggctcgtact gccatcctga ataacatcgg ggcggacggt gcttgggtgt cgggcgcgga    180

ctctggcatt gtcgttgcta gtcccagcac ggataacccg gactacttct acacctggac    240

tcgcgactct ggtctcgtcc tcaagaccct cgtcgatctc ttccgaaatg gagataccag    300

tctcctctcc accattgaga actacatctc cgcccaggca attgtccagg gtatcagtaa    360

cccctctggt gatctgtcca gcggcgctgg tctcggtgaa cccaagttca atgtcgatga    420
```

-continued

```
gactgcctac actggttctt ggggacggcc gcagcgagat ggtccggctc tgagagcaac    480
tgctatgatc ggcttcgggc agtggctgct tgacaatggc tacaccagca ccgcaacgga    540
cattgtttgg cccctcgtta ggaacgacct gtcgtatgtg gctcaatact ggaaccagac    600
aggatatgat ctctgggaag aagtcaatgg ctcgtctttc tttacgattg ctgtgcaaca    660
ccgcgccctt gtcgaaggta gtgccttcgc gacggccgtc ggctcgtcct gctcctggtg    720
tgattctcag gcacccgaaa ttctctgcta cctgcagtcc ttctggaccg gcagcttcat    780
tctggccaac ttcgatagca gccgttccgg caaggacgca aacaccctcc tgggaagcat    840
ccacaccttt gatcctgagg ccgcatgcga cgactccacc ttccagccct gctccccgcg    900
cgcgctcgcc aaccacaagg aggttgtaga ctctttccgc tcaatctata ccctcaacga    960
tggtctcagt gacagcgagg ctgttgcggt gggtcggtac cctgaggaca cgtactacaa   1020
cggcaacccg tggttcctgt gcaccttggc tgccgcagag cagttgtacg atgctctata   1080
ccagtgggac aagcaggggt cgttggaggt cacagatgtg tcgctggact tcttcaaggc   1140
actgtacagc gatgctgcta ctggcaccta ctcttcgtcc agttcgactt atagtagcat   1200
tgtagatgcc gtgaagactt tcgccgatgg cttcgtctct attgtggaaa ctcacgccgc   1260
aagcaacggc tccatgtccg agcaatacga caagtctgat ggcgagcagc tttccgctcg   1320
cgacctgacc tggtcttatg ctgctctgct gaccgccaac aaccgtcgta actccgtcgt   1380
gcctgcttct tggggcgaga cctctgccag cagcgtgccc ggcacctgtg cggccacatc   1440
tgccattggt acctacagca gtgtgactgt cacctcgtgg ttcgacgttt acgctaccac   1500
agtatatggc cagaacatct atatcaccgg tgatgtgagt gagctcggca actggacacc   1560
cgccaatggt gttgcactct cttctgctaa ctaccccacc tggagtgcca cgatcgctct   1620
ccccgctgac acgacaatcc agtacaagta tgtcaacatt gacggcagca ccgtcatctg   1680
ggaggatgct atcagcaatc gcgagatcac gacgcccgcc agcggcacat acaccgaaaa   1740
agacacttgg gatgaatctt aatgacgatt ctaga                              1775
```

HYBRID ENZYMES

CROSS-REFERENCE TO RELATED APPLICATIONS

This application is a division of U.S. patent application Ser. No. 11/490,949, filed Jul. 21, 2006, now U.S. Pat. No. 7,312,055, which is a continuation of U.S. patent application Ser. No. 10/974,508, filed on Oct. 27, 2004, now U.S. Pat. No. 7,129,069, which claims the benefit under 35 U.S.C. 119 of U.S. provisional application No. 60/515,017 filed Oct. 28, 2003, the contents of which are incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates, inter alia, to a hybrid between at least one carbohydrate-binding module ("CBM") and at least the catalytic module (CM) of a glucoamylase. The invention also relates to the use of the hybrid enzyme in a starch process in which granular starch is degraded into sugars, e.g., a syrup, or which may be use as nutrient for yeasts in the production of a fermentation product, such as especially ethanol.

2. Description of Related Art

A large number of processes have been described for converting starch to starch hydrolysates, such as maltose, glucose or specialty syrups, either for use as sweeteners or as precursors for other saccharides such as fructose. Glucose may also be fermented to ethanol or other fermentation products.

Starch is a high molecular-weight polymer consisting of chains of glucose units. It usually consists of about 80% amylopectin and 20% amylose. Amylopectin is a branched polysaccharide in which linear chains of alpha-1,4 D-glucose residues are joined by alpha-1,6 glucosidic linkages.

Amylose is a linear polysaccharide built up of D-glucopyranose units linked together by alpha-1,4 glucosidic linkages. In the case of converting starch into a soluble starch hydrolysate, the starch is depolymerized. The conventional depolymerization process consists of a gelatinization step and two consecutive process steps, namely a liquefaction process and a saccharification process.

Granular starch consists of microscopic granules, which are insoluble in water at room temperature. When an aqueous starch slurry is heated, the granules swell and eventually burst, dispersing the starch molecules into the solution. During this "gelatinzation" process there is a dramatic increase in viscosity. As the solids level is 30-40% in a typical industrial process, the starch has to be thinned or "liquefied" so that it can be handled. This reduction in viscosity is today mostly obtained by enzymatic degradation. During the liquefaction step, the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase or a beta-amylase and optionally a debranching enzyme, such as an isoamylase or a pullulanase, are added and the saccharification process proceeds for about 24 to 72 hours.

Conventional starch conversion processes are very energy consuming due to the different requirements in terms of temperature during the various steps. It is thus desirable to be able to select and/or design enzymes used in the process so that the overall process can be performed without having to gelatinize the starch.

SUMMARY OF THE INVENTION

The invention provides in a first aspect a hybrid enzyme which comprises an amino acid sequence of a catalytic module having glucoamylase activity and an amino acid sequence of a carbohydrate-binding module. The catalytic module may preferably be of fungal, bacterial, or plant origin.

In further aspects the invention provides an isolated DNA sequence encoding the hybrid enzyme of the first aspect, a DNA construct comprising the DNA sequence encoding the hybrid enzyme of the first aspect, an expression vector comprising the DNA sequence encoding the hybrid enzyme of the first aspect, and a host cell transformed with a vector; which host cell is capable of expressing the DNA sequence encoding the hybrid enzyme of the first aspect.

In a final aspect the invention provides processes of producing syrup or a fermentation product from granular starch comprising subjecting the raw starch to an alpha-amylase and a hybrid enzyme having glucoamylase activity of the invention in an aqueous medium. If a fermentation product is desired the process includes the presence of a fermenting organism.

DETAILED DESCRIPTION OF THE INVENTION

Figure 1:
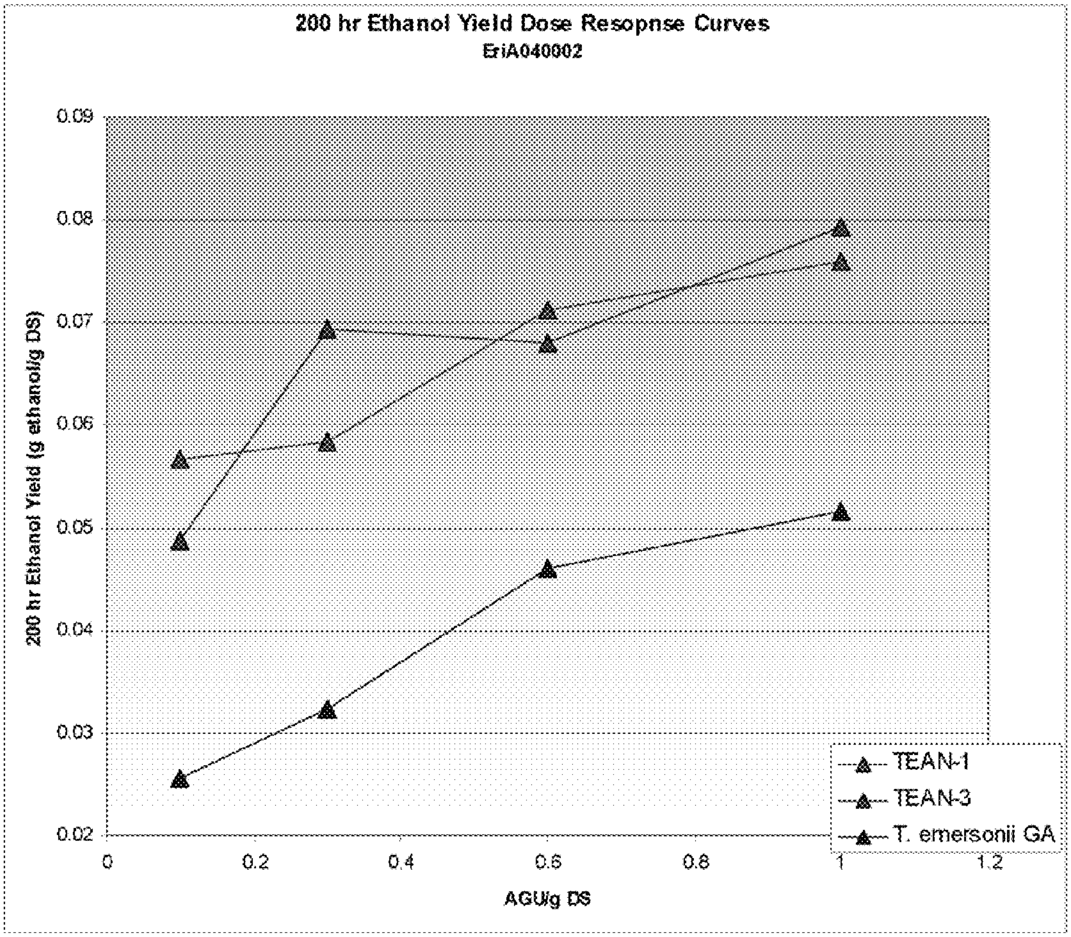
FIG. 1 compares the ethanol yield per g DS of two glycoamylase-SBM (Starch Binding Module) hybrids (TEAN-1 and TEAN-3) comprising the *T. emersonii* catalytic domain and the *A. niger* SBM with wild-type *Talaromyces emersonii* glucoamylase.

The term "granular starch" is understood as raw uncooked starch, i.e., starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "initial gelatinization temperature" is understood as the lowest temperature at which gelatinization of the starch commences. Starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein. S. and Lii. C., Starch/Stärke, Vol. 44 (12) pp. 461-466 (1992).

The term "soluble starch hydrolysate" is understood as the soluble products of the processes of the invention and may comprise mono-, di-, and oligosaccharides, such as glucose, maltose, maltodextrins, cyclodextrins and any mixture of these. Preferably at least 90%, 91%, 92%, 93%, 94%, 95%, 96%, 97%. 98% or at least 99% of the dry solids of the granular starch is converted into a soluble starch hydrolysate.

The term polypeptide "homology" is understood as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for amino acid sequence comparison are used, GAP creation penalty of 3.0 and GAP extension penalty of 0.1.

Hybrid Enzymes

Enzyme classification numbers (EC numbers) referred to in the present specification with claims is in accordance with the Recommendations (1992) of the Nomenclature Committee of the International Union of Biochemistry and Molecular Biology, Academic Press Inc., 1992.

Hybrid enzymes as referred to herein include species comprising an amino acid sequence of a glucoamylase (EC 3.2.1.3) linked (i.e., covalently bound) to an amino acid sequence comprising a carbohydrate-binding module (CBM). The term "carbohydrate-binding module (CBM)" may also be referred to as a "carbohydrate-binding domain (CBD)".

CBM-containing hybrid enzymes, as well as detailed descriptions of the preparation and purification thereof, are known in the art [see, e.g., WO 90/00609, WO 94/24158 and WO 95/16782, as well as Greenwood et al., Biotechnology and Bioengineering 44 (1994) pp. 1295-1305]. They may, e.g., be prepared by transforming into a host cell a DNA construct comprising at least one fragment of DNA encoding the carbohydrate-binding module ligated, with or without a linker, to a DNA sequence encoding the glucoamylase of interest, with or without its own native carbohydrate-binding module, and growing the transformed host cell to express the fused gene. The resulting recombinant product (hybrid enzyme)—often referred to in the art as a "fusion protein"—may be described by the following general formula:

A-CBM-MR-X

In the ratter formula, A-CBM is the N-terminal or the C-terminal region of an amino acid sequence comprising at least the carbohydrate-binding module (CBM) per se. MR is the middle region (the "linker"), and X is the sequence of amino acid residues of a polypeptide encoded by a DNA sequence encoding the enzyme (or other protein) to which the CBM is to be linked.

The moiety A may either be absent (such that A-CBM is a CBM per se, i.e., comprises no amino acid residues other than those constituting the CBM) or may be a sequence of one or more amino acid residues (functioning as a terminal extension of the CBM per se). The linker (MR) may absent, or be a bond, or a short linking group comprising from about 2 to about 100 carbon atoms, in particular of from 2 to 40 carbon atoms. However, MR is preferably a sequence of from about 2 to about 100 amino acid residues, more preferably of from 2 to 40 amino acid residues, such as from 2 to 15 amino acid residues.

The moiety X may constitute either the N-terminal or the C-terminal region of the overall hybrid enzyme.

It will thus be apparent from the above that the CBM in a hybrid enzyme of the type in question may be positioned C-terminally, N-terminally or internally in the hybrid enzyme.

In the embodiment where a CBM is internal in the CBM may be linked via two linkers.

It is to be understood that the hybrid enzyme of the invention may have more than one CBM, such as two or three CBMs. The embodiment where more than one CBM is added is covered: e.g., tandem constructs of two or more CBDs N or C-terminally, a construct having an N-terminal+a C-terminal CBM.

Examples of contemplated hybrids according to the invention therefore also include a hybrid of the following general formulas:

A-CBM1-MR1-X-MR2-CBM2-B

A-CBM1-MR1-B-CBM2-MR2-X

A-CBM1-MR1-CBM2-X-MR3-CBM3-C

The CBM1 and CBM2 may be different or the same. B and C may be either absent (such that, e.g., B-CBM2 is a CBM2 per se, i.e., comprises no amino acid residues other than those constituting the CBM2) or may (as A) be a sequence of one or more amino acid residues (functioning as terminal extensions of the CBM2 per se). Linkers may be absent or present.

Linker Sequence

A linker sequence may be any suitable linker sequence. In preferred embodiments the linker sequence(s) is(are) derived from the *Athelia rolfsii* glucoamylase, the *A. niger* glucoamylase, the *Talaromyces emersonii* glucoamylase, or the *A. kawachii* alpha-amylase. Specific examples of such linker sequences include:

*A. niger* AMG Linker:

```
                                        (SEQ ID NO: 20)
    TGGTTTTATPTGSGSVTSTSKTTATASKTSTSTSSTSA,
```

*A. kawachii* Alpha-Amylase Linker:

```
TTTTTTAAATSTSKATTSSSSSSAAATTSSS,    (SEQ ID NO: 21)
```

*Athelia rolfsii* AMG Linker:

```
    STGATSPGGSSGS,        (SEQ ID NO: 27)
```

PEPT Linker:

```
     PEPTPEPT.          (SEQ ID NO 22)
```

The tinker may also be fragments of the above linkers.

In another preferred embodiment the hybrid enzymes has a linker sequence which differs from the amino acid sequence shown in SEQ ID NO. 20, SEQ ID NO: 21, SEQ ID NO: 27, or SEQ ID NO: 22 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Carbohydrate-Binding Modules (CBM)

A carbohydrate-binding module (CBM) is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules or SBMs (CBMs which may occur in certain amylolytic enzymes, such as certain glucoamylases, or in enzymes such as cyclodextrin glucanotransferases, or in alpha-amylases). Likewise, other subclasses of CBMs would embrace, e.g., cellulose-binding modules (CBMs from cellulolytic enzymes), chitin-binding modules (CBMs which typically occur in chitinases), xylan-binding modules (CBMs which typically occur in xylanases), mannan-binding modules (CBMs which typically occur in mannanases). SBMs are often referred to as SBDs (Starch Binding Domains).

CBMs may be found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and, e.g., one, two or three CBMs, and optionally further comprise one or more polypeptide amino acid sequence regions inking the CBM(s) with the catalytic module(s), a region of the latter type usually being denoted a "linker". Examples of hydrolytic enzymes comprising a CBM—some of which have already been mentioned above—are cellulases, alpha-amylases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g. enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al (1997) in Biotechnol. Lett. 19:1027-1031. The CBM comprises the least 102 amino acids of the polypeptide, i.e. the subsequence from amino acid 582 to amino acid 683. The numbering of Glycoside Hydrolase Families applied in this disclosure follows the concept of Coutinho, P. M. & Henrissat, B. (1999) *CAZy—Carbohydrate-Active Enzymes server* at URL: afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T, Kimura eds., Uni Publishers Co., Tokyo, pp. 15-23, and Bourne, Y. & Henrissat, B, 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the context of the invention. Preferred are CBMs from *Aspergillus* sp., *Athelia* sp., *Talaromyces* sp, *Bacillus* sp., *Klebsiella* sp., or *Rhizopus* sp. Preferred are CBMs of fungal origin. In this connection, techniques suitable for isolating the relevant genes are well known in the art.

Preferred for the invention is CBMs of Carbohydrate-Binding Module Family 20. A "Carbohydrate-Binding Module Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al (1997) in Biotechnol. Lett. 19:1027-1031. The CBM comprises the last 102 amino acids of the polypeptide, i.e., the subsequence from amino acid 582 to amino acid 683. The numbering of CBMs applied in this disclosure follows the concept of Coutinho & Henrissat 1999 (Coutinho, P. M. & Henrissat, B. The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23 or alternatively: Coutinho, P. M. & Henrissat, B. (1999) Carbohydrate-Active Enzymes server at URL: afmb.cnrs-mrs.fr/~cazy/CAZY/index.html).

CBMs of Carbohydrate-Binding Module Family 20 suitable for the invention may be derived from glucoamylases of *Aspergillus amatory* (SWISSPROT Q12537), *Aspergillus kawachii* (SWISSPROT P23176), *Aspergillus niger* (SWISSPROT P04064), *Aspergillus oryzae* (SWISSPROT P36914), from alpha-amylases of *Aspergillus kawachii* (EMBL: #AB008370), *Aspergillus nidulans* (NCBI AAF17100.1), from beta-amylases of *Bacillus cereus* (SWISSPROT P36924), or from CGTases of *Bacillus circulans* (SWISSPROT P43379). Preferred is a CBM from the alpha-amylase of *Aspergillus kawachii* (EMBL:#AB008370) as well as CBMs having at least 50%, 60%, 70%, 80%, 90%, 95%, 97% or even at least 99% homology to the CBM of the alpha-amylase of *Aspergillus kawachii* (EMBL:#AB008370), i.e. a CBM having at least 50%, 60%, 70%, 8:0% 90%, 95%, 97% or even at least 99% homology to the amino acid sequence of SEQ ID NO: 2. Also preferred for the invention are the CBMs of Carbohydrate-Binding Module Family 20 having the amino acid sequences shown in SEQ ID NO: 3 (*Bacillus flavorthermus* CBM), SEQ ID NO: 4 (*Bacillus* sp. CBM), and SEQ ID NO: 5 (*Alcaliphilic Bacillus* CBM). Further preferred CBMs include the CBMs of the glucoamylase from *Hormoconis* sp. such as from *Hormoconis resinae* (Syn. Creosote fungus or *Amorphotheca resinae*) such as the CBM of SWISSPROT:Q03045 (SEQ ID NO: 6), from *Lentinula* sp. such as from *Lentinula edodes* (shiitake mushroom) such as the CBM of SPTREMBL:Q9P4C5 (SEQ ID NO: 7), from *Neurospora* sp. such as from *Neurospora crassa* such as the CBM of SWISSPROT:P14804 (SEQ ID NO: 8), from *Talaromyces* sp. such as from *Talaromyces byssochlamydioides* such as the CBM of NN005220 (SEQ ID NO: 9), from *Geosmithia* sp. such as from *Geosmithia cylindrospora*, such as the CBM of NN48286 (SEQ ID NO: 10), from *Scorias* sp. such as from *Scorias spongiosa* such as the CBM of NN007096 (SEQ ID NO: 11), from *Eupenicillium* sp. such as from *Eupenicillium ludwigii* such as the CBM of NN005968 (SEQ ID NO: 12), from *Aspergillus* sp. such as from *Aspergillus japonicus* such as the CBM of NN001136 (SEQ ID NO:

13), from *Penicillium* sp. such as from *Penicillium cf. miczynskii* such as the CBM of NN48691 (SEQ ID NO: 14), from Mz1 *Penicillium* sp, such as the CBM of NN48690 (SEQ ID NO: 15), from *Thysanophora* sp. such as the CBM of NN48711 (SEQ ID NO: 16), and from *Humicola* sp. such as from *Humicola grisea* var. *thermoidea* such as the CBM of SPTREMBL:Q12623 (SEQ ID NO: 17). Most preferred CBMs include the CBMs of the glucoamylase from *Aspergillus* sp. such as from *Aspergillus niger* such as SEQ ID NO: 18, and *Athelia* sp. such as from *Athelia rolfsii*, such as SEQ ID NO: 19. Also preferred for the invention is any CBD having at least 50%, 60%, 70%, 80%, 90%, 95%, 97% or even at least 99% homology to any of the afore mentioned CBD amino acid sequences.

Further suitable CBMs of Carbohydrate-Binding Module Family 20 may be found on the Carbohydrate-Active Enzymes server at URL: afmb.cnrs-mrs.fr/~cazy/CAZY/index.html).

Other CBM may be found in a glucoamylase from *Mucor circinelloides, Rhizopus oryzae, Arxula adeninivorans.*

Once a nucleotide sequence encoding the substrate-binding (carbohydrate-binding) region has been identified, either as cDNA or chromosomal DNA, it may then be manipulated in a variety of ways to fuse it to a DNA sequence encoding the enzyme of interest. The DNA fragment encoding the carbohydrate-binding amino acid sequence and the DNA encoding the enzyme of interest are then ligated with or without a linker. The resulting ligated DNA may then be manipulated in a variety of ways to achieve expression.

Glucoamylase Sequence

Glucoamylase which are suitable as the basis for CBM/glucoamylase hybrids of the present invention include, e.g., glucoamylase derived from a fungal organism, bacterium or a plant. Preferred glucoamylases are of fungal or bacterial origin, selected from the group consisting of *Aspergillus* glucoamylases, in particular *A. niger* G1 or G2 glucoamylase (Boel et al. (1984), EMBO J. 3 (5), p. 1097-1102) shown in SEQ ID NO: 24), or variants thereof, such as disclosed in WO 92/00381, WO 00/04136 add WO 01/04273 (from Novozymes, Denmark); the *A. awamori* glucoamylase (WO 84/02921), *A. oryzae* (Agric. Biol. Chem. (1991), 55 (4), p. 941-949), or variants or fragments thereof. Other glucoamylases include *Athelia rolfsii* glucoamylase (U.S. Pat. No. 4,727,046) shown in SEQ ID NO. 26, *Talaromyces glucoamylases*, in particular, derived from *Talaromyces emersonii* (WO 99/28448) shown in SEQ ID NO: 25), *Talaromyces leycettanus* (U.S. Pat. No. Re. 32,153), *Talaromyces duponti, Talaromyces thermophilus* (U.S. Pat. No. 4,587,215). Bacterial glucoamylases contemplated include glucoamylases from the genus *Clostridium*, in particular *C. thermoamylolyticum* (EP 135,138), and *C. thermohydrosulfuricum* (WO 86/01831). The glucoamylase may be with or without is native CBM, but comprises at least the catalytic module (CM).

A preferred glucoamylase is the *A. niger* glucoamylase disclosed in SEQ ID NO: 24, or a glucoamylase that has more than 50%, such as 60%, 70%, 80%, 90%. 95%, 96%, 97%, 98% or 99% homology(identity) to the amino acid sequence shown in SEQ ID NO: 24.

It is to be understood that the glucoamylase (catalytic module) may in one embodiment be an active fragment having glucoamylase activity.

Another preferred glucoamylase is the *Athelia rolfsii* glucoamylase shown in SEQ ID NO: 26, or a glucoamylase that has more than 50%, such as 60%, 70%, 80%, 90%, 95%, 96%, 97%, 98% or 99% homology(identity) to the amino acid sequence shown in SEQ ID NO: 26.

A third preferred glucoamylase is the *Talaromyces emersonii* glucoamylase shown in SEQ ID NO: 25, or a glucoamylase that has more than 50%, such as 60%, 70%, 80%, 90%, 95%, 96%, 97%, 98% or 99% homology(identity) to the amino acid sequence shown in SEQ ID NO: 25.

Hybrids

In an aspect the invention relates to a hybrid enzyme which comprises an amino acid sequence of a catalytic module having glucoamylase activity and an amino acid sequence of a carbohydrate-binding module. In a preferred embodiment the catalytic module is of fungal origin. In a more preferred embodiment the catalytic module is derived from a strain of *Talaromyces*, preferably *Talaromyces emersonii*, a strain of *Aspergillus*, preferably *Aspergillus niger* or a strain of *Athelia*, preferably *Athelia rolfsii.*

In a preferred embodiment the hybrid enzyme of the invention comprises a catalytic module having glucoamylase activity derived from *Talaromyces emersonii* and a carbohydrate-binding module from *Aspergillus niger* or *Athelia rolfsii*. The hybrid may in one embodiment include a linker sequence, preferably from *Aspergillus niger, Athelia rolfsii, A. kawachii* or *Talaromyces emersonii* between the catalytic module and the carbohydrate-binding module.

In a preferred embodiment the hybrid enzyme of the invention comprises a catalytic module having glucoamylase activity derived from *Aspergillus niger* and a carbohydrate-binding module from *Athelia rolfsii* or *Talaromyces emersonii*. The hybrid may in one embodiment include a linker sequence, preferably from *Aspergillus niger, Athelia rolfsii, A. kawachii* or *Talaromyces emersonii* between the catalytic module and the carbohydrate-binding module.

In another preferred embodiment the hybrid enzyme of the invention comprises a catalytic module having glucoamylase activity derived from *Athelia rolfsii* and a carbohydrate-binding module from *Aspergillus niger* or *Talaromyces emersonii*. The hybrid may in one embodiment include a linker sequence, preferably from *Aspergillus niger, Athelia rolfsii* or *Talaromyces emersonii* between the catalytic module and the carbohydrate-binding module.

Preferred *Aspergillus niger, Athelia rolfsii* or *Talaromyces emersonii* are the ones shown in SEQ ID NOS: 24, 25, and 26, respectively.

Preferably the hybrid enzyme comprises a CBM sequence having at least 50%, 60%, 70%, 80%, 90%, 95%, 97% or even at least 99% homology to any of the amino acid sequences shown in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SE ID NO: 17, SE ID NO: 18, or SEQ ID NO: 19.

Even more preferred the hybrid enzyme comprises a CBM sequence having an amino acid sequence shown in SEQ ID NO: 28. In yet another preferred embodiment the CBM sequence has an amino acid sequence which differs from the amino acid sequence amino acid sequence shown in SEQ ID NO: 28, or any one of the other CBM sequences, in no more than 10 amino acid positions, no more than 9 positions, no more than 8 positions, no more than 7 positions, no more than 6 positions, no more than 5 positions, no more than 4 positions, no more than 3 positions, no more than 2 positions, or even no more than 1 position. In a most preferred embodiment the hybrid enzyme comprises a CBM derived from a glucoamylase from *Athelia rolfsii*, such as the AMG from *Athelia rolfsii* AHU 9627 described in U.S. Pat. No. 4,727,026 or the CBM from *Aspergillus niger.*

Specific hybrids contemplated according to the invention include the following:

| Fusion | Hybrid Name | CM | SBM | Fusion junction (start of SBM- underlined) |
|---|---|---|---|---|
| SEQ ID NO: 29 | ANTE1 | AN | TE | SSVPGTCSATSATGPYSTATNTVWPSSGSGSST |
| SEQ ID NO: 30 | ANTE2 | AN | TE | SSVPGTCAATSAIGTYSTATNTVWPSSGSGSST |
| SEQ ID NO: 31 | ANTE3 | AN | TE | SSVPGTCAATSAIGTYSSVTVTSWPSSGSGSST |
| SEQ ID NO: 32 | ANAR1 | AN | AR | SSVPGTCSTGATSPGGSSGSVEVTFDVYATTVY |
| SEQ ID NO: 33 | ANAR2 | AN | AR | SSVPGTCAATSAIGTGSSGSVEVTFDVYATTVY |
| SEQ ID NO: 34 | ANAR3 | AN | AR | SSVPGTCAATSAIGTYSSVTVTSWFDVYATTVY |
| SEQ ID NO: 35 | ARTE1 | AR | TE | GVSTSCSATSATGPYSTATNTVWPSSGSGSSTT |
| SEQ ID NO: 36 | ARTE2 | AR | TE | GVSTSCSTGATSPGYSTATNTVWPSSGSGSSTT |
| SEQ ID NO: 37 | ARTE3 | AR | TE | GVSTSCSTGATSPGGSSGSVEVTPSSGSGSSTT |
| SEQ ID NO: 38 | ARAN1 | AR | AN | GVSTSCAATSAIGTYSSVTVTSWPSIVATGGTT |
| SEQ ID NO: 39 | ARAN2 | AR | AN | GVSTSCSTGATSPGYSSVTVTSWPSIVATGGTT |
| SEQ ID NO: 40 | ARAN3 | AR | AN | GVSTSCSTGATSPGGSSGSVEVTPSIVATGGTT |
| SEQ ID NO: 41 | TEAN1 | TE | AN | SVPAVCAATSAIGTYSSVTVTSWPSIVATGGTT |
| SEQ ID NO: 42 | TEAN2 | TE | AN | SVPAVCSATSATGPYSSVTVTSWPSIVATGGTT |
| SEQ ID NO: 43 | TEAN3 | TE | AN | SVPAVCSATSATGPYSTATNTVWPSIVATGGTT |
| SEQ ID NO: 44 | TEAR1 | TE | AR | SSVPAVCSTGATSPGGSSGSVEVTFDVYATTVY |
| SEQ ID NO: 45 | TEAR2 | TE | AR | SSVPAVCSATSATGPYSSGSVEVTFDVYATTVY |
| SEQ ID NO: 46 | TEAR3 | TE | AR | SSVPAVCSATSATGPYSTATNTVWFDVYATTVY |

CM: catalytic module; SBM: starch binding module; AN: *Aspergillus niger;* TE: *Talaromyces emersonii;* AR: *Athelia rolfsii.*

Expression Vectors

The present invention also relates to recombinant expression vectors which may comprise a DNA sequence encoding the hybrid enzyme, a promoter, a signal peptide sequence, and transcriptional and translational stop signals. The various DNA and control sequences described above may be joined together to produce a recombinant expression vector which may include one or more convenient restriction sites to allow for insertion or substitution of the DNA sequence encoding the polypeptide at such sites. Alternatively, the DNA sequence of the present invention may be expressed by inserting the DNA sequence or a DNA construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the DNA sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

Markers

The vectors of the present invention preferably contain one or more selectable markers, which permit easy selection of transformed cents. A selectable marker is a gene the product of which provides for biocide or viral resistance, resistance to heavy metals, prototrophy to auxotrophs, and the like.

Examples of selectable markers for use in a filamentous fungus host cell may be selected from the group including, but not limited to, amdS (acetamidase), argB (omithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus*

*oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the DNA sequence encoding the polypeptide of interest or any other element of the vector for stable integration of the vector into the genome by homologous or none homologous recombination. Alternatively, the vector may contain additional DNA sequences for directing integration by homologous recombination into the genome of the host cell. The additional DNA sequences enable the vector to be integrated into the host cell genome at a precise location(s) in the chromosome(s). To increase the likelihood of integration at a precise location, the integrational elements should preferably contain a sufficient number of DNAs, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding DNA sequences. On the other hand, the vector may be integrated into the genome of the host cell by non-homologous recombination. These DNA sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. The episomal replicating the AMA1 plasmid vector disclosed in WO 00/24883 may be used.

More than one copy of a DNA sequence encoding a polypeptide of interest may be inserted into the host cell to amplify expression of the DNA sequence. Stable amplification of the DNA sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al, 1989, Molecular Cloning, A Laboratory Manual, 2$^{nd}$ edition, Cold Spring Harbor, N.Y.).

Host Cells

The host cell may be of fungal, such as filamentous fungus or yeast origin, or of bacterial origin, such as of *Bacillus* origin.

The host cell of the invention, either comprising a DNA construct or an expression vector comprising the DNA sequence encoding the hybrid enzyme, is advantageously used as a host cell in the recombinant production of the hybrid enzyme. The cell may be transformed with an expression vector. Alternatively, the cell may be transformed with the DNA construct of the invention encoding the hybrid enzyme, conveniently by integrating the DNA construct (in one or more copies) in the host chromosome. Integration of the DNA construct into the host chromosome may be performed according to conventional methods, e.g., by homologous or heterologous recombination.

In a preferred embodiment, the host cell is a filamentous fungus represented by the following groups of *Ascomycota*, include, e.g., *Neurospora, Eupenicillium* (=*Penicillium*), *Emericella* (=*Aspergillus*), *Eurotium* (=*Aspergillus*). In a more preferred embodiment, the filamentous fungus include all filamentous forms of the subdivision *Eumycota* and *Oomycota* (as defined by Hawksworth et al., in, Ainsworth and Bisby's Dictionary of The Fungi, 8$^{th}$ edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

In an even more preferred embodiment, the filamentous fungus host cell is a cell of a species of, but not limited to a cell selected from the group consisting of a strain belonging to a species of *Aspergillus*, preferably *Aspergillus oryzae, Aspergillus niger, Aspergillus awamori, Aspergillus kawachii*, or a strain of *Fusarium*, such as a strain of *Fusarium oxysporium, Fusarium graminearum* (in the perfect state named *Gibberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridoides, Fusarium sambucium, Fusarium roseum*, and *Fusarium roseum* var. *graminearum*), *Fusarium cerealis* (synonym with *Fusarium crookwellense*), or *Fusarium venenatum.*

In a most preferred embodiment, the filamentous fungus host cell is a cell of a strain belonging to a species of *Aspergillus*, preferably *Aspergillus oryzae*, or *Aspergillus niger.*

The host cell may be a wild type filamentous fungus host cell or a variant, a mutant or a genetically modified filamentous fungus host cell. In a preferred embodiment of the invention the host cell is a protease deficient or protease minus strain. Also specifically contemplated is *Aspergillus* strains, such as *Aspergillus niger* strains, genetically modified to disrupt or reduce expression of glucoamylase, acid-stable alpha-amylase, alpha-1,6 transglucosidase, and protease activities.

In another preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred embodiment, the yeast host cell is a Candida, *Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

Transformation of Fungal Host Cells

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156 and WO 96/00787.

Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York, Ito et al., 1983, Journal of Bacteriology 153: 163, and Hinnen et al., 1978, Proceedings of the National Academy of Sciences USA 75; 1920.

Isolating and Cloning a DNA Sequence

The techniques used to isolate or done a DNA sequence encoding a polypeptide of interest are known in the art and include isolation from genomic DNA, preparation from cDNA, or a combination thereof. The cloning of the DNA sequences of the present invention from such genomic DNA can be effected, e.g., by using the welt known polymerase chain reaction (PCR) or antibody screening of expression libraries to detect cloned DNA fragments with shared structural features. See, e.g., Innis et al., 1990, PCR: A Guide to Methods and Application, Academic Press, New York. Other DNA amplification procedures such as ligase chain reaction (LCR), ligated activated transcription (LAT) and DNA sequence-based amplification (NASBA) may be used.

Isolated DNA Sequence

The present invention relates, inter alia, to an isolated DNA sequence comprising a DNA sequence encoding a hybrid enzyme comprising an amino acid sequence of a catalytic module having glucoamylase activity and an amino acid sequence of a carbohydrate-binding module, wherein the catalytic module.

The term "isolated DNA sequence" as used herein refers to a DNA sequence, which is essentially free of other DNA sequences, e.g., at least about 20% pure, preferably at least about 40% pure, more preferably at least about 60% pure, even more preferably at least about 80% pure, and most preferably at least about 90% pure as determined by agarose electrophoresis.

For example, an isolated DNA sequence can be obtained by standard cloning procedures used in genetic engineering to relocate the DNA sequence from its natural location to a different site where it will be reproduced. The cloning procedures may involve excision and isolation of a desired DNA fragment comprising the DNA sequence encoding the polypeptide of interest, insertion of the fragment into a vector molecule, and incorporation of the recombinant vector into a host cell where multiple copies or clones of the DNA sequence will be replicated. An isolated DNA sequence may be manipulated in a variety of ways to provide for expression of the polypeptide of interest. Manipulation of the DNA sequence prior to its insertion into a vector may be desirable or necessary depending on the expression vector. The techniques for modifying DNA sequences utilizing recombinant DNA methods are well known in the art.

DNA Construct

The present invention relates, inter alia, to a DNA construct comprising a DNA sequence encoding a hybrid enzyme comprising an amino acid sequence of a catalytic module having glucoamylase activity and an amino acid sequence of a carbohydrate-binding module. In an embodiment the catalytic module is of fungal origin. "DNA construct" is defined herein as a DNA molecule, either single- or double-stranded, which is isolated from a naturally occurring gene or which has been modified to contain segments of DNA, which are combined and juxtaposed in a manner, which would not otherwise exist in nature. The term DNA construct is synonymous with the term expression cassette when the DNA construct contains all the control sequences required for expression of a coding sequence of the present invention.

Methods of Production

A hybrid of the invention may be produced using any method, for instance, comprising (a) cultivating a host cell under conditions conducive for production of the hybrid; and (b) recovering the hybrid.

In the production methods of the present invention, the cells are cultivated in a nutrient medium suitable for production of the hybrid using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the hybrid to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the hybrid secreted into the nutrient medium, it can be recovered directly from the medium. If the hybrid is not secreted, it can be recovered from cell lysates.

The hybrid may be detected using methods known in the art that are specific for the hybrid. These detection methods may include use of specific antibodies, formation of an enzyme product, or disappearance of an enzyme substrate. For example, an enzyme assay may be used to determine the activity of the hybrid as described herein.

The resulting hybrid may be recovered by methods known in the art. For example, the hybrid may be recovered from the nutrient medium by conventional procedures including, but not limited to, centrifugation, filtration, extraction, spray-drying, evaporation, or precipitation.

The hybrid of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Starch Processing

The hybrid enzyme of the first aspect of the invention may be used in a process for producing syrup or a fermentation product, such as especially ethanol, wherein granular starch is treated in aqueous medium with a hybrid enzyme of the invention having glucoamylase activity. The hybrid enzyme having glucoamylase activity may in an embodiment be added in an amount of 0.02-20 AGU/g DS, preferably 0.1-10 AGU/g DS, such as around 0.1, 0.3, 0.5, 1 or 2 AGU/g DS, such as between 0.1-0.5 AGU/g DS. The granular starch may further be subjected to an alpha-amylase, preferably one disclosed below.

Alpha-Amylase

The alpha-amylase may according to the invention be of any origin. Preferred are alpha-amylases of fungal or bacterial origin. The alpha-amylase may be a *Bacillus* alpha-amylase, such as, derived from a strain of *B. licheniformis, B. amyloliquefaciens, B. stearothermophilus*, and *B. subtilis*. Other alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al. Biochemical and Biophysical Research Communications, 151 (1988), pp. 25-31. Other alpha-amylase variants and hybrids are described in WO 96/23874, WO 97/41213, and WO 99/19467.

Other alpha-amylase includes alpha-amylases derived from a strain of *Aspergillus*, such as, *Aspergillus oryzae* and *Aspergillus niger* alpha-amylases. In a preferred embodiment the alpha-amylase is an acid alpha-amylase. In a more preferred embodiment the acid alpha-amylase is an acid fungal alpha-amylase or an acid bacterial alpha-amylase. More preferably, the acid alpha-amylase is an acid fungal alpha-amylase derived from the genus *Aspergillus*. A commercially available acid fungal amylase is SP288 (available from Novozymes A/S, Denmark). In a preferred embodiment, the alpha-amylase is an acid alpha-amylase. The term “acid alpha-amylase” means an alpha-amylase (E.C. 3.2.1.1) which added in an effective amount has activity at a pH in the range of 3.0 to 7.0, preferably from 3.5 to 6.0, or more preferably from 4.0-5.0. A preferred acid fungal alpha-amylase is a Fungamyl-like alpha-amylase. In the present disclosure, the term “Fungamyl-like alpha-amylase” indicates an alpha-amylase which exhibits a high homology, i.e. more than 50%, 55%, 60%, 65%, 70%, 75%, 80%, 85% 90%, 95%, 96%, 97%, 98%, 99% or even 100% homology(identity) to the amino acid sequence shown in SEQ ID NO: 10 in WO 96/23874.

Preferably the alpha-amylase is an acid alpha-amylase, preferably from the genus *Aspergillus*, preferably of the species *Aspergillus niger*. In a preferred embodiment the acid fungal alpha-amylase is the one from *A. niger* disclosed as “AMYA_ASPNG” in the Swiss-prot/TeEMBL database under the primary accession no. P56271. Also variants of said acid fungal amylase having at least 70% identity, such as at least 80% or even at least 90% identity, such as at least 95%, 96%, 97%, 98%, or at least 99% identity thereto are contemplated.

The amylase may also be a maltogenic alpha-amylase. A “maltogenic alpha-amylase” (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S under the tradename NOVAMYL™. Maltogenic alpha-amylases are described in U.S. Pat. Nos. 4,598,048, 4,604,355 and 6,162,628, which are hereby incorporated by reference. Preferably, the maltogenic alpha-amylase is used in a raw starch hydrolysis process, as described, e.g., in WO 95/10627, which is hereby incorporated by reference.

When the alpha-amylase is used, e.g., as a maltose generating enzyme fungal alpha-amylases may be added in an amount of 0.001-1.0 AFAU/g DS, preferably from 0.002-0.5 AFAU/g DS, preferably 0.02-0.1 AFAU/g DS.

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™. SPEYME FRED, SPEZYME™ AA, and SPEZYME™ DELTA AA (Genencor Int.), and the acid fungal alpha-amylase sold under the trade name SP288 (available from Novozymes A/S, Denmark).

The alpha-amylase may be added in amounts as are well-known in the art. When measured in AAU units the acid alpha-amylase activity is preferably present in an amount of 5-50,0000 AAU/kg of DS, in an amount of 500-50,000 AAU/kg of DS, or more preferably in an amount of 100-10,000 AAU/kg of DS, such as 500-1,000 AAU/kg DS. Fungal acid alpha-amylase are preferably added in an amount of 10-10,000 AFAU/kg of DS, in an amount of 500-2,500 AFAU/kg of DS, or more preferably in an amount of 100-1,000 AFAU/kg of DS, such as approximately 500 AFAU/kg DS.

Process

The process of the invention comprises in one embodiment hydrolysis of a slurry of granular starch, in particular hydrolysis of granular starch into a soluble starch hydrolysate at a temperature below the initial gelatinization temperature of said granular starch.

The granular starch slurry to be subjected to a process of the invention may have 20-55% dry solids granular starch, preferably 25-40% dry solids granular starch, more preferably 30-35% dry solids granular starch.

After being subjected to the process of the seventh aspect of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the granular starch is converted into a soluble starch hydrolysate.

According to the invention the process is conducted at a temperature below the initial gelatinization temperature. Preferably the temperature at which the processes are conducted is between 30-60° C. such as at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or preferably at least 60° C.

The pH at which the process of the seventh aspect of the invention is conducted may in be in the range of 3.0 to 7.0, preferably from 3.5 to 6.0, or more preferably from 4.0-5.0.

The granular starch to be processed in the process of the invention may in particular be obtained from tubers, roots, stems, legumes, cereals or whole grain. More specifically the granular starch may be obtained from corns, cobs, wheat, barley, rye, milo, sago, cassava, tapioca, sorghum, rice, peas, bean, banana or potatoes. Specially contemplated are both waxy and non-waxy types of corn and barley. The granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling the whole kernel is milled and used. Wet milling gives a good separation of germ and meal (starch granules and protein) and is with a few exceptions applied at locations where the starch hydrolysate is used in production of syrups. Both dry and wet milling is well known in the art of starch processing and is equally contemplated for the process of the invention.

Production of a Fermentation Product

In a final aspect the invention relates to the use of the hybrid enzyme having glucoamylase activity in a process for production of a fermentation product especially ethanol. The process comprises subjecting granular starch in aqueous medium to an alpha-amylase and a hybrid enzyme of the invention in the presence of a fermenting organism. The alpha-amylase may be any of the alpha-amylase, preferably one mentioned above. Preferred are acid fungal alpha-amylases, especially of *Aspergillus* origin.

A preferred fermenting organism is yeast. Preferably the process comprises fermenting with yeast carried out simultaneously to the hydrolysis of the granular starch slurry with alpha-amylase and the hybrid enzyme of the invention. The fermentation is performed simultaneous with the hydrolysis the temperature between 30° C. and 35° C., and more preferably between 31° C. and 34° C.

"Fermenting organism" refers to any microorganism suitable for use in a desired fermentation process. Suitable fermenting organisms according to the invention are able to ferment, ire., convert, sugars, such as glucose and/or maltose, directly or indirectly into the desired fermentation product. Examples of fermenting organisms include fungal organisms, such as yeast Preferred yeast includes strains of the *Saccharomyces* spp. and in particular, *Saccharomyces cerevisiae*. Commercially available yeast include, e.g., RED STAR®/Lesaffre Ethanol Red (available from Red Star/Lesaffre, USA), FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Use of a Hybrid of the Invention

In a final aspect the invention relates to the use of a hybrid enzyme of the invention for producing a fermentation product, such as especially ethanol, or syrup, preferably glucoase or maltose. A hybrid of the invention may be used in a process of the invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references and a Sequence Listing are cited herein the disclosures of which are incorporated by reference in their entireties.

Materials and Methods

Yeast:

RED STAR®/Lesaffre Ethanol Red (available from Red Star/Lesaffre, USA)

Acid Stable Alpha-Amylase Activity

When used according to the present invention the activity of any acid stable alpha-amylase may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

$$\underset{\lambda=590\text{ nm}}{\text{STARCH + IODINE}} \xrightarrow[40°, pH\ 2.5]{\text{ALPHA-AMYLASE}} \text{DEXTRINS + OLIGOSACCHARIDES}$$

blue/violet $t = 23$ sec. decoloration

Standard Conditions/Reaction Conditions:

| | |
|---|---|
| Substrate: | Soluble starch, approx. 0.17 g/L |
| Buffer: | Citrate, approx. 0.03 M |
| Iodine (I2): | 0.03 g/L |
| CaCl2: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Glucoamylase Activity

Glucoamylase activity may be measured in AmyloGlucosidase Units (AGU). The AGU is defined as the amount of enzyme, which hydrolyzes 1 micromole maltose per minute under the standard conditions 37° C., pH 4.3, substrate, maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| | |
|---|---|
| AMG incubation: | |
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |
| Color reaction: | |
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference,

DNA Manipulations

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y. Ausubel, F. M. et al. (eds.) "Current protocols in Molecular Biology", John Wiley and Sons, 1995; Harwood, C. R., and Cutting, S. M. (eds.).

EXAMPLES

Example 1

Construction and Expression of Glucoamylase Catalytic Domain-Starch Binding Domain Hybrids Plasmids expressing 18 different AMG hybrids (Table 1) were constructed between the catalytic domains (CD) and starch binding domains (SBD) of glucoamylase from *Aspergillus niger* (AN), *Talaromyces emersonii* (TE), and *Althea rolfsii* (AR). Plasmids were transformed into *Saccharomyces cerevisiae* for expression of recombinant proteins, or the constructed glucoamylase hybrids subsequently were recloned into *Aspergillus niger* expression vector for expression of the hybrid proteins in *A. niger*.

TABLE 1

Fusion junctions in glucoamylase hybrids.

| Fusion | Plasmid name | CD | SBD | Fusion junction (start of SBD- underlined) |
|---|---|---|---|---|
| SEQ ID NO: 29 | pANTE1 | AN | TE | SSVPGTCSATSATGPYSTATNTVWPSSGSGSST |
| SEQ ID NO: 30 | pANTE2 | AN | TE | SSVPGTCAATSAIGTYSTATNTVWPSSGSGSST |
| SEQ ID NO: 31 | pANTE3 | AN | TE | SSVPGTCAATSAIGTYSSVTVTSWPSSGSGSST |
| SEQ ID NO: 32 | pANAR1 | AN | AR | SSVPGTCSTGATSPGGSSGSVEVTFDVYATTVY |
| SEQ ID NO: 33 | pANAR2 | AN | AR | SSVPGTCAATSAIGTGSSGSVEVTFDVYATTVY |
| SEQ ID NO: 34 | pANAR3 | AN | AR | SSVPGTCAATSAIGTYSSVTVTSWFDVYATTVY |
| SEQ ID NO: 35 | pARTE1 | AR | TE | GVSTSCSATSATGPYSTATNTVWPSSGSGSSTT |
| SEQ ID NO: 36 | pARTE2 | AR | TE | GVSTSCSTGATSPGYSTATNTVWPSSGSGSSTT |
| SEQ ID NO: 37 | pARTE3 | AR | TE | GVSTSCSTGATSPGGSSGSVEVTPSSGSGSSTT |
| SEQ ID NO: 38 | pARAN1 | AR | AN | GVSTSCAATSAIGTYSSVTVTSWPSIVATGGTT |
| SEQ ID NO: 39 | pARAN2 | AR | AN | GVSTSCSTGATSPGYSSVTVTSWPSIVATGGTT |
| SEQ ID NO: 40 | pARAN3 | AR | AN | GVSTSCSTGATSPGGSSGSVEVTPSIVATGGTT |
| SEQ ID NO: 41 | pTEAN1 | TE | AN | SVPAVCAATSAIGTYSSVTVTSWPSIVATGGTT |
| SEQ ID NO: 42 | pTEAN2 | TE | AN | SVPAVCSATSATGPYSSVTVTSWPSIVATGGTT |
| SEQ ID NO: 43 | pTEAN3 | TE | AN | SVPAVCSATSATGPYSTATNTVWPSIVATGGTT |
| SEQ ID NO: 44 | pTEAR1 | TE | AR | SSVPAVCSTGATSPGGSSGSVEVTFDVYATTVY |
| SEQ ID NO: 45 | pTEAR2 | TE | AR | SSVPAVCSATSATGPYSSGSVEVTFDVYATTVY |
| SEQ ID NO: 46 | pTEAR3 | TE | AR | SSVPAVCSATSATGPYSTATNTVWFDVYATTVY |

Experimental Procedures

Bacterial and Fungal Strains and Plasmids

*E. coil* DH10B (mcrA (mrr-hsdRMS-mcrBC) 80 dlacZM15 lacX74 deoR recA1endA1 araD139 (ara, leu)7697 galU galK, rpsL nupG), *Saccharomyces cerevisiae* INVSc1 (MATa, his3D1, leu2, trp1-289, ura3-52) and the *E. coli*/yeast plasmid shuttle vector pYES2 were purchased from Invitrogen Inc. (San Diego, Calif.).

DNA Constructions

DNA manipulations were performed essentially as described in Sambrook et al., (1989) Maniatis, T, 1989. Molecular Cloning: A Laboratory Manual (2nd Edition ed.), Cold Spring Harbor Laboratory Press, Cold Spring Harbor, N.Y., and in Dan Burke, Dean Dawson, Tim Stearns (2000) Methods in Yeast Genetics' A Cold Spring Harbor Laboratory Course Manual. Cold Spring Harbor Laboratory. Restriction endonucleases and T4 DNA ligase were from New England Biolabs. Pwo DNA polymerase (Boehringer Mannheim) was used essentially as prescribed by supplier. For SOE pcr reactions app. 100 ng of each desired pcr fragment was gelpurified, mixed together and submitted to 25 cycles of pcr without adding any primers. Reactions were separated by agarose gel electrophoresis and DNA bands migrating at the expected sizes were cut out from the gel, purified by spin columns and used as template in a new pcr reaction using the flanking primers. Plasmid pSteD226 was constructed in two steps; first the coding sequence of the *Talaromyces emersonii* glucoamylase (SEQ ID NO: 80) was cloned as a HindIII-XbaI fragment into pYES2 to create pSteD212. Thereafter the AgeI-HindIII fragment of pSteD212 containing the galactose inducible promoter was replaced with an AgeI-HindIII fragment containing the constitutive TPI promoter (Alber and Kawasaki (1982) Nucleotide sequence of the triose phosphate isomerase gene of *Saccharomyces cerevisiae*. J. Mol. Appl. Gen., 1:419-434) to create pSteD226. Plasmid pLac102 was constructed by cloning the coding sequence of the G1 form of *Aspergillus niger* glucoamylase (SEQ ID NO: 81) into the yeast/*E. coli* shuttle vector pMT742 as an EcoRI-HinDIII fragment. For amplification of CD and SBD's the following DNA templates were employed: plasmid pLAc102 carrying the cDNA encoding the G1-form of *A. niger* G1 glucoamylase; plasmid pSteD226 carrying the cDNA encoding the G1-form of *T. emersonii* glucoamylase; cDNA synthesized from *A. rolfsii* containing the G1-form of *A. rolfsii* glucoamylase.

Oligos utilized to amplify the CD and SBD pcr products are listed in table 2 and Table 3 respectively. SOE PCR products were purified by gel electrophoresis and Qiagen spincolums, digested with HindIII/XbaI and ligated into HindIII/XbaI cut and gel-purified pSteD226. Following ligation overnight reactions were electroporated into DH10B and plated onto LB agar plates supplemented with 100 micro g/ml ampicillin (Sigma). Transformants were plate purified and plasmids extracted for sequencing. Integrity of the entire cloned HindIII-XbaI fragment was verified by restriction analysis and DNA sequencing. Plasmids chosen were then transformed into competent yeast InvScI and plated on selective media. Yeast transformants were purified to single colonies and aliquots stored at −80° C. in 15% glycerol.

TABLE 2

Oligos used to amplify the glucoamylase Catalytic Domains; HinDIII site located in fwd primer underlined; initiator ATG shown in bold.

| Template | Fwd primer (listed 5'-3') | Rev. primer | PCR product |
|---|---|---|---|
| pLac102 | TCGTAAGCTTCACC**ATG**TCGTTCC GATCTCTACTCGCC (SEQ ID NO: 47) | ACAGGTGCCGGGCACGCT GCTGGC (SEQ ID NO: 48) | AN1 |
| pLac102 | TCGTAAGCTTCACC**ATG**TCGTTCC GATCTCTACTCGCC (SEQ ID NO: 48) | GGTACCAATGGCAGATGT GGCCGC (SEQ ID NO: 49) | AN2 |
| pLac102 | TCGTAAGCTTCACC**ATG**TCGTTCC GATCTCTACTCGCC (SEQ ID NO: 48) | CCACGAGGTGACAGTCAC ACTGCTG (SEQ ID NO: 50) | AN3 |
| pSteD226 | TGCAAAGCTTCACC**ATG**GCGTCCC TCGTTGCTGG (SEQ ID NO: 51) | GCAGACGGCAGGGACGCT GCTTGC (SEQ ID NO: 52) | TE1 |
| pSteD226 | TGCAAAGCTTCACC**ATG**GCGTCCC TCGTTGCTGG (SEQ ID NO: 51) | TGGGCCCGTGGCAGAGGT GGCAGAG (SEQ ID NO: 53) | TE2 |
| pSteD226 | TGCAAAGCTTCACC**ATG**GCGTCCC TCGTTGCTGG (SEQ ID NO: 51) | CCAGACGGTGTTGGTAGC CGTGCT (SEQ ID NO: 54) | TE3 |
| AR cDNA | AAGAAAGCTTCACC**ATG**TTTCGTT CACTCCTGGCCTTGGC (SEQ ID NO: 55) | GCAGGAGGTAGAGACTCC CTTAGCA (SEQ ID NO: 56) | AR1 |
| AR cDNA | AAGAAAGCTTCACC**ATG**TTTCGTT CACTCCTGGCCTTGGC (SEQ ID NO: 55) | ACCCGGGCTTGTAGCACC AGTCGAG (SEQ ID NO: 57) | AR2 |
| AR cDNA | AAGAAAGCTTCACC**ATG**TTTCGTT CACTCCTGGCCTTGGC (SEQ ID NO: 55) | AGTGACCTCGACACTACC CGAGGAG (SEQ ID NO: 58) | AR3 |

TABLE 3

Oligos used to amplify the glucoamylase Starch Binding Domains. The XbaI site located at 5'end of the reverse primers are underlined.

| Template | Fwd primer (listed 5'-3') | Reverse primer (listed 5'-3') | PCR product |
|---|---|---|---|
| pLac102 | GCAAGCAGCGTCCCTGCCGTCT GCGCGGCCACATCTGCCATTGG TACC (SEQ ID NO: 59) | TAGTATCTAGATCACCGC CAGGTGTCAGTCACCG (SEQ ID NO: 60) | TEANsbd1 |
| pLac102 | CTCTGCCACCTCTGCCACGGGC CCATACAGCAGTGTGACTGTCA CCTCG (SEQ ID NO: 61) | TAGTATCTAGATCACCGC CAGGTGTCAGTCACCG (SEQ ID NO: 60) | TEANsbd2 |
| pLac102 | AGCACGGCTACCAACACCGTCT GGCCGAGTATCGTGGCTACTGG | TAGTATCTAGATCACCGC CAGGTGTCAGTCACCG | TEANsbd3 |

TABLE 3-continued

Oligos used to amplify the glucoamylase Starch Binding Domains. The XbaI site located at 5'end of the reverse primers are underlined.

| Template | Fwd primer (listed 5'-3') | Reverse primer (listed 5'-3') | PCR product |
|---|---|---|---|
| | CGGC (SEQ ID NO: 62) | (SEQ ID NO: 60) | |
| pLac102 | TGCTAAGGGAGTCTCTACCTCC TGCGCGGCCACATCTGCCATTG GTACC (SEQ ID NO: 63) | TAGTA<u>TCTAGA</u>TCACCGC CAGGTGTCAGTCACCG (SEQ ID NO: 60) | ARANsbd1 |
| pLac102 | CTCGACTGGTGCTACAAGCCCG GGTTACAGCAGTGTGACTGTCA CCTCG (SEQ ID NO: 64) | TAGTA<u>TCTAGA</u>TCACCGC CAGGTGTCAGTCACCG (SEQ ID NO: 60) | ARANsbd2 |
| pLac102 | CTCGACTGGTGCTACAAGCCCG GGTTACAGCAGTGTGACTGTCA CCTCG (SEQ ID NO: 65) | TAGTA<u>TCTAGA</u>TCACCGC CAGGTGTCAGTCACCG (SEQ ID NO: 60) | ARANsbd3 |
| pSteD226 | TGCTAAGGGAGTCTCTACCTCC TGCTCTGCCACCTCTGCCACGG GCCCAT (SEQ ID NO: 66) | TACC<u>TCTAGA</u>ATCGTCAC TGCCAACTATCGTCAAGA AGTT (SEQ ID NO: 67) | ARTEsbd1 |
| pSteD226 | CTCGACTGGTGCTACAAGCCCG GGTTACAGCACGGCTACCAACA CCGTC (SEQ ID NO: 68) | TACC<u>TCTAGA</u>ATCGTCAC TGCCAACTATCGTCAAGA AGTT (SEQ ID NO: 67) | ARTEsbd2 |
| pSteD226 | CTCCTCGGGTAGTGTCGAGGTC ACTCCAAGCTCTGGCTCTGGCA GCTCA (SEQ ID NO: 69) | TACC<u>TCTAGA</u>ATCGTCAC TGCCAACTATCGTCAAGA AGTT (SEQ ID NO: 67) | ARTEsbd3 |
| pSteD226 | GCCAGCAGCGTGCCCGGCACCT GTTCTGCCACCTCTGCCACGGG C (SEQ ID NO: 70) | TACC<u>TCTAGA</u>ATCGTCAC TGCCAACTATCGTCAAGA AGTT (SEQ ID NO: 67) | ANTEsbd1 |
| pSteD226 | GCGGCCACATCTGCCATTGGTA CCTACAGCACGGCTACCAACAC CGTC SEQ ID NO: 71) | TACC<u>TCTAGA</u>ATCGTCAC TGCCAACTATCGTCAAGA AGTT (SEQ ID NO: 67) | ANTEsbd2 |
| pSteD226 | CAGCAGTGTGACTGTCACCTCG TGGCCAAGCTCTGGCTCTGGCA GCTC SEQ ID NO: 72) | TACC<u>TCTAGA</u>ATCGTCAC TGCCAACTATCGTCAAGA AGTT (SEQ ID NO: 67) | ANTEsbd3 |
| AR cDNA | GCAAGCAGCGTCCCTGCCGTCT GCTCGACTGGTGCTACAAGCCC GGGTG (SEQ ID NO: 73) | CGGCCC<u>TCTAGA</u>ATCGTC ATTAAGATTCATCCCAAG TGTCTTTTTCGG (SEQ ID NO: 74) | TEARsbd1 |
| AR cDNA | CTCTGCCACCTCTGCCACGGGC CCAGGCTCCTCGGGTAGTGTCG AGGTC (SEQ ID NO: 75) | CGGCCC<u>TCTAGA</u>ATCGTC ATTAAGATTCATCCCAAG TGTCTTTTTCGG (SEQ ID NO: 67) | TEARsbd2 |
| AR cDNA | AGCACGGCTACCAACACCGTCT GGTTCGACGTTTACGCTACCAC AGTAT (SEQ ID NO: 76) | CGGCCC<u>TCTAGA</u>ATCGTC ATTAAGATTCATCCCAAG TGTCTTTTTCGG (SEQ ID NO: 67) | TEARsbd3 |
| AR cDNA | GCCAGCAGCGTGCCCGGCACCT GTTCGACTGGTGCTACAAGCCC GGGTG (SEQ ID NO: 77) | CGGCCC<u>TCTAGA</u>ATCGTC ATTAAGATTCATCCCAAG TGTCTTTTTCGG (SEQ ID NO: 67) | ANARsbd1 |
| AR cDNA | GCGGCCACATCTGCCATTGGTA CCGGCTCCTCGGGTAGTGTCGA GGTC (SEQ ID NO: 78) | CGGCCC<u>TCTAGA</u>ATCGTC ATTAAGATTCATCCCAAG TGTCTTTTTCGG (SEQ ID NO: 67) | ANARsbd2 |

TABLE 3-continued

Oligos used to amplify the glucoamylase Starch Binding Domains. The XbaI site located at 5'end of the reverse primers are underlined.

| Template | Fwd primer (listed 5'-3') | Reverse primer (listed 5'-3') | PCR product |
|---|---|---|---|
| AR cDNA | CAGCAGTGTGACTGTCACCTCG TGGTTCGACGTTTACGCTACCA CAGTATA (SEQ ID NO: 79) | CGGCCCTCTAGAATCGTC ATTAAGATTCATCCCAAG TGTCTTTTTCGG (SEQ ID NO: 67) | ANARsbd3 |

Fusion of Catalytic Domains and Starch Binding Domains by SOE (Splicing by Overlap Extension) PCR.

SOE PCR, as described in experimental procedures, was employed to generate the desired CD-SBD fusions. PCR products combinations used in the SOS reactions and the resulting SOE hybrids are listed in Table 4.

TABLE 4

SOE pcr reactions.

| CD fragment | SBD product | SOE Hybrid Name | SOE Hybrid |
|---|---|---|---|
| TE1 | TEANsbd1 | ANTE1 | SEQ ID NO: 82 |
| TE2 | TEANsbd2 | ANTE2 | SEQ ID NO: 83 |
| TE3 | TEANsbd3 | ANTE3 | SEQ ID NO: 84 |
| AR1 | ARANsbd1 | ANAR1 | SEQ ID NO: 85 |
| AR2 | ARANsbd2 | ANAR2 | SEQ ID NO: 86 |
| AR3 | ARANsbd3 | ANAR3 | SEQ ID NO: 87 |
| AR1 | ARTEsbd1 | ARTE1 | SEQ ID NO: 88 |
| Ar2 | ARTEsbd2 | ARTE2 | SEQ ID NO: 89 |
| AR3 | ARTEsbd3 | ARTE3 | SEQ ID NO: 90 |
| AN1 | ANTEsbd1 | ARAN1 | SEQ ID NO: 91 |
| AN2 | ANTEsbd2 | ARAN2 | SEQ ID NO: 92 |
| AN3 | ANTEsbd3 | ARAN3 | SEQ ID NO: 93 |
| TE1 | TEARsbd1 | TEAN1 | SEQ ID NO: 94 |
| TE2 | TEARsbd2 | TEAN2 | SEQ ID NO: 95 |
| TE3 | TEARsbd3 | TEAN3 | SEQ ID NO: 96 |
| AN1 | ANARsbd1 | TEAR1 | SEQ ID NO: 97 |
| AN2 | ANARsbd2 | TEAR2 | SEQ ID NO: 98 |
| AN3 | ANARsbd3 | TEAR3 | SEQ ID NO: 99 |

Example 2

Evaluation of Glucoamylase-SBM Hybrids in 'One-Step' Fuel Ethanol Fermentations The relative performance of glucoamylase-SBM hybrids (TEAN-1, TEAN-3) to pure *Talaromyces emersonii* glucoamylase was evaluated via mini-scale fermentations. About 380 g of ground corn (ground in a pilot scale hammer mill through a 1.65 mm screen) was added to about 620 g tap water. This mixture was supplemented with 3 mL 1 g/L penicillin. The pH of this slurry was adjusted to 5.0 with 40% $H_2SO_4$. The dry solid (DS) level was determined in triplicate to be 32%. Approximately 5 g of this slurry was added to 15 mL tubes. Enzymes used in this study are detailed below:

| Enzyme |
|---|
| Purified *T. emersonii* glucoamylase |
| TEAN-1 (*T. emersonii* catalytic module and *A. niger* SBM hybrid) |
| TEAN-3 (*T. emersonii* catalytic module and *A. niger* SBM hybrid) |

A four dose dose-response was conducted with each enzyme. Dosages used were 0.1, 0.3, 0.6 and 1.0 AGU/g DS. Six replicates of each treatment were run.

After dosing the tubes were inoculated with 0.04 mL/g mash of yeast propagate (Red Star™ yeast) that had been grown for 22.5 hours on corn mash. Tubes were capped with a screw on top which had been punctured with a small needle to allow gas release and vortexed briefly before weighing and incubation at 32° C. Fermentation progress was followed by weighing the tubes over time. Tubes were vortexed briefly before weighing. Fermentations were allowed to continue for approximately 200 hours. The result of the experiment is shown in FIG. 1.

It can be seen from FIG. 1 that the two hybrids TEAN-1, TEAN-3 gave a significantly higher ethanol yield per g DS than wild-type *T. emersonii* glucoamylase.

Example 3

Evaluation of Glucoamylase-SBM Hybrids in 'One-Step' Fuel Ethanol Fermentations The relative performance of glucoamylase-SBM hybrids (TEAR-1, TEAR-1) to pure *Talaromyces emersonii* glucoamylase was evaluated via mini-scale fermentations. Approximately 380 g of ground corn (ground in a pilot scale hammer mill through a 1.65 mm screen) was added to about 620 g tap water. This mixture was supplemented with 3 mL 1 g/L penicillin. The pH of this slurry was adjusted to 5 with 40% $H_2SO_4$. The dry solid (DS) level was determined in triplicate to be 32%. Approximately 5 g of this slurry was added to 15 mL tubes. The dose-response was conducted with each enzyme using 0.3 AGU/g DS. After dosing the tubes were inoculated with 0.04 mL/g mash of yeast propagate (RED STAR™ yeast) that had been grown for 22.5 hours on corn mash. Tubes were capped with a screw on top which had been punctured with a small needle to allow gas release and vortexed briefly before weighing and incubation at 32° C. Fermentation progress was followed by weighing the tubes over time. Tubes were vortexed briefly before weighing. Fermentations were allowed to continue for approximately 70 hours. The result of the experiment is shown in Table 1 below:

TABLE 1

| Enzyme | Relative activity |
|---|---|
| Purified *T. emersonii* glucoamylase | 100% |
| TEAR-1 (*T. emersonii* catalytic module and *A. rolfii* SBM hybrid) | 250% |
| TEAR-2 (*T. emersonii* catalytic module and *A. rolfii* SBM hybrid) | 215% |

It can be seen from Table 1 the two hybrids TEAR-1, TEAR-2 have a significantly higher relative activity than wild-type *T. emersonii* glucoamylase.

The invention claimed is:

1. A hybrid enzyme which comprises a catalytic module having glucoamylase activity and a carbohydrate-binding module, wherein:

(a) the catalytic module has at least 90% sequence identity to (i) the sequence of amino acids 1-510 of SEQ ID NO: 24; (ii) the sequence of amino acids 1-483 of SEQ ID NO: 25, or (iii) the amino acid sequence of SEQ ID NO: 26;

(b) the carbohydrate-binding module (i) has at least 90% sequence identity to SEQ ID NO: 2 or SEQ ID NO: 18, or (ii) differs from the amino acid sequence of SEQ ID NO: 28 in no more than 10 amino acid positions.

2. The hybrid enzyme of claim 1, wherein the catalytic module has at least 90% sequence identity to the sequence of amino acids 1-510 of SEQ ID NO: 24 and the carbohydrate domain has at least 90% sequence identity to the amino acid sequence of SEQ ID NO: 2.

3. The hybrid enzyme of claim 1, wherein the catalytic module has at least 90% sequence identity to the sequence of amino acids 1-510 of SEQ ID NO: 24 and the carbohydrate domain has at least 95% sequence identity to the amino acid sequence of SEQ ID NO: 2.

4. The hybrid enzyme of claim 1, wherein the catalytic module has at least 95% sequence identity to the sequence of amino acids 1-510 of SEQ ID NO: 24 and the carbohydrate domain has at least 90% sequence identity to the amino acid sequence of SEQ ID NO: 2.

5. The hybrid enzyme of claim 1, wherein the catalytic module has at least 95% sequence identity to the sequence of amino acids 1-510 of SEQ ID NO: 24 and the carbohydrate domain has at least 95% sequence identity to the amino acid sequence of SEQ ID NO: 2.

6. The hybrid enzyme of claim 1, wherein the catalytic module comprises the sequence of amino acids 1-510 of SEQ ID NO: 24 and the carbohydrate domain comprises the amino acid sequence of SEQ ID NO: 2.

7. The hybrid enzyme of claim 1, wherein the catalytic module has at least 90% sequence identity to the sequence of amino acids 1-510 of SEQ ID NO: 24 and the carbohydrate domain differs from the amino acid sequence of SEQ ID NO: 28 in no more than 10 amino acid positions.

8. The hybrid enzyme of claim 1, wherein the catalytic module has at least 90% sequence identity to the sequence of amino acids 1-510 of SEQ ID NO: 24 and the carbohydrate domain differs from the amino acid sequence of SEQ ID NO: 28 in no more than 5 amino acid positions.

9. The hybrid enzyme of claim 1, wherein the catalytic module has at least 95% sequence identity to the sequence of amino acids 1-510 of SEQ ID NO: 24 and the carbohydrate domain differs from the amino acid sequence of SEQ ID NO: 28 in no more than 10 amino acid positions.

10. The hybrid enzyme of claim 1, wherein the catalytic module has at least 95% sequence identity to the sequence of amino acids 1-510 of SEQ ID NO: 24 and the carbohydrate domain differs from the amino acid sequence of SEQ ID NO: 28 in no more than 5 amino acid positions.

11. The hybrid enzyme of claim 1, wherein the catalytic module comprises the sequence of amino acids 1-510 of SEQ ID NO: 24 and the carbohydrate domain comprises the amino acid sequence of SEQ ID NO: 28.

12. The hybrid enzyme of claim 1, wherein the catalytic module has at least 90% sequence identity to the sequence of amino acids 1-483 of SEQ ID NO: 25 and the carbohydrate domain has at least 90% sequence identity to the amino acid sequence of SEQ ID NO: 2.

13. The hybrid enzyme of claim 1, wherein the catalytic module has at least 90% sequence identity to the sequence of amino acids 1-483 of SEQ ID NO: 25 and the carbohydrate domain has at least 95% sequence identity to the amino acid sequence of SEQ ID NO: 2.

14. The hybrid enzyme of claim 1, wherein the catalytic module has at least 95% sequence identity to the sequence of amino acids 1-483 of SEQ ID NO: 25 and the carbohydrate domain has at least 90% sequence identity to the amino acid sequence of SEQ ID NO: 2.

15. The hybrid enzyme of claim 1, wherein the catalytic module has at least 95% sequence identity to the sequence of amino acids 1-483 of SEQ ID NO: 25 and the carbohydrate domain has at least 95% sequence identity to the amino acid sequence of SEQ ID NO: 2.

16. The hybrid enzyme of claim 1, wherein the catalytic module comprises the sequence of amino acids 1-483 of SEQ ID NO: 25 and the carbohydrate domain comprises the amino acid sequence of SEQ ID NO: 2.

17. The hybrid enzyme of claim 1, wherein the catalytic module has at least 90% sequence identity to the sequence of amino acids 1-483 of SEQ ID NO: 25 and the carbohydrate domain has at least 90% sequence identity to the amino acid sequence of SEQ ID NO: 18.

18. The hybrid enzyme of claim 1, wherein the catalytic module has at least 90% sequence identity to the sequence of amino acids 1-483 of SEQ ID NO: 25 and the carbohydrate domain has at least 95% sequence identity to the amino acid sequence of SEQ ID NO: 18.

19. The hybrid enzyme of claim 1, wherein the catalytic module has at least 95% sequence identity to the sequence of amino acids 1-483 of SEQ ID NO: 25 and the carbohydrate domain has at least 90% sequence identity to the amino acid sequence of SEQ ID NO: 18.

20. The hybrid enzyme of claim 1, wherein the catalytic module has at least 95% sequence identity to the sequence of amino acids 1-483 of SEQ ID NO: 25 and the carbohydrate domain has at least 95% sequence identity to the amino acid sequence of SEQ ID NO: 18.

21. The hybrid enzyme of claim 1, wherein the catalytic module comprises the sequence of amino acids 1-483 of SEQ ID NO: 25 and the carbohydrate domain comprises the amino acid sequence of SEQ ID NO: 18.

22. The hybrid enzyme of claim 1, wherein the catalytic module has at least 90% sequence identity to the sequence of amino acids 1-483 of SEQ ID NO: 25 and the carbohydrate domain differs from the amino acid sequence of SEQ ID NO: 28 in no more than 10 amino acid positions.

23. The hybrid enzyme of claim 1, wherein the catalytic module has at least 90% sequence identity to the sequence of amino acids 1-483 of SEQ ID NO: 25 and the carbohydrate domain differs from the amino acid sequence of SEQ ID NO: 28 in no more than 5 amino acid positions.

24. The hybrid enzyme of claim 1, wherein the catalytic module has at least 95% sequence identity to the sequence of amino acids 1-483 of SEQ ID NO: 25 and the carbohydrate domain differs from the amino acid sequence of SEQ ID NO: 28 in no more than 10 amino acid positions.

25. The hybrid enzyme of claim 1, wherein the catalytic module has at least 95% sequence identity to the sequence of amino acids 1-483 of SEQ ID NO: 25 and the carbohydrate domain differs from the amino acid sequence of SEQ ID NO: 28 in no more than 5 amino acid positions.

26. The hybrid enzyme of claim 1, wherein the catalytic module comprises the sequence of amino acids 1-483 of SEQ ID NO: 25 and the carbohydrate domain comprises the amino acid sequence of SEQ ID NO: 28.

27. The hybrid enzyme of claim 1, wherein the catalytic module has at least 90% sequence identity to the amino acid sequence of SEQ ID NO: 26 and the carbohydrate domain has at least 90% sequence identity to the amino acid sequence of SEQ ID NO: 2.

28. The hybrid enzyme of claim 1, wherein the catalytic module has at least 90% sequence identity to the amino acid sequence of SEQ ID NO: 26 and the carbohydrate domain has at least 95% sequence identity to the amino acid sequence of SEQ ID NO: 2.

29. The hybrid enzyme of claim 1, wherein the catalytic module has at least 95% sequence identity to the amino acid sequence of SEQ ID NO: 26 and the carbohydrate domain has at least 90% sequence identity to the amino acid sequence of SEQ ID NO: 2.

30. The hybrid enzyme of claim 1, wherein the catalytic module has at least 95% sequence identity to the amino acid sequence of SEQ ID NO: 26 and the carbohydrate domain has at least 95% sequence identity to the amino acid sequence of SEQ ID NO: 2.

31. The hybrid enzyme of claim 1, wherein the catalytic module comprises the amino acid sequence of SEQ ID NO: 26 and the carbohydrate domain comprises the amino acid sequence of SEQ ID NO: 2.

32. The hybrid enzyme of claim 1, wherein the catalytic module has at least 90% sequence identity to the amino acid sequence of SEQ ID NO: 26 and the carbohydrate domain has at least 90% sequence identity to the amino acid sequence of SEQ ID NO: 18.

33. The hybrid enzyme of claim 1, wherein the catalytic module has at least 90% sequence identity to the amino acid sequence of SEQ ID NO: 26 and the carbohydrate domain has at least 95% sequence identity to the amino acid sequence of SEQ ID NO: 18.

34. The hybrid enzyme of claim 1, wherein the catalytic module has at least 95% sequence identity to the amino acid sequence of SEQ ID NO: 26 and the carbohydrate domain has at least 90% sequence identity to the amino acid sequence of SEQ ID NO: 18.

35. The hybrid enzyme of claim 1, wherein the catalytic module has at least 95% sequence identity to the amino acid sequence of SEQ ID NO: 26 and the carbohydrate domain has at least 95% sequence identity to the amino acid sequence of SEQ ID NO: 18.

36. The hybrid enzyme of claim 1, wherein the catalytic module comprises the amino acid sequence of SEQ ID NO: 26 and the carbohydrate domain comprises the amino acid sequence of SEQ ID NO: 18.

37. The hybrid enzyme of claim 1, further comprising a linker sequence between the catalytic domain and the carbohydrate-binding module.

38. The hybrid enzyme of claim 37, wherein the linker sequence is selected from the group consisting of SEQ ID NO: 20, SEQ ID NO: 21, SEQ ID NO: 27, and SEQ ID NO: 22, or a fragment thereof.

39. The hybrid enzyme of claim 1, which is encoded by the sequences shown in any of SEQ ID NOS: 82-99.

* * * * *